(12) United States Patent
Nygaard et al.

(10) Patent No.: US 8,647,676 B2
(45) Date of Patent: Feb. 11, 2014

(54) ANTIMICROBIAL COMPOSITION FROM COPEPODS

(75) Inventors: Halvor Nygaard, Bønes (NO); Eyolf Langmyhr, Bergen (NO)

(73) Assignee: Nofima Ingrediens, Fyllingsdalen (NO)

( * ) Notice: Subject to any disclaimer, the term of this patent is extended or adjusted under 35 U.S.C. 154(b) by 354 days.

(21) Appl. No.: 13/124,756

(22) PCT Filed: Oct. 28, 2009

(86) PCT No.: PCT/EP2009/064229
§ 371 (c)(1),
(2), (4) Date: Jul. 6, 2011

(87) PCT Pub. No.: WO2010/049454
PCT Pub. Date: May 6, 2010

(65) Prior Publication Data
US 2011/0256232 A1    Oct. 20, 2011

(30) Foreign Application Priority Data

Oct. 28, 2008   (NO) .................................. 20084555

(51) Int. Cl.
*A61K 35/56*      (2006.01)
*A61P 31/04*      (2006.01)

(52) U.S. Cl.
USPC ........................................... 424/520; 514/2.4

(58) Field of Classification Search
USPC .......................................... 424/520; 514/2.4
See application file for complete search history.

(56) References Cited

U.S. PATENT DOCUMENTS

2009/0130149 A1    5/2009   Raa et al.

FOREIGN PATENT DOCUMENTS

WO    WO 2009/067020    5/2009

OTHER PUBLICATIONS

Destoumieux D, et al.; "Penaeidins, a family of antimicrobial peptides from penaeid schrimp (Crustacea, Decapoda)"; CMLS; Cell. Mol Life Sci. 57, pp. 1260-1271, 2000.

Haug, T. et al.; "Antibacterial activity in four marine crustacean decapods"; Fish & Shelfish Immunology, 12, pp. 371-385; 2002.
Kattner et al; "Lipid composition of Calanus finmarchicus from the north sea and the arctic. A comparative study"; Comp. Biochem and Physiol, vol. 94, No. 1, pp. 185-188, 1989.
Khattab Rafat MA. et al; "Screening for antibacterial and antifungal activities in some selected marine organisms of the Suez Canal and Red Sea."; Egypt. J. Exp. Biol. (Zool.), vol. 4; pp. 223-228; 2008.
Li C. et al.; "Strongylocins, novel antimicrobial peptides from the green sea urchin, *Strongylocentrotus droebachiensis*."; Dev. Comp. Immunol., vol. 32(12); pp. 1430-1440; 2008.
Marcus N. H. et al.; "A guide to the meso-scale production of the copecod *Acartia tonsa*."; Florida Sea Grant, http://www.flseagrant.org/program_areas/aquaculture/copepod/index.htm; 2007.
R. M. Bond; "Digestive enzymes of the pelagic copepod, *Calanus finmarchicus*"; Biol. Bull. Mar. Biol. Labs (Woods hole, Mass.), 67, pp. 461-465; 1934.
Smith V. J. et al.; "Crustins: Enigmatic WAP domain-containing antibacterial proteins from crustaceans"; Developm. and Comp. Immunol., 32; pp. 758-772; 2008.
Solgaard G, et al.; "Proteolytic activities and protease classes in the zooplankton species *Calanus finmarchicus*"; Comp. Biochem and Physiology, part B 147, pp. 475-481, 2007.
Sperstad SV, et al.; "Characterization of crustins from the hemocytes of the spider crab, *Hyas araneus*, and the red king crab, *Paralithodes camtschaticus*."; Dev. Comp. Immunol. vol. 33(4); pp. 583-581; 2009.
Stensvåg K. et al.; "Arasin 1, a proline-arginine-rich antimicrobial peptide isolated from the spider crab, *Hyas araneus*."; Dev. Comp. Immunol., vol. 32(3); pp. 275-285; 2008.
Strøm et al; "Biosynthesis off trimethylamine oxide in *Calanus finmarchicus*. Properties of a soluble trimethylamine monooxygenase"; Comp Biochem and Physiol, vol. 65, No. 2, pp. 243-249, 1980.
Yusuf A. A. et al.; "Seasonal Variations in the Physical Characteristics of the Copecod Calanus finmarchicus (Gunnerus) Along the North Atlantic,"; Journ. Biol. Sciences, vol. 8(1); pp. 95-100; 2008.

*Primary Examiner* — Rosanne Kosson
(74) *Attorney, Agent, or Firm* — Gifford, Krass, Sprinkle, Anderson & Citkowski, P.C.

(57) ABSTRACT

The present invention relates to an antimicrobial composition, and to a process for the preparation of such a composition. The invention also relates to the use of such an antimicrobial composition. The present invention further relates to the use of the antimicrobial composition as a pharmaceutical.

16 Claims, 12 Drawing Sheets

US 8,647,676 B2

ANTIMICROBIAL COMPOSITION FROM COPEPODS

CROSS-REFERENCE TO RELATED APPLICATIONS

This application is the U.S. National Phase of PCT/EP2009/064229 filed Oct. 28, 2009, which claims priority of Norwegian Patent Application 20084555 filed Oct. 28, 2008.

All patent and non-patent references cited in the present application, are also hereby incorporated by reference in their entirety.

The norwegian patent application 20084555 and the references cited herein are hereby incorporated in the patent application in its entirety.

FIELD OF INVENTION

The present invention relates to an antimicrobial composition obtained from the marine copepod *Calanus finmarchicus*, and to a process for the preparation of such a composition. The invention also relates to the use of such an antimicrobial composition.

BACKGROUND OF INVENTION

Copepods are a group of small crustaceans found in the sea and nearly every freshwater habitat. According to the classification system of Martin and Davies (2001), the copepods form a subclass belonging to the subphylum Crustacea (crustaceans). Subphylum Crustacea is a large group of the phylum Arthropoda, comprising almost 52,000 described species. Six classes of the Crustaceans are usually recognized. Subclass Copepoda of the class Maxillopoda comprise ten orders, of which the order Calanoida include 43 families with about 2000 species. Many species are planktonic (drifting in sea waters), but more are benthic (living on the ocean floor), and some continental species may live in limno-terrestrial habitats and other wet terrestrial places, such as swamps, under leaf fall in wet forests, bogs, springs, ephemeral ponds and puddles, damp moss, or water-filled recesses (phytotelmata) of plants such as bromeliads and pitcher plants. Many live underground in marine and freshwater caves, sinkholes, or stream beds.

Two of the most abundant northern calanoid species is *C. finmarchicus* which is commonly regarded as a northern boreal species inhabiting North Atlantic Ocean, while *C. hyperboreus* is an arctic species.

The evolution of antibiotic-resistant pathogenic bacteria has stimulated the search for alternative antimicrobial agents from natural sources. Antimicrobial activity has previously been detected in several decapod crustaceans, including lobster, crabs, shrimps and freshwater crayfish. The search for novel compounds displaying antimicrobial activity has led to the identification of several antimicrobial peptides and proteins in decapod crustaceans (Haug et al., 2002).

SUMMARY OF INVENTION

The present invention relates to an antimicrobial composition from a marine copepod, such as *Calanus finmarchicus*, and to a process for the preparation of such a composition. The invention also relates to the use of such an antimicrobial composition. The present invention further relates to a pharmaceutical composition obtained from *Calanus finmarchicus* and to the use of a composition obtained from *Calanus finmarchicus* in the treatment of microbial infections in an individual in need thereof.

DEFINITIONS

The term proteinaceous is defined as any molecule comprising amino acids connected by amide (peptide) bonds. Non-proteinaceous is any molecule, which does not comprise amino acids connected by amide (peptide) bonds.

A protein in the present context is an organic macromolecule made of amino acids. A protein is a biopolymer. Proteins consist of one or more polypeptide molecules.

A peptide in the present context is defined as a molecule consisting of 2 or more amino acids. Peptides are smaller than proteins. The dividing line between a peptide and a protein/polypeptide is at about 50 amino acids. Depending on the number of amino acids, peptides are called dipeptides, tripeptides, tetrapeptides, and so on.

A nucleotide is composed of a nucleobase (nitrogenous base), a five-carbon sugar (either ribose or 2'-deoxyribose), and one to three phosphate groups. Together, the nucleobase and sugar comprise a nucleoside. The phosphate groups form bonds with either the 2, 3, or 5-carbon of the sugar, with the 5-carbon site most common. Ribonucleotides are nucleotides where the sugar is ribose, and deoxyribonucleotides contain the sugar deoxyribose. Nucleotides can contain either a purine or pyrimidine base. Nucleic acids are polymeric macromolecules made from nucleotide monomers. In DNA, the purine bases are adenine and guanine, while the pyrimidines are thymine and cytosine. RNA uses uracil in place of thymine.

A nucleic acid is a macromolecule or a biopolymer composed of chains of monomeric nucleotides. A non-nucleic acid is a molecule which does not contain nucleotides.

An aerobic organism or aerobe is an organism that can survive and grow in an oxygenated environment. Obligate aerobes require oxygen for aerobic cellular respiration. Facultative anaerobes can use oxygen, but also have anaerobic methods of energy production. Microaerophiles are organisms that may use oxygen, but only at low concentrations. Aerotolerant organisms can survive in the presence of oxygen, but they are anaerobic because they do not use it as a terminal electron acceptor.

An anaerobic organism or anaerobe is any organism that does not require oxygen for growth and may even die in its presence. There are three types: obligate anaerobes, which cannot use oxygen for growth and are even harmed by it; aerotolerant organisms, which cannot use oxygen for growth, but tolerate the presence of it; and facultative anaerobes, which can grow without oxygen, but if present can utilize it.

A microorganism or microbe is an organism that is microscopic.

Microorganisms are very diverse; they include bacteria, fungi, archaea, viruses and protists; microscopic plants (called green algae); and animals such as plankton and the planarian. Pathogenic microorganisms cause infection.

Bacteria can be classified on the basis of cell structure, cellular metabolism or on differences in cell components such as DNA, fatty acids, pigments, antigens and quinones. By combining morphology and Gram-staining, most bacteria can be classified as belonging to one of four groups: Gram-positive cocci, Gram-positive bacilli, Gram-negative cocci and Gram-negative bacilli. Bacteria can be aerobic, anaerobic, or facultative anaerobic.

An antimicrobial is a substance that kills or inhibits the growth of microorganisms such as bacteria, fungi, or protozoans, as well as destroying viruses. Antimicrobial drugs either kill microbes (microbicidal) or prevent the growth of microbes (microbistatic). The main classes of antimicrobial agents are antibiotics (antibacterials), antivirals and antifungals targeting bacteria, viruses and fungi respectively.

The term broad-spectrum antibiotic refers to an antibiotic with activity against a wide range of disease-causing bacteria. It is also means that it acts against both Gram-positive and Gram-negative bacteria. This is in contrast to a narrow-spectrum antibiotic which is effective against only specific families of bacteria.

Antiseptics are antimicrobial substances that are applied to living tissue/skin to reduce the possibility of infection, sepsis, or putrefaction.

A preservative is a compound that is added to products such as foods, pharmaceuticals, paints, biological samples, wood, etc. to prevent decomposition by microbial growth or by undesirable chemical changes.

Disinfectants are antimicrobial agents that are applied to non-living objects to destroy microorganisms, the process of which is known as disinfection. Disinfection may be defined as: Cleaning an article of some or all of the pathogenic organisms which may cause infection.

Small molecules are low molecular weight organic compounds, which by definition are not polymers. The upper molecular weight limit for a small molecule is approximately 1000 Daltons (Da). Biopolymers such as nucleic acids, proteins, and polysaccharides (such as starch or cellulose) are not small molecules. Very small oligomers are also usually considered small molecules, such as dinucleotides, small peptides such as the antioxidant glutathione, and disaccharides such as sucrose. One group of small molecules are known as secondary metabolites.

Secondary metabolites are small organic compounds of metabolism that are not directly involved in the normal growth, development, or reproduction of organisms.

A biomolecule is any organic molecule that is produced by a living organism, including large polymeric molecules such as proteins, polysaccharides, and nucleic acids as well as small molecules such as primary metabolites, secondary metabolites, and natural products.

Organic compounds are molecules that contain carbon with the exception of a few types of compounds such as carbonates, simple oxides of carbon and cyanides, as well as the allotropes of carbon, which are considered inorganic. They can be either natural or synthetic organic compounds. Based upon the size of organic compounds, they can be classified as either small molecules or polymers.

A solvent is a liquid, solid, or gas that dissolves another solid, liquid, or gaseous solute, resulting in a solution. The most common solvent in everyday life is water.

Chemical Polarity refers to a separation of electric charge leading to a molecule having an electric dipole. Polar molecules can bond together due to dipole-dipole intermolecular forces between one molecule (or part of a large molecule) with asymmetrical charge distribution and another molecule also with asymmetrical charge distribution. Molecular polarity is dependent on the difference in electronegativity between atoms in a compound and the asymmetry of the compound's structure. For example, a molecule of water is polar because of the unequal sharing of its electrons in a "bent" structure, whereas methane is considered non-polar because the carbon shares the electrons with the hydrogen atoms uniformly. A molecule may be polar either as a result of polar bonds due to differences in electronegativity as described above, or as a result of an asymmetric arrangement of non-polar covalent bonds and non-bonding pairs of electrons known as a full molecular orbital. Due to the polar nature of the water molecule itself, polar molecules are generally able to dissolve in water. A non-polar compound occurs when there is an equal sharing of electrons between different atoms. Examples of household non-polar compounds include fats, oil and petrol/gasoline. Therefore (per the "oil and water" rule of thumb), most non-polar molecules are water insoluble (hydrophobic) at room temperature. However many non-polar organic solvents, such as turpentine, are able to dissolve polar substances.

An infection is the colonization of a host organism by a foreign species, usually a microorganism. In an infection, the infecting organism seeks to utilize the host's resources to multiply, usually at the expense of the host. The infecting organism, or pathogen, interferes with the normal functioning of the host. Primary and secondary infection may either refer to succeeding infections or different stages of one and the same infection.

A fungus is any member of a large group of eukaryotic organisms that includes microorganisms such as yeasts and molds, as well as the more familiar mushrooms.

An antifungal is defined as any compound capable of killing or inhibiting the growth of a fungus.

Anti-fouling: The effect of controlling, reducing and/or eliminating over time the number of undesirable microorganisms in a bio-film.

Bio-film: Habitation of microbial organisms on a solid or semi-solid surface.

Resistance or drug resistance is the reduction in effectiveness of a drug in curing a disease or improving a patient's symptoms. When the drug is not intended to kill or inhibit a pathogen, then the term is equivalent to dosage failure or drug tolerance. More commonly, the term is used in the context of diseases caused by pathogens. Pathogens are said to be drug-resistant when drugs meant to neutralize them have reduced effect. When an organism is resistant to more than one drug, it is said to be multi-resistant. Drug resistance is an example of evolution in microorganisms. Individuals that are not susceptible to the drug effects are capable of surviving drug treatment, and therefore have greater fitness than susceptible individuals. By the process of natural selection, drug resistant traits are selected for in subsequent offspring, resulting in a population that is drug resistant.

A gel is a semirigid colloidal dispersion of a solid preferably with a liquid. A gel can further be defined as a solid, jelly-like material that can have properties ranging from soft and weak to hard and tough. Gels are defined as a substantially dilute crosslinked system, which exhibits no flow when in the steady-state.

A lotion is a low- to medium-viscosity, topical preparation intended for application to unbroken skin; creams and gels have a higher viscosity than lotions.

DETAILED DESCRIPTION OF THE INVENTION

Figure 1:
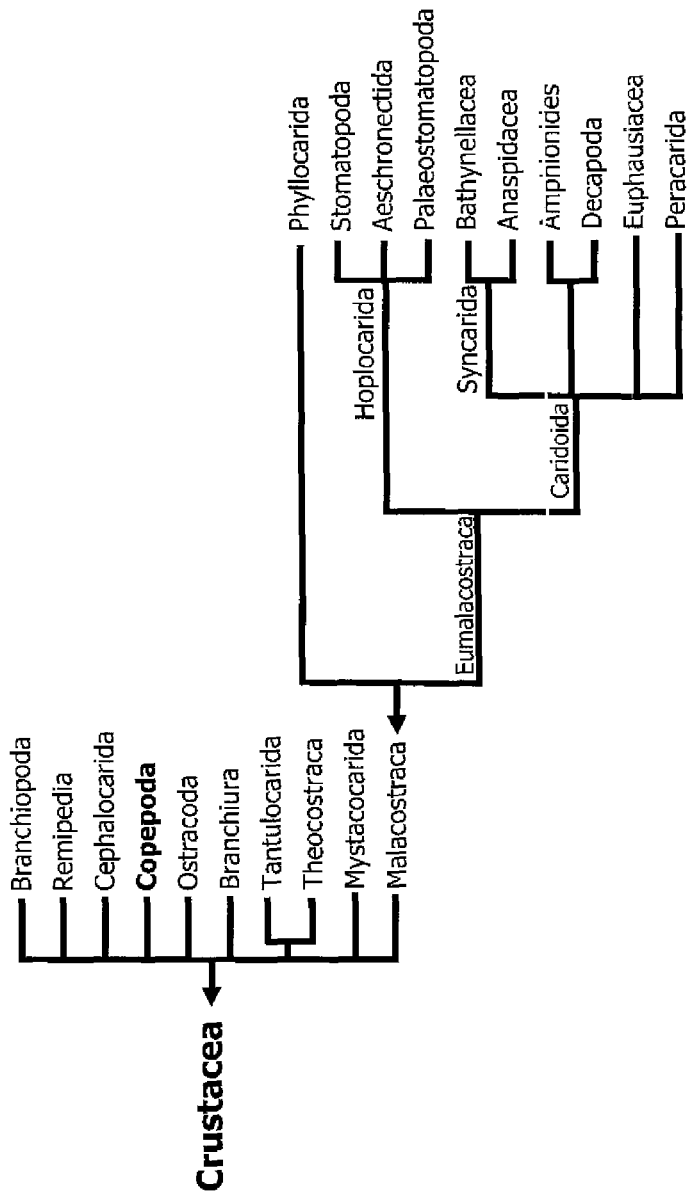
FIG. 1. shows the phylogeny of the Crustacea.

The present invention was discovered through the surprising observation that samples of the marine copepod *Calanus finmarchicus* (crustacea) could be stored for several days at ambient temperature without developing off-odors or other signs of spoilage. Furthermore, it was observed that the samples did not contain bacteria detectable by the standard methods for enumeration of aerobic micro-organisms, and that an extract from *Calanus finmarchicus* possesses antimicrobial activity directed against various bacterial strains and some fungi.

Another copepod species, *C. hyperboreus*, was also investigated for antimicrobial activity. Antimicrobial activity was not detected in the *C. hyperboreus*, suggesting that the antimicrobial activity discovered in *C. finmarchicus* extracts is specific for this species of *Calanus* copepods.

The present invention thus relates in one embodiment to an antimicrobial composition, wherein the composition is obtained from copepods, such as *Calanus* species, particularly the marine copepod *Calanus finmarchicus*.

In the present invention the antimicrobial composition comprises one or more identical or different antimicrobial compounds.

In one embodiment the antimicrobial composition comprises a single antimicrobial compound.

In other embodiments the antimicrobial composition comprises two or more different antimicrobial compounds, such as three, for example four, such as five, for example six, such as seven, for example eight, such as nine, for example ten different antimicrobial compounds.

*Calanus finmarchicus*

*Calanus* is a genus of marine copepod in the family Calanidae (Order Calanoida). Calimidae is the largest taxonomic family of calanoid copepods. The genus *Calanus* may be the most abundant animal genus on Earth. Copepods of the genera *Calanus* and *Neocalanus* are ecologically important in the Arctic and subarctic regions of the world's oceans.

*Calanus finmarchicus* is a zooplankton species, which is found in enormous amounts in the North Sea. The body length is up to 5.4 mm for females and 3.6 mm for males. *C. finmarchicus* is high in protein and contains valuable omega-3 fatty acids. It contains also high amounts of antioxidant. *Calanus finmarchicus* is the dominant copepod in the northern North Atlantic, it plays a vital role in economy of the oceans, forming middle link in food chain leading from phytoplankton up to commercially important fish species, many of which feed on this species either as larvae or as adults. Plays equally important role in global carbon cycle, since large proportion of fixed carbon dioxide passes through oceanic food web as phytoplankton consumed by *C. finmarchicus*.

In addition to *C. finmarchicus*, species of *Calanus* include: *Calanus brevicornis*, *Calanus glacialis*, *Calanus helgolandicus*, *Calanus hyperboreus*, *Calanus marshallae*, *Calanus pacificus*, *Calanus propinquus*, *Calanus simillimus*, *Calanus sinicus*.

Methods for Obtaining the Antimicrobial Composition from *C. finmarchicus*

The antimicrobial composition of the present invention can be prepared form *C. finmarchicus* by any method suitable for obtaining a composition with antimicrobial activity from *C. finmarchicus*.

In one embodiment the present invention relates to a process for producing a composition comprising one or more antimicrobial compounds, said process comprising the steps of:
  i) providing a sample comprising *C. finmarchicus* or parts of *C. finmarchicus*,
  ii) performing one or more purification steps and/or isolation steps and/or concentration steps resulting in purification and/or isolation and/or concentration from said sample of a composition comprising one or more antimicrobial compounds, wherein at least some of said antimicrobial compounds are preferably non-proteinaceous and non-nucleic acid antimicrobial compounds.

The purpose of the purification step is the removal of undesirable substances. Undesirable substances in the present context are any substances that do not contribute directly or indirectly to the antimicrobial effect of the composition. Undesirable substances can be, but are not limited to salts, natural environmental compounds, structural elements of the copepods not exhibiting antimicrobial activity, etc. In one embodiment purification can be performed by dividing the sample into two or more fractions or phases and discarding the fraction or phase not comprising the antimicrobial composition.

The purpose of the isolation step is to retain desirable substances. Desirable substances in the present context are any substances that directly or indirectly contribute to the antimicrobial effect of the composition. The isolation can be performed by isolating or separating the one or more antimicrobial compounds according to chemical and/or physical properties. Examples of chemical properties include affinity for one or more compounds and chemical stability. Examples of physical properties include mass or size, charge, solubility, polarity, distribution, melting point, boiling point and absorbance.

The purpose of the concentration step is to remove solvents fully or partly to obtain a composition with a higher antimicrobial activity than before said concentration step was performed. The solvent can be any liquid, wherein the one or more antimicrobial compounds are comprised. Concentration can in one embodiment be performed by evaporation of the solvent.

In one embodiment, an aqueous solution comprising the antimicrobial composition is obtained by performing at least one physical processing step, such as by centrifugation.

The invention in one embodiment relates to a process for producing an antimicrobial composition, wherein a sample comprising *C. finmarchicus* is subjected to the following process steps;
  i) providing a sample comprising *C. finmarchicus* or parts of *C. finmarchicus*,
  ii) separating said sample into at least two, such as three phases by centrifugation, i.e. at least two of a sediment phase, an oil phase and an aqueous phase,
  iii) and isolation of said aqueous phase, wherein said aqueous phase comprises the antimicrobial composition.

The invention in one embodiment relates to a process for producing an antimicrobial composition, wherein a sample comprising *C. finmarchicus* is subjected to the following process steps;
  i) providing a sample comprising *C. finmarchicus* or parts of *C. finmarchicus*,
  ii) separating said sample into at least two, such as three phases by centrifugation, i.e. at least two of a sediment phase, an oil phase and an aqueous phase,
  iii) and isolation of said sediment phase, wherein said sediment phase comprises the antimicrobial composition.

The invention in one embodiment relates to a process for producing an antimicrobial composition, wherein a sample comprising *C. finmarchicus* is subjected to the following process steps;
  i) providing a sample comprising *C. finmarchicus* or parts of *C. finmarchicus*,
  ii) separating said sample into at least two, such as three phases by centrifugation, i.e. at least two of a sediment phase, an oil phase and an aqueous phase,
  iii) and isolation of said oil phase, wherein said oil phase comprises the antimicrobial composition.

In one embodiment of the present invention, a concentrated extract with increased antimicrobial activity as compared to the antimicrobial activity of the aqueous phase is obtained by performing an extraction of a sample comprising *C. finmarchicus*, using an extraction agent such as methanol.

Accordingly, the invention in another embodiment relates to a process for the isolation or extraction of an antimicrobial composition, wherein a sample comprising *C. finmarchicus* is subjected to the following method steps:
  i) providing a sample comprising *C. finmarchicus* or parts of *C. finmarchicus*,
  ii) extracting said sample using one or more extraction agents,
  iii) removing said one or more extraction agents to obtain a concentrated extract, and optionally
  iv) dissolving the concentrated extract,
thereby obtaining a concentrated antimicrobial composition comprising one or more antimicrobial compounds.

The invention in another embodiment relates to a process for the isolation or extraction of an antimicrobial composition, wherein a sample comprising *C. finmarchicus* is subjected to the following method steps:
  i) providing a sample comprising *C. finmarchicus* or parts of *C. finmarchicus*,
  ii) extracting said sample using one or more extraction agents,
  iii) removing said one or more extraction agents to obtain a concentrated extract, and optionally
  iv) dissolving the concentrated extract,
  v) further subjecting said concentrated extract to one or more fractionation steps and/or one or more purification steps and/or one or more isolation steps, thereby obtaining a concentrated antimicrobial composition comprising one or more antimicrobial compounds. The one or more fractionation steps and/or one or more purification steps and/or one or more isolation steps comprises one or more of the following steps: HPLC, Wessel-Flügge extraction, size exclusion, anion exchange, cation exchange, reversed phase chromatography, semi-preparative reversed phase chromatography.

In one embodiment the sample comprising *C. finmarchicus* preferably comprises whole *C. finmarchicus* and/or whole *C. finmarchicus* cells and/or disrupted/degraded *C. finmarchicus* cells. In other embodiments the sample comprising *C. finmarchicus* is a previously processed *C. finmarchicus* sample, such as comprising crushed *C. finmarchicus*. In one embodiment the *C. finmarchicus* sample is a *C. finmarchicus* homogenate obtained by state of the art methods. The *C. finmarchicus* homogenate can in one embodiment comprise and/or consist of particles with an average diameter of less than 1 mm, 0.5 mm, 0.25 mm, 0.1 mm, 0.05 mm and/or 0.01 mm. In one embodiment the *C. finmarchicus* homogenate can be use as an antimicrobial composition. In one embodiment the *C. finmarchicus* homogenate is used for treatment of an individual in need thereof.

In one embodiment, the sample comprising whole *C. finmarchicus* is dried prior to the extraction step. Drying may be performed in any suitable way. In a preferred embodiment the drying is performed by freeze-drying. Other drying methods may be used such as e.g. heat pump drying, hot air drying, indirect and direct steam drying.

The extraction in step ii) above may be performed in any suitable way. In a preferred embodiment the extraction agent or solvent used is methanol. In other embodiments acetone and/or ethanol may be used as the extraction agent.

The removal of the extraction agent or solvent may in one embodiment be performed by evaporation. The solvent may be removed fully or partly. Evaporation of the solvent can be performed in any suitable way known in the art. In one embodiment, evaporation of the solvent is performed by vacuum evaporation. In another embodiment atmospheric evaporation is used.

The concentrated extract obtained in step iv) above can be dissolved in any suitable solvent. In one embodiment, the solvent is an aqueous solvent. In a preferred embodiment of the present invention, the solvent is water, more preferred deionised water.

In one embodiment, the antimicrobial composition is obtained by a process comprising a step of deproteinisation, i.e. removing proteinaceous compounds from the composition. In one example the deproteinisation could be performed by a method comprising the step of acetone precipitation and/or salting out. Salting out is a method of separating proteins based on the principle that proteins are less soluble at high salt concentrations. The salt concentration needed for the protein to precipitate out of the solution differs from protein to protein. Dialysis can be used to remove the salt if needed.

In one embodiment, the preparation of the antimicrobial composition according to the present invention further comprises the step of filtering the obtained solution containing the antimicrobial composition. Filtering can be performed on or more times using one or more filter types. Filtering methods are known in the art and can for example be performed by filtering through a glass fiber filter and/or a microporous cellulose acetate filter or any other suitable filtering procedure as determined by the skilled person. In a particular embodiment, a microporous cellulose acetate filter with pore size 0.2 µm is used.

According to the present invention, filtering can be performed using filters selected from the group consisting of purified cotton filters, glass fiber filters, paper filters and microporous cellulose acetate filters.

In one embodiment of the present invention, the one or more antimicrobial compounds comprised within the antimicrobial composition are further isolated by performing one or more further extraction steps.

In one embodiment, the one or more further extraction step comprises a Wessel-Flügge extraction.

In one embodiment, the one or more further extraction step comprises one or more chromatography steps, such as one further chromatography extraction, for example two further chromatography extractions, such as three further chromatography extractions.

In one embodiment, the further extraction step comprises a solid-phase extraction, such as QMA anion exchange or reverse-phase column chromatography.

The present invention is also directed at the further isolation of the one or more antimicrobial compounds comprised within the antimicrobial composition by performing one or more chromatography steps, such as by HPLC, and selecting the fractions wherein the antimicrobial activity is retained.

In one embodiment of the present invention, the antimicrobial composition is further analysed by mass spectroscopy.

In one embodiment the present invention is directed to an antimicrobial composition comprising one or more C. finmarchicus antimicrobial compounds, wherein said composition is obtained or obtainable by a process comprising the steps of:
  i) providing a sample comprising C. finmarchicus or parts thereof,
  ii) performing one or more purification steps and/or isolation steps and/or concentration steps resulting in purification and/or isolation and/or concentration from said sample of a composition comprising one or more antimicrobial compounds, wherein at least some of said antimicrobial compounds are preferably non-proteinaceous and non-nucleic acid antimicrobial compounds.

In another embodiment the present invention is directed to an antimicrobial composition comprising one or more C. finmarchicus antimicrobial compounds, wherein said composition is obtained or obtainable by any process mentioned in this applications.

Figure 9:
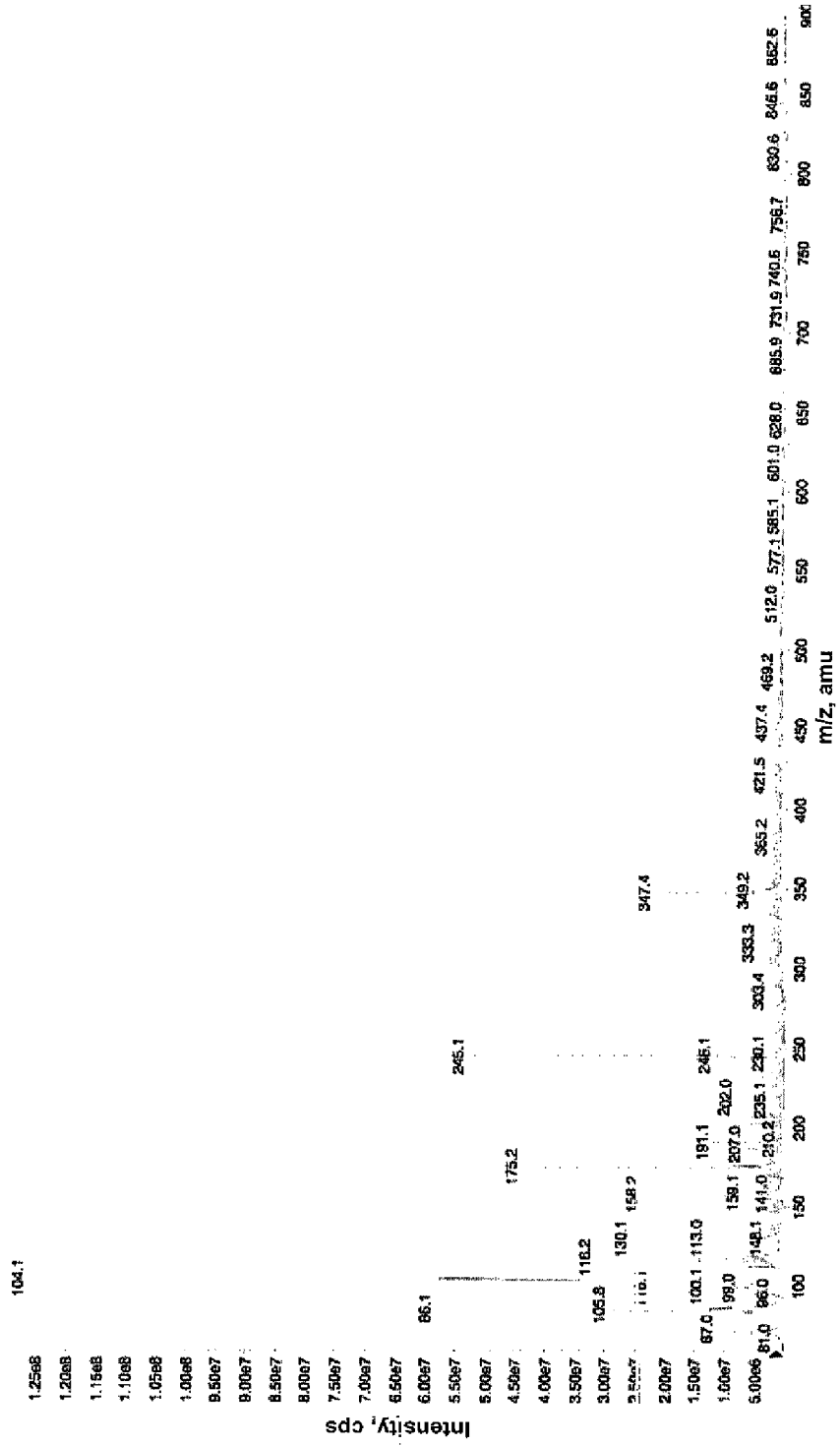
FIG. 9. MS-analysis of fraction 4 from FIG. 8.

The invention further relates to a method for producing one or more anti-microbial compounds, said method comprising the steps of:
  i) providing an extract or a homogenate of C. finmarchicus, and
  ii) isolating from said extract or homogenate one or more anti-microbial compounds,
  wherein said one or more anti-microbial compounds are characterised by exhibiting m/z values in a mass spectroscopical analysis of a) from 235 to 255 and/or from b) 335 to 360, essentially as illustrated in FIG. 9.

The compounds are preferably isolated by one or more chromatographical purification steps; such as purification steps selected from, but not limited to, a Wessel-Flügge extraction step, a solid phase extraction (anion exchange) step, a solid phase extraction (reverse phase) step; and a high pressure liquid chromatography (HPLC) step (with or without polar end-capping); including reverse phase HPLC and normal phase HPLC.

The invention also relates to one or more anti-microbial agent(s) or a composition comprising same, said agent(s) or said composition being obtainable by a method comprising the steps of:
  1. providing an extract or a homogenate of C. finmarchicus, and
  2. isolating from said extract or homogenate said one or more anti-microbial compounds,
  wherein said one or more anti-microbial compounds are characterised by exhibiting m/z values in a mass spectroscopical analysis of a) from 235 to 255 and/or from b) 335 to 360, essentially as illustrated in FIG. 9.
  wherein said one or more anti-microbial compounds are preferably isolated by one or more chromatographical purification steps; such as purification steps selected from, but not limited to, a Wessel-Flügge extraction step, a solid phase extraction (anion exchange) step, a solid phase extraction (reverse phase) step; and a high pressure liquid chromatography (HPLC) step (with or without polar end-capping); including reverse phase HPLC and normal phase HPLC.

The m/z values in a mass spectroscopical analysis of a) from 235 to 255 mentioned above can in one embodiment be from 235 to 240, and/or from 240 to 245, and/or from 245 to 250, and/or 250 to 255.

The m/z values in a mass spectroscopical analysis of b) from 335 to 360 mentioned above can in one embodiment be from 335 to 340, and/or 340 to 345, and/or 345 to 350, and/or 350 to 355 and/or 355 to 360.

Chemical Polarity of Compounds

The antimicrobial composition according to the present invention preferably comprises one or more polar compounds exhibiting an antimicrobial activity.

The polarity of a compound is dependent on the difference in electronegativity between atoms in a compound and the asymmetry of the compound's structure. In a non-polar compound the electrons of the molecule are distributed uniformly, whereas in a polar compound, the electrons are distributed asymmetrically giving rise to a molecule with an asymmetrical charge distribution.

Polarity underlies a number of physical properties including surface tension, solubility, and melting- and boiling-points. Polarity of a compound can e.g. be assessed by its ability to dissolve in aqueous solvents, such as water. A water-soluble compound is polar, whereas a compound which is not soluble in water is non-polar.

The polarity of a particular compound or composition can be estimated by a range of different methods.

In organic chemistry and the pharmaceutical sciences, a partition—(P) or distribution coefficient (D) is the ratio of concentrations of a compound in the two phases of a mixture of two immiscible solvents at equilibrium. Hence these coefficients are a measure of differential solubility of the compound between these two solvents.

Normally one of the solvents chosen is water while the second is hydrophobic such as octanol. Hence both the partition and distribution coefficient are measures of how hydrophilic ("water loving") or hydrophobic ("water fearing") a chemical substance is, in other words how polar a compound is. Partition coefficients are useful for example in estimating distribution of drugs within the body. Hydrophobic drugs with high partition coefficients are preferentially distributed to hydrophobic compartments such as lipid bilayers of cells while hydrophilic drugs (low partition coefficients) preferentially are found in hydrophilic compartments such as blood serum.

The partition coefficient is a ratio of concentrations of un-ionized compound between the two solutions. To measure the partition coefficient of ionizable solutes, the pH of the aqueous phase is adjusted such that the predominant form of the compound is un-ionized. The logarithm of the ratio of the concentrations of the un-ionized solute in the solvents is called log P:

$$\log P_{oct/wat} = \log\left(\frac{[\text{solute}]_{octanol}}{[\text{solute}]_{water}^{un\text{-}ionized}}\right)$$

Reverse phase HPLC can be used to estimate log P of a compound and/or a composition.

In one embodiment of the present invention, the log P of the one or more antimicrobial compounds in the composition of the present invention is in the range of −3 to 6, more preferred −1.5 to 4, such as in the range of −1.5 to −1.4, for example −1.4 to −1.3, such as −1.3 to −1.2, for example −1.2 to −1.1, such as −1.1 to −1.0, for example −1.0 to −0.9, such as −0.9 to −0.8, for example −0.8 to −0.7, such as −0.7 to −0.6, for example −0.6 to −0.5, such as −0.5 to −0.4, for example −0.4 to −0.3, such as −0.3 to −0.2, for example −0.2 to −0.1, such as −0.1 to 0.0, for example 0.0 to 0.1, such as 0.1 to 0.2, for example 0.2 to 0.3, such as 0.3 to 0.4, for example 0.4 to 0.5, such as 0.5 to 0.6, for example 0.6 to 0.7, such as 0.7 to 0.8, for example 0.8 to 0.9, such as 0.9 to 1.0, for example 1.0 to 1.1, such as 1.1 to 1.2, for example 1.2 to 1.3, such as 1.3 to 1.4, for example 1.4 to 1.5, such as 1.5 to 1.6, for example 1.6 to 1.7, such as 1.7 to 1.8, for example 1.8 to 1.9, such as 1.9 to 2.0, for example 2.0 to 2.1, such as 2.1 to 2.2, for example 2.2 to 2.3, such as 2.3 to 2.4, for example 2.4 to 2.5, such as 2.5 to 2.6, for example 2.6 to 2.7, such as 2.7 to 2.8, for example 2.8 to 2.9, such as 2.9 to 3.0, for example 3.0 to 3.1, such as 3.1 to 3.2, for example 3.2 to 3.3, such as 3.3 to 3.4, for example 3.4 to 3.5, such as 3.5 to 3.6, for example 3.6 to 3.7, such as 3.7 to 3.8, for example 3.8 to 3.9, such as 3.9 to 4.0.

In another embodiment the log P value is less than 2, such as less than 1.9 for example less than 1.8, such as less than 1.7, for example less than 1.6, such as less than 1.5, for example less than 1.4, such as less than 1.3, for example less than 1.2, such as less than 1.1, for example less than 1.0, such as less than 0.9, for example less than 0.8, such as less than 0.7, for example less than 0.6, such as less than 0.5, for example less than 0.4, such as less than 0.3, for example less than 0.2, such as less than 0.1, for example less than 0.0, such as less than −0.1, for example less than −0.2, such as less than −0.3, for example less than −0.4, such as less than −0.5, for example less than −0.6, such as less than −0.7, for example less than −0.8, such as less than −0.9, for example less than −1.0, such as less than −1.1, for example less than −1.2, such as less than −1.3.

Type of Action

Overall, there are three types of action of antimicrobial agents; i) static action where growth is inhibited, ii) cidal action where organisms are killed and iii) lytic action where organisms are killed and lysed.

If a compound is static or biostatic, the growth of the microorganism is inhibited, but it is not killed by the treatment. If a population of microorganisms is treated with a static antimicrobial compound, the number of viable microorganisms is not decreased by the treatment compared to the total number of microorganisms.

If a compound is cidic or biocidic, the microorganism is killed by the treatment. If a population of microorganisms is treated with a cidic antimicrobial compound, the number of viable microorganisms is decreased compared to the total number of microorganisms.

If a compound is lytic or biolytic, the microorganism is lysed and killed by the treatment. If a population of microorganisms is treated with a lytic antimicrobial compound, both the number of viable and the total number of microorganisms is decreased to a similar extent.

In relation to bacteria, the terms used are bacteriostatic, bacteriocidic and bacteriolytic, respectively.

According to the present invention the antimicrobial composition can be static, cidic or lytic.

In one embodiment the antimicrobial composition is static.
In one embodiment the antimicrobial composition is cidic.
In one embodiment the antimicrobial composition is lytic.
In one embodiment the antimicrobial composition is both cidic and lytic.

In a preferred embodiment of the present invention, the antimicrobial composition of the present invention is bacteriocidic.

In another embodiment of the present invention, the antimicrobial composition of the present invention is not bacteriolytic.

The anti-fungal activity of the antimicrobial composition of the present invention is either static, cidic or lytic.

The type of antimicrobial action of a particular compound or composition can be determined by several different ways known in the art.

Characteristics of the Antimicrobial Composition

In one embodiment the antimicrobial composition comprises one or more compounds with the chemical characteristics disclosed in the examples and figures of the present invention.

In one embodiment the antimicrobial composition of the present invention comprises one or more antimicrobial compounds.

In one embodiment, the antimicrobial composition is water soluble.

In one embodiment the antimicrobial composition comprises one or more polar antimicrobial compounds.

In one embodiment, the one or more antimicrobial compounds of the present invention is/are heat stable. In one example the antimicrobial composition fully or partially retains its antimicrobial activity after heating. Heating of the antimicrobial composition can be performed at 60-130° C., such as in the range of 60-65° C., 65-70° C., 70-75° C., 75-80° C., 80-85° C., 85-90° C., 90-95° C., 95-100° C., 100-105° C., 105-110° C., 110-115° C., 115-120° C., 120-125° C., 125-130° C.

In one embodiment heating is performed at about 65-75° C., more preferred at about 70° C.

In one embodiment heating is performed at about 90-110° C., more preferred at about 100° C.

In yet another embodiment heating is performed at about 120-125° C., more preferred at about 121° C.

According to the present invention, heating can be performed for shorter or longer periods of time, such as from a minute to several hours. Heating can for example be performed for a few minutes such as in the range of about 1-5 minutes, 5-10 minutes, 10-15 minutes, 15-20 minutes, 20-25 minutes, 25-30 minutes, 30 minutes-1 hour.

In a preferred embodiment, heating is performed for about 5-20 minutes, more preferred for about 10-15 minutes.

In one embodiment heating is performed at about 65-75° C., more preferred at about 70° C. such as for about 10-15 minutes.

In one embodiment heating is performed at about 90-110° C., more preferred at about 100° C. such as for about 10-15 minutes.

In yet another embodiment heating is performed at about 120-125° C., more preferred at about 121° C. such as for about 10-15 minutes.

In one embodiment, the one or more antimicrobial compounds are not proteinaceous compounds, i.e. they are not peptides or proteins. In one example, the antimicrobial composition is resistant to proteolytic enzymes, thereby indicating that the compound does not contain amide or peptide bonds.

In one example, the antimicrobial composition is resistant to pepsin treatment, meaning that the antimicrobial composition fully retains its antimicrobial activity following pepsin treatment.

In another example, the antimicrobial composition is resistant to alcalase treatment, meaning that the antimicrobial composition fully retains its antimicrobial activity following alcalase treatment.

In another example, the antimicrobial composition is resistant to Proteinase K treatment, meaning that the antimicrobial composition fully retains its antimicrobial activity following Proteinase K treatment.

In one embodiment the antimicrobial composition does not contain an antimicrobial compound in the form of a nucleotide or nucleic acids, i.e. it is a non-nucleic acid.

In one embodiment the antimicrobial composition contains one or more antimicrobial nucleotides or nucleic acids.

In one embodiment the one or more antimicrobial compounds are proteinaceous compounds, such as one or more cyclic peptides.

Examples of known cyclic peptides include, but are not limited to amanitins, Bacitracin, colistin, cyclosporine, cyclotide, dactinomycin, daptomycin, nisin, polymyxin b, pristinamycin, octreotide, valinomycin.

Carbohydrates are simple organic compounds that are aldehydes or ketones with many hydroxyl groups added, usually one on each carbon atom that is not part of the aldehyde or ketone functional group. The basic carbohydrate units are called monosaccharides.

In one embodiment at least one of the one or more antimicrobial compounds of the present invention comprises a carbohydrate.

In another embodiment at least one of the one or more antimicrobial compounds of the present invention does not comprise a carbohydrate.

In one embodiment, the one or more antimicrobial compounds comprised within the antimicrobial composition is not a strong anionic compound.

In one embodiment the one or more antimicrobial compounds comprised within the antimicrobial composition is a small molecule.

In one embodiment the size of the one or more antimicrobial compounds is less than 1 kDa. In other embodiments the size of the antimicrobial compound is less than 900 Da, for example less than 800 Da, such as less than 700 Da, for example less than 600 Da, such as less than 500 Da, for example less than 400 Da, such as less than 300 Da, for example less than 200 Da, such as less than 100 Da.

In other embodiments, the size of the one or more antimicrobial compounds comprised within the antimicrobial composition is in the range of 100 Da-1 kDa, such as 100-200 Da, for example 200-300 Da, such as 300-400 Da, for example 400-500 Da, such as 500-600 Da, for example 700-800 Da, such as 800-900 Da, for example 900-1000 Da (1 kDa).

In other embodiments the size of the one or more antimicrobial compounds is close to 1 kDa, but not necessarily less than 1 kDa, for example less than 1.1 kDa, such as less than 1.2 kDa, for example less than 1.3 kDa, such as less than 1.4 kDa, for example less than 1.5 kDa, such as less than 1.6 kDa, for example less than 1.7 kDa, such as less than 1.8 kDa.

In one embodiment the antimicrobial composition comprises less that 20% (weight/weight %) protein, for example less than 10%, such as less than 8%, for example less than 6%, such as less 4%, for example less than 1%.

In one embodiment the antimicrobial composition comprises less that 20% (weight/weight %) ash, for example less than 10%, such as less than 8%, for example less than 6%, such as less 4%, for example less than 1%.

In one embodiment the antimicrobial composition comprises less that 20% (weight/weight %) lipid, for example less than 10%, such as less than 8%, for example less than 6%, such as less 4%, for example less than 1%.

In one embodiment the antimicrobial composition comprises less that 20% (weight/weight %) carbohydrate, for example less than 10%, such as less than 8%, for example less than 6%, such as less 4%, for example less than 1%.

Figure 12:
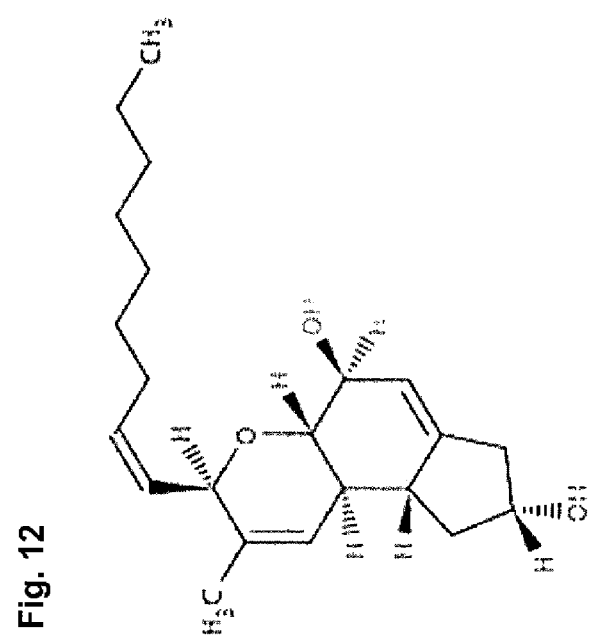
FIG. 12. The structure of penostatin with a mass=346 Da.

In one embodiment the antimicrobial composition comprises a compound with mass 346 and/or a m/z of 347 as depicted in FIG. 12.

Figure 8:
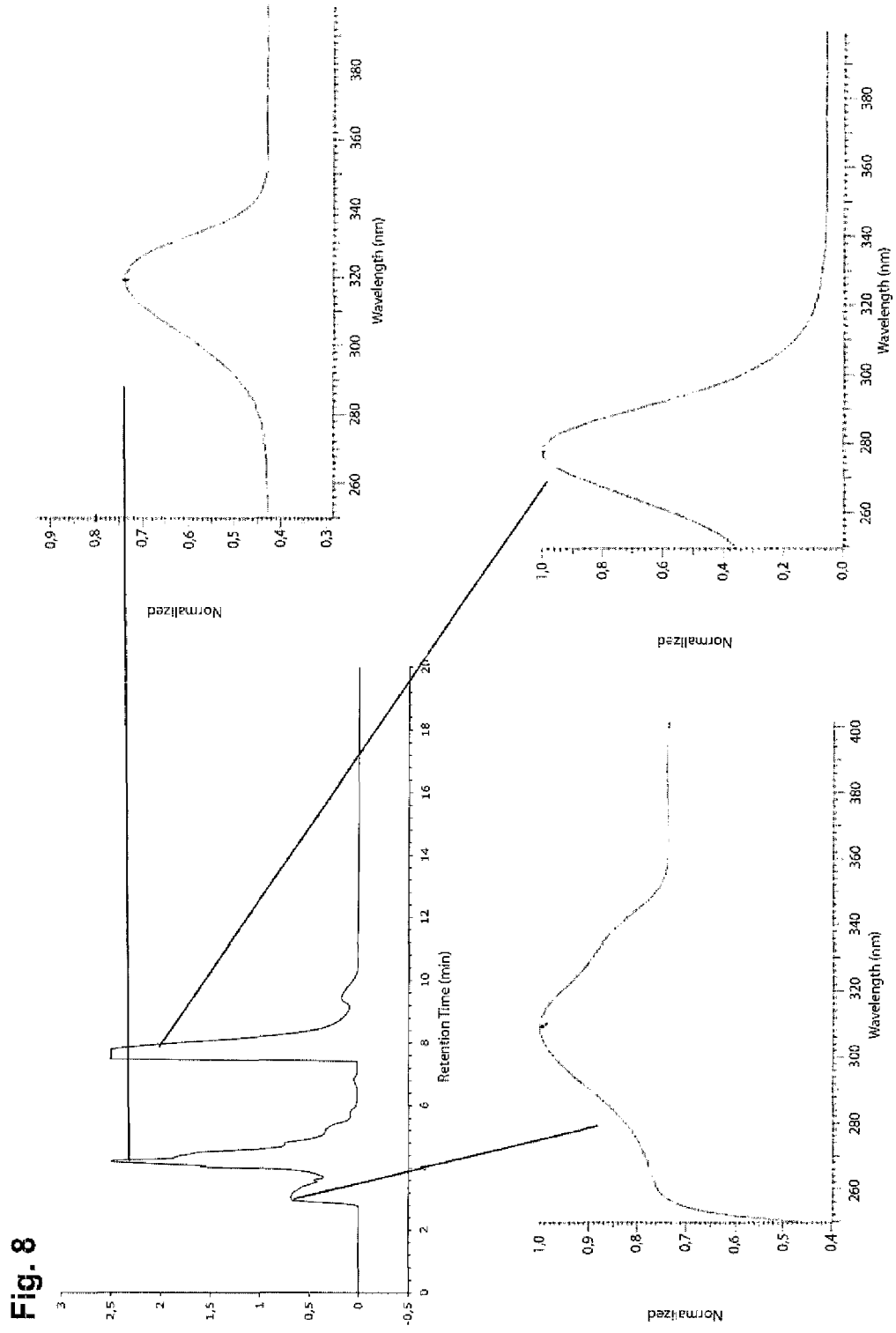
FIG. 8. UV-spectra of the various peaks from the normal phase chromatography shown in FIG. 7.

In one embodiment the antimicrobial composition comprises a compound with UV-spectra similar or identical to the UV spectra depicted in FIG. 8.

In one embodiment the antimicrobial composition comprises penostatin or a similar compound.

Secondary Metabolites

Secondary metabolites, also known as natural products, are those products (chemical compounds) of metabolism that are not essential for normal growth, development or reproduction of an organism. In this sense they are "secondary".

Secondary metabolites, including antibiotics, are produced in nature and serve survival functions for the organisms producing them. Secondary metabolites serve: (i) as competitive weapons used against bacteria, fungi, amoebae, plants, insects, and large animals; (ii) as metal transporting agents; (iii) as agents of symbiosis between microbes and plants, nematodes, insects, and higher animals; (iv) as sexual hormones; and (v) as differentiation effectors.

The function or importance of these compounds to the organism's development is usually of ecological nature as they are used as defence against predators (herbivores, pathogens etc.), for interspecies competition, and to facilitate the reproductive processes.

Contrary to primary metabolites these compounds are not ubiquitous in the living organisms who produce them nor are they necessarily expressed continuously. Although plants are better known as a source of secondary metabolites, bacteria, fungi and many marine organisms (sponges, tunicates, corals, snails) are very interesting sources, too.

Secondary metabolites can be classified by their chemical structure or physical properties into one or more of the following groups: alkaloids, terpenoids, polyketides, aliphatic, aromatic, and heteroaromatic organic acids, phenols, iridoids, steroids, saponins, peptides, ethereal oils, resins and balsams.

In one embodiment of the present invention at least one of the one or more antimicrobial compounds comprises or consists of a secondary metabolite such as one or more compounds selected from the group consisting of alkaloids, terpenoids, polyketides, aliphatic, aromatic, and heteroaromatic organic acids, phenols, iridoids, steroids, saponins, peptides, ethereal oils, resins and balsams.

Industrial Uses of the Antimicrobial Composition from *C. finmarchicus*

Antiseptics

In one embodiment the antimicrobial composition is an antiseptic. Antiseptics are antimicrobial substances that are applied to living tissue/skin to reduce the possibility of infection and/or sepsis, and/or putrefaction. Antiseptics are generally distinguished from antibiotics by their ability to be transported through the lymphatic system to destroy bacteria within the body, and from disinfectants, which destroy microorganisms found on non-living objects.

The microbial composition according to the present invention can be a true germicides, capable of destroying microbes (bacteriocidal), or bacteriostatic and only prevent or inhibit their growth. Antibacterials are antiseptics that have the proven ability to act against bacteria especially if they target systems which kill only bacteria. Microbicides which kill virus particles are called viricides or antivirals. The antimicrobial composition of the present invention can be a true germicide, an antibacterial, a microbicide, a viricide and/or an antiviral.

Disinfectant

In one embodiment the antimicrobial composition is a disinfectant. In one embodiment the antimicrobial composition can be used in cleaning of hospitals such as in cleaning of an operating room and/or surgery equipment.

Disinfectants should generally be distinguished from antibiotics that destroy microorganisms within the body, and from antiseptics, which destroy microorganisms on living tissue. Sanitizers are substances that reduce the number of microorganisms to a safe level. One official and legal definition states that a sanitizer must be capable of killing 99.999%, known as a 5 log reduction, of a specific bacterial test population, and to do so within 30 seconds. The main difference between a sanitizer and a disinfectant is that at a specified use dilution, the disinfectant must have a higher kill capability for pathogenic bacteria compared to that of a sanitizer. Very few disinfectants and sanitizers can sterilize (the complete elimination of all microorganisms), and those that can depend entirely on their mode of application. Bacterial endospores are most resistant to disinfectants, however some viruses and bacteria also possess some tolerance. The present invention relates in one embodiment to use of the antimicrobial composition as a sanitizer and/or a disinfectant.

Preservative

The invention also relates to the use of the antimicrobial composition as a preservative, such as in nutritional and/or pharmaceutical composition. A preservative is a natural or synthetic chemical that is added to products such as foods, pharmaceuticals, paints, biological samples, wood, etc. to prevent decomposition by microbial growth or by undesirable chemical changes.

An embodiment relates to the use of the antimicrobial composition as a preservative in a feed composition/food conservation.

Anti-Fouling

In one embodiment the antimicrobial composition is used for anti-fouling. Anti-fouling is the process of removing or inhibiting the accumulation of biofouling. Biofouling or biological fouling is the undesirable accumulation of microorganisms, plants, algae, and animals on surfaces such as submerged structures like ships' hulls.

The antimicrobial composition can be used for controlling, reducing and/or eliminating over time the number of undesirable microorganisms in a bio-film.

Biofouling is also found in membrane systems, such as membrane bioreactors and reverse osmosis spiral wound membranes. In the same manner it is found as fouling in cooling water cycles of large industrial equipments and power stations. Biofouling is divided into microfouling—biofilm formation and bacterial adhesion—and macrofouling—attachment of larger organisms, of which the main culprits are barnacles, mussels, polychaete worms, bryozoans, and seaweed. Together, these organisms form a fouling community.

Biofouling can occur on any surface submerged in water such as for example on ships. Other examples of surfaces that can be exposed to biofouling are any installations, membranes, nets, measuring equipment or other equipment in aquaculture.

Biofouling can also occur in groundwater wells where buildup can limit recovery flow rates, and in the exterior and interior of ocean-laying pipes. In the latter case it has been shown to retard the seawater flow through the pipe and has to be removed with the tube cleaning process.

In one preferred embodiment the surface for application of the anti-fouling composition is a surface that is at least occasionally immersed in water, wherein said water includes fresh, salt or brackish water. The surface can be selected from the group consisting of the surfaces of vessels including boats and ships, ship hulls, off-shore equipment, pipes, substructures of bridges, piers and aquacultural apparatuses including fish farming nets.

The methods and compositions disclosed herein may be used on a variety of surfaces, including but not limited to boat hulls, marine markers, bulkheads, pilings, water inlets, floors, roofs, and shingles. For example, the methods and compositions may be used to minimize fouling of marine markers. Such markers constitute a large category of floating objects and are greatly impaired by the accumulation of marine growth. Similarly, the methods and compositions may be used on marine bulkheads. The accumulation of marine growth on bulkhead structures is detrimental to the bulkhead structure over the long term. Furthermore, the growth causes significant short term effects that are aesthetically displeasing and dangerous. Moreover, the harsh abrasive characteristics of the hard growth can result in major damage to vessels. Similarly, the present invention can be used to minimize blockages due to fouling by marine growth of heat exchangers, evaporators, condensers and fire and flushing systems, thus resulting in significant decreases in maintenance costs for all categories of marine structures.

The antimicrobial composition can in one embodiment be included in a paint such as a paint for marine vessels. Paints according to the invention include the antimicrobial composition in an amount effective to reduce the growth of unwanted or undesirable microorganisms. Such compositions and/or paints may be in a variety of forms, including paints, lacquers, pastes, laminates, epoxies, resins, waxes, gels, and glues in addition to other forms known to one of skill in the art.

The antimicrobial composition according to the present invention can be used for prevention and/or inhibition of any type of fouling including the types mentioned above.

The antimicrobial composition can also be used for conservation of e.g. food/feed, drinks/beverages, pharmaceuticals and cosmetics.

Anti-Bacterial Effect

In another preferred embodiment the antimicrobial composition has an anti-bacterial effect. The antibacterial effect can in one embodiment be employed in food production such as in the dairy industry. In another embodiment the antimicrobial composition can be used in hospitals such as in an operating room.

In one embodiment the antimicrobial composition according to the present invention is a *C. finmarchicus* homogenate for use as a medicament.

In one embodiment the antimicrobial composition according to the present invention can be used for inhibition and/or prevention of growth of or more bacteria such as one or more bacteria selected from the group consisting of *Acetobacter aurantius, Acinetobacter* species: *Acinetobacter baumannii, Acinetobacter calcoaceticus, Acinetobacter johnsonii, Acinetobacter junii, Acinetobacter lwoffii, Acinetobacter radioresistens, Acinetobacter septicus, Acinetobacter schindleri, Acinetobacter ursingii; Actinomyces* species: *Actinomyces bovis, Actinomyces bowdenii, Actinomyces canis, Actinomyces cardiffensis, Actinomyces catuli, Actinomyces coleocanis, Actinomyces dentalis, Actinomyces denticolens, Actinomyces europaeus, Actinomyces funkei, Actinomyces*

*georgiae, Actinomyces gerencseriae, Actinomyces graevenitzii, Actinomyces hongkongensis, Actinomyces hordeovulneris, Actinomyces howellii, Actinomyces humiferus, Actinomyces hyovaginalis, Actinomyces israelii, Actinomyces marimammalium, Actinomyces meyeri, Actinomyces naeslundii, Actinomyces nasicola, Actinomyces neuii, Actinomyces odontolyticus, Actinomyces oricola, Actinomyces radicidentis, Actinomyces radingae, Actinomyces slackii, Actinomyces streptomycini, Actinomyces suimastitidis, Actinomyces suis, Actinomyces turicensis, Actinomyces urogenitalis, Actinomyces vaccimaxillae, Actinomyces viscosus; Actinobacillus* species: *Actinobacillus actinomycetemcomitans, Actinobacillus arthritidis, Actinobacillus capsulatus, Actinobacillus delphinicola, Actinobacillus equuli, Actinobacillus hominis, Actinobacillus indolicus, Actinobacillus lignieresii, Actinobacillus minor, Actinobacillus muris, Actinobacillus pleuropneumoniae, Actinobacillus porcinus, Actinobacillus rossii, Actinobacillus scotiae, Actinobacillus seminis, Actinobacillus succinogenes, Actinobacillus suis, Actinobacillus ureae; Aeromonas* species: *Aeromonas allosaccharophila, Aeromonas bestiarum, Aeromonas bivalvium, Aeromonas encheleia, Aeromonas enteropelogenes, Aeromonas euchrenophila, Aeromonas hydrophila, Aeromonas ichthiosmia, Aeromonas jandaei, Aeromonas media, Aeromonas molluscorum, Aeromonas popoffii, Aeromonas punctata, Aeromonas salmonicida, Aeromonas schubertii, Aeromonas sharmana, Aeromonas simiae, Aeromonas sobria, Aeromonas veronii; Afipia felis, Agrobacterium* species: *Agrobacterium radiobacter, Agrobacterium rhizogenes, Agrobacterium rubi, Agrobacterium tumefaciens; Agromonas* species, *Alcaligenes* species: *Alcaligenes aquatilis, Alcaligenes eutrophus, Alcaligenes faecalis, Alcaligenes latus, Alcaligenes xylosoxidans; Alishewanella* species, *Alterococcus* species, *Anaplasma phagocytophilum, Anaplasma marginale, Aquamonas* species, *Arcanobacterium haemolyticum, Aranicola* species, *Arsenophonus* species, *Azotivirga* species, *Azotobacter vinelandii, Azotobacter chroococcum*, Bacillary dysentery (Shigellosis), *Bacillus* species: *Bacillus abortus* (*Brucella melitensis* biovar *abortus*), *Bacillus anthracis* (Anthrax), *Bacillus brevis, Bacillus cereus, Bacillus coagulans, Bacillus fusiformis, Bacillus globigii, Bacillus licheniformis, Bacillus megaterium, Bacillus mycoides, Bacillus natto, Bacillus stearothermophilus, Bacillus subtilis, Bacillus sphaericus, Bacillus thuringiensis; Bacteroides* species: *Bacteroides forsythus* (*Tannerella forsythensis*), *Bacteroides acidifaciens, Bacteroides distasonis* (reclassified as *Parabacteroides distasonis*), *Bacteroides gingivalis, Bacteroides gracilis, Bacteroides fragilis, Bacteroides oris, Bacteroides ovatus, Bacteroides putredinis, Bacteroides pyogenes, Bacteroides stercoris, Bacteroides suis, Bacteroides tectus, Bacteroides thetaiotaomicron, Bacteroides vulgatus; Bartonella* species: *Bartonella alsatica, Bartonella bacilliformis, Bartonella birtlesii, Bartonella bovis, Bartonella capreoli, Bartonella clarridgeiae, Bartonella doshiae, Bartonella elizabethae, Bartonella grahamii, Bartonella henselae* (cat scratch fever), *Bartonella koehlerae, Bartonella muris, Bartonella peromysci, Bartonella quintana, Bartonella rochalimae, Bartonella schoenbuchii, Bartonella talpae, Bartonella taylorii, Bartonella tribocorum, Bartonella vinsonii* spp. *Arupensis, Bartonella vinsonii* spp. *Berkhoffii, Bartonella vinsonii* spp. *Vinsonii, Bartonella washoensis*; BCG (Bacille Calmette-Guerin), *Bergeyella zoohelcum* (*Weeksella zoohelcum*), *Bifidobacterium bifidum, Blastobacter* species, *Blochmannia* species, *Bordetella* species: *Bordetella ansorpii, Bordetella avium, Bordetella bronchiseptica, Bordetella hinzii, Bordetella holmesii, Bordetella parapertussis, Bordetella pertussis* (Whooping cough), *Bordetella petrii, Bordetella trematum; Borrelia* species: *Borrelia burgdorferi, Borrelia afzelii, Borrelia anserina, Borrelia garinii, Borrelia valaisiana, Borrelia hermsii, Borrelia Parkeri, Borrelia recurrentis; Bosea* species, *Bradyrhizobium* species, *Brenneria* species, *Brucella* species: *Brucella abortus, Brucella canis, Brucella melitensis, Brucella neotomae, Brucella ovis, Brucella suis, Brucella pinnipediae; Buchnera* species, *Budvicia* species, *Burkholderia* species: *Burkholderia cepacia* (*Pseudomonas cepacia*), *Burkholderia mallei* (*Pseudomonas mallei/Actinobacillus mallei*), *Burkholderia pseudomallei* (*Pseudomonas pseudomallei*); *Buttiauxella* species, *Calymmatobacterium granulomatis, Campylobacter* species: *Campylobacter coli, Campylobacter concisus, Campylobacter curvus, Campylobacter fetus, Campylobacter gracilis, Campylobacter helveticus, Campylobacter hominis, Campylobacter hyointestinalis, Campylobacter insulaenigrae, Campylobacter jejuni, Campylobacter lanienae, Campylobacter lari, Campylobacter mucosalis, Campylobacter rectus, Campylobacter showae, Campylobacter sputorum, Campylobacter upsaliensis; Capnocytophaga canimorsus* (*Dysgonic fermenter* type 2), *Corynebacterium* species, *Cardiobacterium hominis, Cedecea* species, *Chlamydia* species: *Chlamydia trachomatis* (Lymphogranuloma venereum), *Chlamydia muridarum, Chlamydia suis; Chlamydophila* species: *Chlamydophila pneumoniae, Chlamydophila psittaci* (Psittacosis), *Chlamydophila pecorum, Chlamydophila abortus, Chlamydophila felis, Chlamydophila caviae; Citrobacter* species: *Citrobacter amalonaticus, Citrobacter braakii, Citrobacter farmeri, Citrobacter freundii, Citrobacter gillenii, Citrobacter intermedius, Citrobacter koseri* aka *Citrobacter diversus, Citrobacter murliniae, Citrobacter rodentium, Citrobacter sedlakii, Citrobacter werkmanii, Citrobacter youngae; Clostridium* species: *Clostridium botulinum, Clostridium difficile, Clostridium novyi, Clostridium septicum, Clostridium tetani* (Tetanus), *Clostridium welchii* (*Clostridium perfringens*); *Corynebacterium* species: *Corynebacterium diphtheriae* (Diphtheria), *Corynebacterium amycolatum, Corynebacterium aquaticum, Corynebacterium bovis, Corynebacterium equi, Corynebacterium flavescens, Corynebacterium glutamicum, Corynebacterium haemolyticum, Corynebacterium jeikeiun* (corynebacteria of group JK), *Corynebacterium minutissimum* (Erythrasma), *Corynebacterium parvum* (also called *Propionibacterium acnes*), *Corynebacterium pseudodiptheriticum* (also called *Corynebacterium hofmannii*), *Corynebacterium pseudotuberculosis* (also called *Corynebacterium ovis*), *Corynebacterium pyogenes, Corynebacterium urealyticum* (corynebacteria of group D2), *Corynebacterium renale, Corynebacterium striatum, Corynebacterium tenuis* (*Trichomycosis palmellina, Trichomycosis axillaris*), *Corynebacterium ulcerans, Corynebacterium xerosis; Coxiella burnetii* (Q fever), *Cronobacter* species: *Cronobacter sakazakii, Cronobacter malonaticus, Cronobacter turicensis, Cronobacter muytjensii, Cronobacter dublinensis; Delftia acidovorans* (*Comamonas acidovorans*), *Dickeya* species, *Edwardsiella* species, *Eikenella corrodens, Enterobacter* species: *Enterobacter aerogenes, Enterobacter cloacae, Enterobacter sakazakii; Enterococcus* species: *Enterococcus avium, Enterococcus durans, Enterococcus faecalis* (*Streptococcus faecalis/Streptococcus* Group D), *Enterococcus faecium, Enterococcus solitarius, Enterococcus galllinarum, Enterococcus maloratus; Ehrlichia chaffeensis, Erysipelothrix rhusiopathiae, Erwinia* species, *Escherichia* species: *Escherichia adecarboxylata, Escherichia albertii, Escherichia blattae, Escherichia coli, Escherichia fergusonii, Escherichia hermannii, Escherichia vulneris; Ewingella* species, *Flavobacterium* species:

*Flavobacterium aquatile, Flavobacterium branchiophilum, Flavobacterium columnare, Flavobacterium flevense, Flavobacterium gondwanense, Flavobacterium hydatis, Flavobacterium johnsoniae, Flavobacterium pectinovorum, Flavobacterium psychrophilum, Flavobacterium saccharophilum, Flavobacterium salegens, Flavobacterium scophthalmum, Flavobacterium succinans; Francisella tularensis* (Tularaemia), *Francisella novicida, Francisella philomiragia, Fusobacterium* species: *Fusobacterium necrophorum* (Lemierre syndrome/*Sphaerophorus necrophorus*), *Fusobacterium nucleatum, Fusobacterium polymorphum, Fusobacterium novum, Fusobacterium mortiferum, Fusobacterium varium; Gardnerella vaginalis, Gemella haemolysans, Gemella morbillorum* (*Streptococcus morbillorum*), *Grimontella* species, *Haemophilus* species: *Haemophilus aegyptius* (Koch-Weeks bacillus), *Haemophilus aphrophilus, Haemophilus avium, Haemophilus ducreyi* (Chancroid), *Haemophilus felis, Haemophilus haemolyticus, Haemophilus influenzae* (Pfeiffer bacillus), *Haemophilus paracuniculus, Haemophilus parahaemolyticus, Haemophilus parainfluenzae, Haemophilus paraphrophilus* (*Aggregatibacter aphrophilus*), *Haemophilus pertussis, Haemophilus pittmaniae, Haemophilus somnus, Haemophilus vaginalis; Hafnia* species, *Hafnia alvei, Helicobacter* species: *Helicobacter acinonychis, Helicobacter anseris, Helicobacter aurati, Helicobacter bilis, Helicobacter bizzozeronii, Helicobacter brantae, Helicobacter Canadensis, Helicobacter canis, Helicobacter cholecystus, Helicobacter cinaedi, Helicobacter cynogastricus, Helicobacter felis, Helicobacter fennelliae, Helicobacter ganmani, Helicobacter heilmannii* (*Gastrospirillum hominis*), *Helicobacter hepaticus, Helicobacter mesocricetorum, Helicobacter marmotae, Helicobacter muridarum, Helicobacter mustelae, Helicobacter pametensis, Helicobacter pullorum, Helicobacter pylori* (stomach ulcer), *Helicobacter rappini, Helicobacter rodentium, Helicobacter salomonis, Helicobacter trogontum, Helicobacter typhlonius, Helicobacter winghamensis*; Human granulocytic ehrlichiosis (*Anaplasma phagocytophilum/Ehrlichia phagocytophila*), Human monocytotropic ehrlichiosis (Monocytic ehrlichiosis/*Ehrlichia chaffeensis*), *Klebsiella* species: *Klebsiella granulomatis* (*Calymmatobacterium granulomatis*), *Klebsiella mobilis, Klebsiella ornithinolytica, Klebsiella oxytoca, Klebsiella ozaenae, Klebsiella planticola, Klebsiella pneumoniae, Klebsiella rhinoscleromatis, Klebsiella singaporensis, Klebsiella terrigena, Klebsiella trevisanii, Klebsiella variicola; Kingella kingae, Kluyvera* species, *Lactobacillus* species: *Lactobacillus acetotolerans, Lactobacillus acidifarinae, Lactobacillus acidipiscis, Lactobacillus acidophilus* (*Doderlein bacillus*), *Lactobacillus agilis, Lactobacillus algidus, Lactobacillus alimentarius, Lactobacillus amylolyticus, Lactobacillus amylophilus, Lactobacillus amylotrophicus, Lactobacillus amylovorus, Lactobacillus animalis, Lactobacillus antri, Lactobacillus apodemi, Lactobacillus aviarius, Lactobacillus bifermentans, Lactobacillus brevis, Lactobacillus buchneri, Lactobacillus camelliae, Lactobacillus casei, Lactobacillus catenaformis, Lactobacillus ceti, Lactobacillus coleohominis, Lactobacillus collinoides, Lactobacillus composti, Lactobacillus concavus, Lactobacillus coryniformis, Lactobacillus crispatus, Lactobacillus crustorum, Lactobacillus curvatus, Lactobacillus delbrueckii, Lactobacillus delbrueckii* subsp. *Bulgaricus, Lactobacillus delbrueckii* subsp. *Lactis, Lactobacillus diolivorans, Lactobacillus equi, Lactobacillus equigenerosi, Lactobacillus farraginis, Lactobacillus farciminis, Lactobacillus fermentum, Lactobacillus formicalis, Lactobacillus fructivorans, Lactobacillus frumenti, Lactobacillus fuchuensis, Lactobacillus gallinarum, Lactobacillus gasseri, Lactobacillus gastricus, Lactobacillus ghanensis, Lactobacillus graminis, Lactobacillus hammesii, Lactobacillus hamsteri, Lactobacillus harbinensis, Lactobacillus hayakitensis, Lactobacillus helveticus, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kefuranofaciens, Lactobacillus kefiri, Lactobacillus kimchii, Lactobacillus kitasatonis, Lactobacillus kunkeei, Lactobacillus leichmannii, Lactobacillus lindneri, Lactobacillus malefermentans, Lactobacillus mali, Lactobacillus manihotivorans, Lactobacillus mindensis, Lactobacillus mucosae, Lactobacillus murinus, Lactobacillus nagelii, Lactobacillus namurensis, Lactobacillus nantensis, Lactobacillus oligofermentans, Lactobacillus oris, Lactobacillus panis, Lactobacillus pantheris, Lactobacillus parabrevis, Lactobacillus parabuchneri, Lactobacillus paracollinoides, Lactobacillus parafarraginis, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus rennini, Lactobacillus reuteri, Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae, Lactobacillus zymae; Leclercia* species, *Legionella* species: *Legionella adelaidensis, Legionella anisa, Legionella beliardensis, Legionella birminghamensis, Legionella bozemanii, Legionella brunensis, Legionella busanensis, Legionella cherrii, Legionella cincinnatiensis, Legionella donaldsonii, Legionella drancourtii, Legionella drozanskii, Legionella erythra, Legionella fairfieldensis, Legionella fallonii, Legionella feeleii, Legionella geestiana, Legionella genomospecies, Legionella gratiana, Legionella gresilensis, Legionella hackeliae, Legionella impletisoli, Legionella israelensis, Legionella jamestowniensis,* 'Candidatus *Legionella jeonii', Legionella jordanis, Legionella lansingensis, Legionella londiniensis, Legionella longbeachae, Legionella lytica, Legionella maceachernii, Legionella micdadei, Legionella moravica, Legionella nautarum, Legionella oakridgensis, Legionella parisiensis, Legionella pneumophila, Legionella quateirensis, Legionella quinlivanii, Legionella rowbothamii, Legionella rubrilucens, Legionella sainthelensi, Legionella santicrucis, Legionella shakespearei, Legionella spiritensis, Legionella steigerwaltii, Legionella taurinensis, Legionella tucsonensis, Legionella wadsworthii, Legionella waltersii, Legionella worsleiensis, Legionella yabuuchiae; Leminorella* species, *Leptospira* species: *Leptospira interrogans, Leptospira kirschneri, Leptospira noguchii, Leptospira alexanderi, Leptospira weilii, Leptospira* genomospecies 1, *Leptospira borgpetersenii, Leptospira santarosai, Leptospira inadai, Leptospira fainei, Leptospira broomii, Leptospira licerasiae, Leptospira biflexa, Leptospira meyeri, Leptospira wolbachii, Leptospira* genomospecies 3, *Leptospira* genomospecies 4, *Leptospira* genomospecies 5; Lepromatous leprosy (Danielssen-Boeck disease), *Leptospira canicola, Leptospira hebdomadis,* Leptospirosis (Weil disease/*Leptospira icterohaemorrhagiae/Leptospira interrogans* serovar *icterohaemorrhagiae*), *Leptotrichia, Leuconostoc* species:

*Leuconostoc carnosum, Leuconostoc citreum, Leuconostoc durionis, Leuconostoc fallax, Leuconostoc ficulneum, Leuconostoc fructosum, Leuconostoc garlicum, Leuconostoc gasicomitatum, Leuconostoc gelidum, Leuconostoc inhae, Leuconostoc kimchii, Leuconostoc lactis, Leuconostoc mesenteroides, Leuconostoc pseudoficulneum, Leuconostoc pseudomesenteroides; Listeria* species: *Listeria grayi, Listeria innocua, Listeria ivanovii, Listeria monocytogenes* (Listeriosis), *Listeria seeligeri, Listeria welshimeri; Methanobacterium extroquens, Microbacterium multiforme, Micrococcus* species: *Micrococcus antarcticus, Micrococcus flavus, Micrococcus luteus, Micrococcus lylae, Micrococcus mucilaginosis, Micrococcus roseus, Micrococcus sedentarius; Mobiluncus, Moellerella* species, *Morganella* species, *Moraxella* species: *Moraxella atlantae, Moraxella boevrei, Moraxella bovis, Moraxella canis, Moraxella caprae, Moraxella catarrhalis* (*Branhamella catarrhalis*), *Moraxella caviae, Moraxella cuniculi, Moraxella equi, Moraxella lacunata, Moraxella lincolnii, Moraxella nonliquefaciens, Moraxella oblonga, Moraxella osloensis, Moraxella saccharolytica; Morganella morganii, Mycobacterium* species: *Mycobacterium abscessus, Mycobacterium africanum, Mycobacterium agri, Mycobacterium aichiense, Mycobacterium alvei, Mycobacterium arupense, Mycobacterium asiaticum, Mycobacterium aubagnense, Mycobacterium aurum, Mycobacterium austroafricanum, Mycobacterium avium* (Battey disease/Lady Windermere syndrome), *Mycobacterium avium paratuberculosis* (implicated in Crohn's disease in humans and Johne's disease in sheep), *Mycobacterium avium silvaticum, Mycobacterium avium "hominissuis", Mycobacterium colombiense, Mycobacterium boenickei, Mycobacterium bohemicum, Mycobacterium bolletii, Mycobacterium botniense, Mycobacterium bovis* (Bovine tuberculosis), *Mycobacterium branderi, Mycobacterium brisbanense, Mycobacterium brumae, Mycobacterium canariasense, Mycobacterium caprae, Mycobacterium celatum, Mycobacterium chelonae, Mycobacterium chimaera, Mycobacterium chitae, Mycobacterium chlorophenolicum, Mycobacterium chubuense, Mycobacterium conceptionense, Mycobacterium confluentis, Mycobacterium conspicuum, Mycobacterium cookii, Mycobacterium cosmeticum, Mycobacterium diernhoferi, Mycobacterium doricum, Mycobacterium duvalii, Mycobacterium elephantis, Mycobacterium fallax, Mycobacterium farcinogenes, Mycobacterium flavescens, Mycobacterium florentinum, Mycobacterium fluoroanthenivorans, Mycobacterium fortuitum, Mycobacterium fortuitum* subsp. *Acetamidolyticum, Mycobacterium frederiksbergense, Mycobacterium gadium, Mycobacterium gastri, Mycobacterium genavense, Mycobacterium gilvum, Mycobacterium goodii, Mycobacterium gordonae* (*Mycobacterium aquae*), *Mycobacterium haemophilum, Mycobacterium hassiacum, Mycobacterium heckeshornense, Mycobacterium heidelbergense, Mycobacterium hiberniae, Mycobacterium hodleri, Mycobacterium holsaticum, Mycobacterium houstonense, Mycobacterium immunogenum, Mycobacterium interjectum, Mycobacterium intermedium, Mycobacterium intracellulare, Mycobacterium kansasii, Mycobacterium komossense, Mycobacterium kubicae, Mycobacterium kumamotonense, Mycobacterium lacus, Mycobacterium lentiflavum, Mycobacterium leprae* (causes leprosy or Hansen disease/Hanseniasis), *Mycobacterium lepraemurium, Mycobacterium madagascariense, Mycobacterium mageritense, Mycobacterium malmoense, Mycobacterium marinum* (Fish tank granuloma), *Mycobacterium massiliense, Mycobacterium microti, Mycobacterium monacense, Mycobacterium montefiorense, Mycobacterium moriokaense, Mycobacterium mucogenicum, Mycobacterium murale, Mycobacterium nebraskense, Mycobacterium neoaurum, Mycobacterium neworleansense, Mycobacterium nonchromogenicum, Mycobacterium novocastrense, Mycobacterium obuense, Mycobacterium palustre, Mycobacterium parafortuitum, Mycobacterium parascrofulaceum, Mycobacterium parmense, Mycobacterium peregrinum, Mycobacterium phlei, Mycobacterium phocaicum, Mycobacterium pinnipedii, Mycobacterium porcinum, Mycobacterium poriferae, Mycobacterium pseudoshottsii, Mycobacterium pulveris, Mycobacterium psychrotolerans, Mycobacterium pyrenivorans, Mycobacterium rhodesiae, Mycobacterium saskatchewanense, Mycobacterium scrofulaceum, Mycobacterium senegalense, Mycobacterium seoulense, Mycobacterium septicum, Mycobacterium shimoidei, Mycobacterium shottsii, Mycobacterium simiae, Mycobacterium smegmatis, Mycobacterium sphagni, Mycobacterium szulgai, Mycobacterium terrae, Mycobacterium thermoresistibile, Mycobacterium tokaiense, Mycobacterium triplex, Mycobacterium triviale, Mycobacterium tuberculosis* (major cause of human tuberculosis), *Mycobacterium bovis, Mycobacterium africanum, Mycobacterium canetti, Mycobacterium caprae, Mycobacterium pinnipedii', Mycobacterium tusciae, Mycobacterium ulcerans* (causes Bairnsdale ulcer/Buruli ulcer), *Mycobacterium vaccae, Mycobacterium vanbaalenii, Mycobacterium wolinskyi, Mycobacterium xenopi; Mycoplasma* species: *Mycoplasma fermentans, Mycoplasma genitalium, Mycoplasma hominis, Mycoplasma penetrans, Mycoplasma phocacerebrale, Mycoplasma pneumoniae,* Nanukayami (Seven-day fever/Gikiyami), *Neisseria* species: *Neisseria gonorrhoea* (Gonococcus/Gonorrhea), *Neisseria meningitis* (Meningococcus), *Neisseria sicca, Neisseria cinerea, Neisseria elongata, Neisseria flavescens, Neisseria lactamica, Neisseria mucosa, Neisseria polysaccharea, Neisseria subflava; Nitrobacter* species, *Nocardia* species: *Nocardia asteroides, Nocardia brasiliensis, Nocardia caviae*; Noma (cancrum oris/gangrenous stomatitis), *Obesumbacterium, Oligotropha* species, *Orientia tsutsugamushi* (Scrub typhus), *Oxalobacter formigenes, Pantoea* species: *Pantoea agglomerans, Pantoea ananatis, Pantoea citrea, Pantoea dispersa, Pantoea punctata, Pantoea stewartii, Pantoea terrea; Pasteurella* species: *Pasteurella aerogenes, Pasteurella anatis, Pasteurella avium, Pasteurella bettyae, Pasteurella caballi, Pasteurella canis, Pasteurella dagmatis, Pasteurella gallicida, Pasteurella gallinarum, Pasteurella granulomatis, Pasteurella langaaensis, Pasteurella lymphangitidis, Pasteurella mairii, Pasteurella multocida, Pasteurella pneumotropica, Pasteurella skyensis, Pasteurella stomatis, Pasteurella testudinis, Pasteurella trehalosi, Pasteurella tularensis, Pasteurella ureae, Pasteurella volantium; Pediococcus* species: *Pediococcus acidilactici, Pediococcus cellicola, Pediococcus claussenii, Pediococcus damnosus, Pediococcus dextrinicus, Pediococcus ethanolidurans, Pediococcus inopinatus, Pediococcus parvulus, Pediococcus pentosaceus, Pediococcus stilesii; Peptostreptococcus* species: *Peptostreptococcus anaerobius, Peptostreptococcus asaccharolyticus, Peptostreptococcus harei, Peptostreptococcus hydrogenalis, Peptostreptococcus indoliticus, Peptostreptococcus ivorii, Peptostreptococcus lacrimalis, Peptostreptococcus lactolyticus, Peptostreptococcus magnus, Peptostreptococcus micros, Peptostreptococcus octavius, Peptostreptococcus prevotii, Peptostreptococcus tetradius, Peptostreptococcus vaginalis; Photorhabdus* species, *Photorhizobium* species, *Plesiomonas shigelloides, Porphyromonas gingivalis, Pragia* species, *Prevotella, Propionibacterium* species: *Propionibacterium acnes, Propionibacterium propionicus; Proteus* species: *Proteus mirabilis, Proteus morganii, Proteus penneri, Proteus rettgeri, Proteus vulgaris; Providencia* species: *Providencia friedericiana, Providencia stuartii; Pseudomonas* species:

Pseudomonas aeruginosa, Pseudomonas alcaligenes, Pseudomonas anguilliseptica, Pseudomonas argentinensis, Pseudomonas borbori, Pseudomonas citronellolis, Pseudomonas flavescens, Pseudomonas mendocina, Pseudomonas nitroreducens, Pseudomonas oleovorans, Pseudomonas pseudoalcaligenes, Pseudomonas resinovorans, Pseudomonas straminea, Pseudomonas aurantiaca, Pseudomonas aureofaciens, Pseudomonas chlororaphis, Pseudomonas fragi, Pseudomonas lundensis, Pseudomonas taetrolens, Pseudomonas Antarctica, Pseudomonas azotoformans, Pseudomonas brassicacearum, Pseudomonas brenneri, Pseudomonas cedrina, Pseudomonas corrugate, Pseudomonas fluorescens, Pseudomonas gessardii, Pseudomonas libanensis, Pseudomonas mandelii, Pseudomonas marginalis, Pseudomonas mediterranea, Pseudomonas meridiana, Pseudomonas migulae, Pseudomonas mucidolens, Pseudomonas orientalis, Pseudomonas panacis, Pseudomonas proteolytica, Pseudomonas rhodesiae, Pseudomonas synxantha, Pseudomonas thivervalensis, Pseudomonas tolaasii, Pseudomonas veronii, Pseudomonas denitrificans, Pseudomonas pertucinogena, Pseudomonas cremoricolorata, Pseudomonas fulva, Pseudomonas monteilii, Pseudomonas mosselii, Pseudomonas oryzihabitans, Pseudomonas parafulva, Pseudomonas plecoglossicida, Pseudomonas putida, Pseudomonas balearica, Pseudomonas luteola, Pseudomonas stutzeri, Pseudomonas amygdale, Pseudomonas avellanae, Pseudomonas caricapapayae, Pseudomonas cichorii, Pseudomonas coronafaciens, Pseudomonas ficuserectae, Pseudomonas meliae, Pseudomonas savastanoi, Pseudomonas syringae, Pseudomonas viridiflava, Pseudomonas abietaniphila, Pseudomonas acidophila, Pseudomonas agarici, Pseudomonas alcaliphila, Pseudomonas alkanolytica, Pseudomonas amyloderamosa, Pseudomonas asplenii, Pseudomonas azotifigens, Pseudomonas cannabina, Pseudomonas coenobios, Pseudomonas congelans, Pseudomonas costantinii, Pseudomonas cruciviae, Pseudomonas delhiensis, Pseudomonas excibis, Pseudomonas extremorientalis, Pseudomonas frederiksbergensis, Pseudomonas fuscovaginae, Pseudomonas gelidicola, Pseudomonas grimontii, Pseudomonas indica, Pseudomonas jessenii, Pseudomonas jinjuensis, Pseudomonas kilonensis, Pseudomonas knackmussii, Pseudomonas koreensis, Pseudomonas lini, Pseudomonas lutea, Pseudomonas moraviensis, Pseudomonas otitidis, Pseudomonas pachastrellae, Pseudomonas palleroniana, Pseudomonas papaveris, Pseudomonas peli, Pseudomonas perolens, Pseudomonas poae, Pseudomonas pohangensis, Pseudomonas psychrophila, Pseudomonas psychrotolerans, Pseudomonas rathonis, Pseudomonas reptilivora, Pseudomonas resiniphila, Pseudomonas rhizosphaerae, Pseudomonas rubescens, Pseudomonas salomonii, Pseudomonas segitis, Pseudomonas septica, Pseudomonas simiae, Pseudomonas suis, Pseudomonas thermotolerans, Pseudomonas tremae, Pseudomonas trivialis, Pseudomonas turbinellae, Pseudomonas tuticorinensis, Pseudomonas umsongensis, Pseudomonas vancouverensis, Pseudomonas vranovensis, Pseudomonas xanthomarina; Rahnella species, Ralstonia species: Ralstonia basilensis, Ralstonia campinensis, Ralstonia eutropha, Ralstonia gilardii, Ralstonia insidiosa, Ralstonia mannitolilytica, Ralstonia metallidurans, Ralstonia paucula, Ralstonia pickettii, Ralstonia respiraculi, Ralstonia solanacearum, Ralstonia syzygii, Ralstonia taiwanensis; Raoultella species, Rhodoblastus species, Rhodopseudomonas species, Rhinoscleroma, Rhizobium radiobacter, Rhodococcus equi, Rickettsia species: Rickettsia africae, Rickettsia akari, Rickettsia australis, Rickettsia conorii, Rickettsia felis, Rickettsia japonica, Rickettsia mooseri, Rickettsia prowazekii (Typhus fever), Rickettsia rickettsii, Rickettsia siberica, Rickettsia typhi, Rickettsia conorii, Rickettsia africae, Rickettsia psittaci, Rickettsia quintana, Rickettsia rickettsii, Rickettsia trachomae; Rothia dentocariosa, Salmonella species: Salmonella arizonae, Salmonella Bongori, Salmonella enterica, Salmonella enteriditis, Salmonella paratyphi, Salmonella typhi (Typhoid fever), Salmonella typhimurium, Salmonella salamae, Salmonella arizonae, Salmonella diarizonae, Salmonella houtenae, Salmonella indica; Samsonia species, Serratia species: Serratia entomophila, Serratia ficaria, Serratia fonticola, Serratia grimesii, Serratia liquefaciens, Serratia marcescens, Serratia odoriferae, Serratia plymuthica, Serratia proteamaculans, Serratia quinivorans, Serratia rubidaea, Serratia ureilytica; Shewanella putrefaciens, Shigella boydii, Shigella dysenteriae, Shigella flexneri, Shigella sonnei, Sodalis species, Spirillum species: Spirillum minus rat bite fever, Staphylococcus species: Staphylococcus aureus, Staphylococcus auricularis, Staphylococcus capitis, Staphylococcus caprae, Staphylococcus cohnii, Staphylococcus epidermidis, Staphylococcus felis, Staphylococcus haemolyticus, Staphylococcus hominis, Staphylococcus intermedius, Staphylococcus lugdunensis, Staphylococcus pettenkoferi, Staphylococcus saprophyticus, Staphylococcus schleiferi, Staphylococcus simulans, Staphylococcus vitulus, Staphylococcus warneri, Staphylococcus xylosus; Stenotrophomonas species: Stenotrophomonas acidaminiphila, Stenotrophomonas dokdonensis, Stenotrophomonas koreensis, Stenotrophomonas maltophilia, Stenotrophomonas nitritireducens, Stenotrophomonas rhizophila; Streptobacillus species: Streptobacillus moniliformis (Streptobacillary rat bite fever); Streptococcus species: Streptococcus Group A, Streptococcus Group B, Streptococcus agalactiae, Streptococcus aginosus, Streptococcus avium, Streptococcus bovis, Streptococcus canis, Streptococcus cricetus, Streptococcus faecium, Streptococcus faecalis, Streptococcus ferus, Streptococcus gallinarum, Streptococcus lactis, Streptococcus milleri, Streptococcus mitior, Streptococcus mitis, Streptococcus mutans, Streptococcus oralis, Streptococcus peroris, Streptococcus pneumoniae, Streptococcus pyogenes, Streptococcus ratti, Streptococcus salivarius, Streptococcus sanguinis, Streptococcus sobrinus, Streptococcus parasanguinis, Streptococcus suis, Streptococcus thermophilus, Streptococcus vestibularis, Streptococcus viridans, Streptococcus uberis, Streptococcus zooepidemicus; Tatumella species, Trabulsiella species, Treponema species: Treponema carateum (Pinta), Treponema denticola, Treponema endemicum (Bejel), Treponema pallidum (Syphilis), Treponema pertenue (Yaws); Tropheryma whipplei (Whipple disease), Tuberculoid leprosy, Ureaplasma urealyticum, Veillonella, Vibrio species: Vibrio aerogenes, Vibrio aestuarianus, Vibrio agarivorans, Vibrio albensis, Vibrio alginolyticus, Vibrio brasiliensis, Vibrio calviensis, Vibrio campbellii, Vibrio chagasii, Vibrio cholerae (Cholera), Vibrio cincinnatiensis, Vibrio Comma, Vibrio coralliilyticus, Vibrio crassostreae, Vibrio cyclitrophicus, Vibrio diabolicus, Vibrio diazotrophicus, Vibrio ezurae, Vibrio fischeri, Vibrio fluvialis, Vibrio fortis, Vibrio furnissii, Vibrio gallicus, Vibrio gazogenes, Vibrio gigantis, Vibrio halioticoli, Vibrio harveyi, Vibrio hepatarius, Vibrio hispanicus, Vibrio ichthyoenteri, Vibrio kanaloae, Vibrio lentus, Vibrio litoralis, Vibrio logei, Vibrio mediterranei, Vibrio metschnikovii, Vibrio mimicus, Vibrio mytili, Vibrio natriegens, Vibrio navarrensis, Vibrio neonatus, Vibrio neptunius, Vibrio nereis, Vibrio nigripulchritudo, Vibrio ordalii, Vibrio orientalis, Vibrio pacinii, Vibrio parahaemolyticus, Vibrio pectenicida, Vibrio penaeicida, Vibrio pomeroyi, Vibrio ponticus, Vibrio proteolyticus,

*Vibrio rotiferianus, Vibrio ruber, Vibrio rumoiensis, Vibrio salmonicida, Vibrio scophthalmi, Vibrio splendidus, Vibrio superstes, Vibrio tapetis, Vibrio tasmaniensis, Vibrio tubiashii, Vibrio vulnificus, Vibrio wodanis, Vibrio xuii; Vogesella indigofera, Wigglesworthia* species, *Wolbachia* species, *Xenorhabdus* species, *Yersinia enterocolitica, Yersinia pestis, Yersinia pseudotuberculosis*, and *Yokenella* species.

Antiviral Effects

In one embodiment the antimicrobial composition according to the present invention can be used for inhibition and/or prevention of growth of or more vira such as one or more vira selected from the group consisting of Abelson murine leukemia virus (Ab-MLV, A-MuLV), acute laryngotracheobronchitis virus (or HPIV), Adelaide River virus, Adeno-associated virus group (Dependevirus), Adenovirus, African horse sickness virus, African swine fever virus, AIDS virus, Aleutian mink disease, parvovirus, alfalfa mosaic virus, Alphaherpesvirinae (including HSV 1 and 2 and varicella), Alpharetrovirus (Avian leukosis virus, Rous sarcoma virus), Alphavirus, alkhurma virus, ALV related virus, Amapari virus, Andean potato mottle virus, Aphthovirus, Aquareovirus, arbovirus, arbovirus C, arbovirus group A, arbovirus group B, Arenavirus group, Argentine hemorrhagic fever virus, Argentinian hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, Avian leukosis virus (ALV), avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus (Cercopithecine herpesvirus 1), B19 virus (Parvovirus B19), Babanki virus, baboon herpesvirus, bacterial virus, baculovirus, barley yellow dwarf virus, Barmah Forest virus, bean pod mottle virus, bean rugose mosaic virus, Bebaru virus, Berrimah virus, Betaherpesvirinae, betaretrovirus, Bird flu, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, bracovirus, broad bean mottle virus, broad bean stain virus, brome mosaic virus, Bromovirus, Buggy Creek virus, bullet shaped virus group, Bunyamwera virus, Bunyavirus, Burkitt's lymphoma virus, Bwamba Fever, Bwattany hetero virus, CA virus (Croup-associated virus/parainfluenza vius type 2), Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, Capillovirus, caprine arthritis virus, caprine encephalitis virus, Caprine Herpes Virus, Capripox virus, Cardiovirus, Carlavirus, Carmovirus, carrot mottle virus, Cassia yellow blotch virus, Caulimovirus, Cauliflower mosaic virus, caviid herpesvirus 1, Cercopithecine herpesvirus 1, Cercopithecine herpesvirus 2, cereal yellow dwarf virus, Chandipura virus, Changuinola virus, channel catfish virus, Charleville virus, chickenpox virus, Chikungunya virus, chimpanzee herpesvirus, Chordopoxyirinae, chub reovirus, chum salmon virus, Closterovirus, Cocal virus, Coho salmon reovirus, coital exanthema virus, Colorado tick fever virus, Coltivirus Columbia SK virus, Commelina yellow mottle virus, Common cold virus, Comovirus, Condylomata accuminata, congenital cytomegalovirus, contagious eethyma virus, contagious pustular dermatitis virus, Coronavirus, Corriparta virus, coryza virus, cowpea chlorotic mottle virus, cowpea mosaic virus, cowpea virus, cowpox virus, coxsackie virus, CPV (cytoplasmic polyhedrosis virus), cricket paralysis virus, Crimean-Congo hemorrhagic fever virus, croup associated virus, Crypotovirus, Cucumovirus, Cypovirus, Cytomegalovirus (HCMV or Human Herpesvirus 5 HHV-5), cytoplasmic polyhedrosis virus, Cytorhabdovirus, deer papillomavirus, Deltaretrovirus (Human T-lymphotropic virus), Deformed wing virus DWV, Dengue, Densovirus, Dependovirus, Dhori virus, Dianthovirus, diplorna virus, DNA virus, Dobrava-Belgrade Virus, Dog Flu, *Drosophila* C virus, duck hepatitis B virus, duck hepatitis virus 1, duck hepatitis virus 2, duovirus, Duvenhage virus, eastern equine encephalitis virus, eastern equine encephalomyelitis virus, Ebola virus, Ebola-like virus, Echovirus, echovirus 10, echovirus 28, echovirus 9, ectromelia virus, EEE virus (Eastern equine encephalitis virus), EIA virus (equine infectious anemia), EMC virus (Encephalomyocarditis), *Emiliania huxleyi* virus 86, encephalitis virus, encephalomyocarditis virus, Endogenous retrovirus, Enterovirus, Entomopoxyirinae, Entomopoxvirus A, Entomopoxvirus B, Entomopoxvirus C, enzyme elevating virus, epidemic hemorrhagic fever virus, epizootic hemorrhagic disease virus, Epsilonretrovirus, Epstein-Barr virus (EBV; Human herpesvirus 4 HHV-4), equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, Fabavirus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Fijivirus, Filovirus, Flanders virus, Flavivirus, foot and mouth disease virus, Fort Morgan virus, Four Corners hantavirus, fowl adenovirus 1, Fowlpox virus, Friend virus, Furovirus, Gammaherpesvirinae, gammaretrovirus, GB virus C (GBV-C; formerly Hepatitis G virus), Geminivirus, German measles virus, Getah virus, gibbon ape leukemia virus, green monkey virus (mullburg), glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantavirus, hard clam reovirus, hare fibroma virus, HCMV (human cytomegalovirus), helper virus, hemadsorption virus 2, hemagglutinating virus of Japan, hemorrhagic fever virus, Hendra virus, Henipaviruses, Hepadnavirus, hepatitis A virus, hepatitis B virus, hepatitis C virus, hepatitis D (delta) virus, hepatitis E virus, hepatitis F virus, hepatitis G virus, hepatitis nonA nonB virus, hepatoencephalomyelitis reovirus 3, Hepatovirus, heron hepatitis B virus, herpes B virus, Herpes simplex virus, herpes simplex virus 1, herpes simplex virus 2, Herpesvirus, Herpes zoster, Herpes virus 6, Herpes virus 7, Herpes virus 8, Herpesvirus ateles, Herpesvirus hominis, Herpesvirus saimiri, Herpesvirus suis, Herpesvirus varicellae, Highlands J virus, Hirame rhabdovirus, HIV-1, hog cholera virus, Hordeivirus, Horse Flu, HTLV-1, HTLV-2, human adenovirus 2, human alphaherpesvirus 1, human alphaherpesvirus 2, human alphaherpesvirus 3, human B lymphotropic virus, human betaherpesvirus 5, human coronavirus, Human enterovirus A, Human enterovirus B, Human Flu, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus (HIV), human immunodeficiency virus 1, human immunodeficiency virus 2, Human metapneumovirus, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, ichnovirus, Ilarvirus, infantile gastroenteritis virus, infectious bovine rhinotracheitis virus, infectious haematopoietic necrosis virus, infectious pancreatic necrosis virus, influenza virus, influenzavirus A, influenzavirus B, influenzavirus C, influenzavirus D, influenzavirus pr8, insect iridescent virus, insect virus, interfering virus, iridovirus, Isavirus, Japanese B virus, Japanese encephalitis virus, JC virus, Junin virus, Johnson grass mosaic virus, Kaposi's sarcoma-associated herpesvirus, Kemerovo virus, Kilham's rat virus, Klamath virus, Kolongo virus, Korean hemorrhagic fever virus, kumba virus, Kumlinge virus, Kunjin virus, Kyasanur forest disease, Kyzylagach virus, La Crosse virus, lactic dehydrogenase elevating virus, Lagos bat virus, Lambda phage, langat virus, Langur virus, lapine parvovirus, Lassa fever virus, Lassa virus, latent rat virus, LCM virus, Leaky virus, Lentivirus, Leporipoxvirus, leukemia virus, leukovirus, louping ill virus, lumpy skin disease virus, Luteovirus, lymphadenopathy associated virus, Lymphocytic choriomeningitis virus (LCMV), Lymphocryptovirus, lymphocytic choriomeningitis virus, lymphoproliferative virus group, Lyssavirus, Machupo virus, mad itch virus, maize chlorotic dwarf virus, maize rough dwarf virus, mammalian type B oncovirus group, mammalian type B retroviruses, mammalian type C retrovirus group, mammalian type D retroviruses, mammary tumor virus, Mapuera virus, Marafivirus, Marburg virus, Marburg-like virus, Mason Pfizer monkey virus, Mastadenovirus, Mayaro virus, ME virus, Measles virus, Melandrium yellow fleck virus, Menangle virus, Mengo virus, Mengovirus, Merkel cell polyomavirus, Middelburg virus, milkers nodule virus, mink enteritis virus, minute virus of mice, MLV related virus, MM virus, Mokola virus, Molluscipoxvirus, Molluscum contagiosum virus, Moloney murine leukemia virus (M-MuLV), monkey B virus, Monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, Mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Necrovirus, Neethling virus, Nelson Bay virus, NemtickVirus, Nepovirus, neurotropic virus, New World Arenavirus, newborn pneumonitis virus, Newcastle disease virus, Nipah virus, noncytopathogenic virus, Norovirus, Norwalk virus, nuclear polyhedrosis virus (NPV), nipple neck virus, O' nyong'nyong virus, oat sterile dwarf virus, Ockelbo virus, Omsk hemorrhagic fever virus, oncogenic virus, oncogenic viruslike particle, oncornavirus, Orbivirus, Orf virus, Oropouche virus, Orthohepadnavirus, orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, Parainfluenza virus human (HPIV), parainfluenza virus type 1 human (HPIV-1), parainfluenza virus type 2 human (HPIV-2), parainfluenza virus type 3 human (HPIV-3), parainfluenza virus type 4 human (HPIV-4), Paramyxovirus, Parapoxvirus, paravaccinia virus, parsnip yellow fleck virus, Parvovirus, Parvovirus B19, pea enation mosaic virus, Pestivirus, Phlebovirus, phocine distemper virus, Phytoreovirus, Picodnavirus, Picornavirus, pig cytomegalovirus, pigeonpox virus, Piry virus, Pixuna virus, plant rhabdovirus group, plant virus, pneumonia virus of mice, Pneumovirus, Poliomyelitis virus, Poliovirus, Polydnavirus, polyhedral virus, Polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, Potato leaf roll virus, Potato mop top virus, Potato virus Y, Potexvirus, Potyvirus, Powassan encephalitis virus, Poxvirus, poxvirus variolae, Prospect Hill virus, provirus, pseudocowpox virus, pseudorabies virus, psittacinepox virus, Puumala virus, Qalyub virus, Quail pea mosaic virus, quailpox virus, Queensland fruitfly virus, Quokkapox virus, rabbit fibroma virus, rabbit kidney vaculolating virus, rabbit papillomavirus, Rabies virus, raccoon parvovirus, raccoonpox virus, radish mosaic virus, Ranikhet virus, rat cytomegalovirus, rat parvovirus, rat virus, Rauscher's virus, recombinant vaccinia virus, recombinant virus, Red Clover Necrotic Mosaic Virus, reovirus, reovirus 1, reovirus 2, reovirus 3, reptilian type C virus, Respiratory syncytial virus, respiratory virus, reticuloendotheliosis virus, Retrovirus, Rhabdovirus, Rhabdovirus carpia, Rhadinovirus, Rhinovirus, Rhizidiovirus, rice dwarf virus, rice gall dwarf virus, rice hoja blanca virus, rice ragged stunt virus, Rift Valley fever virus, Riley's virus, rinderpest virus, RNA tumor virus, RNA virus, Roseolovirus, Ross River virus, Rotavirus, rougeole virus, Rous sarcoma virus, Rubella virus, rubeola virus, Rubivirus, Russian autumn encephalitis virus, S6-14-03 virus, SA 11 simian virus, SA 15, SA2 virus, SA6 virus, SA8 virus, Sabia virus, Sabio virus, Sabo virus, Saboya virus, *Sabulodes caberata* GV, Sacbrood virus, *Saccharomyces cerevisiae* virus L-A, *Saccharomyces cerevisiae* virus La, *Saccharomyces cerevisiae* virus LBC, Sagiyama virus, Saguaro cactus virus, aimiriine herpesvirus 1, Saimiriine herpesvirus 2, Sainpaulia leaf necrosis virus, SaintAbb's Head virus, Saint-Floris virus, Sakhalin virus, Sal Vieja virus, Salanga virus, Salangapox virus, Salehabad virus, salivary gland virus, Salmonid herpesvirus 1, Salmonid herpesvirus 2, Salmonis virus, Sambucus vein clearing virus, *Samia cynthia* NPV, *Samia pryeri* NPV, *Samia ricini* NPV, Sammons' Opuntia virus, SanAngelo virus, San Juan virus, San Miguel sealion virus, San Perlita virus, Sand rat nuclear inclusion agents, Sandfly fever Naples virus, Sandfly fever Sicilian virus, Sandjimba virus, Sango virus, Santa Rosa virus, Santarem virus, Santosai temperate virus, Sapphire II virus, Sapporo-like virus, Saraca virus, *Sarracenia purpurea* virus, SARS virus, satellite virus, Sathuperi virus, Satsuma dwarf virus, *Saturnia pavonia* virus, *Saturnia pyri* NPV, Saumarez Reef virus, Sawgrass virus, *Sceliodes cordalis* NPV, Schefflera ringspot virus, Sciaphila duplex GV, *Scirpophaga* incertulas NPV, Sciurid herpesvirus, Sciurid herpesvirus 2, *Scoliopteryx libatrix* NPV, *Scopelodes contracta* NPV, *Scopelodes venosa* NPV, *Scopula subpunctaria* NPV, *Scotogramma trifolii* GV, *Scotogramma trifolu* NPV, Scrophularia mottle virus, SDAV (sialodacryoadenitis virus), sealpox virus, *Selenephera lunigera* NPV, *Selepa celtis* GV, Seletar virus, *Selidosema suavis* NPV, *Semidonta biloba* NPV, *Semiothisa sexmaculata* GV, Semliki Forest Virus, Sena Madureira virus, Sendai virus, SENV-D, SENV-H, Seoul virus, Sepik virus, Serra do Navio virus, Serrano golden mosaic virus, Sesame yellow mosaic virus, *Sesamia calamistis* NPV, *Sesamia cretica* GV, *Sesamia inferens* NPV, *Sesamia nonagrioides* GV, *Setora nitens* virus, Shallot latent virus, Shamonda virus, Shark River virus, Sheep associated malignant catarrhal fever, Sheep papillomavirus, Sheep pulmonary adenomatosis associated herpesvirus, sheeppox virus, Shiant Islands virus, Shokwe virus, Shope fibroma virus, Shope papilloma virus, Shuni virus, Siamese cobra herpesvirus, Sibine fusca densovirus, Sida golden mosaic virus (SiGMV), Sida golden yellow vein virus (SiGYVV), Sigma virus, Sikte water-borne virus, Silverwater virus, Simbu virus, Simian adenoviruses 1 to 27, Simian agent virus 12, Simian enterovirus 1 to 18, simian foamy virus, Simian hemorrhagic fever virus, simian hepatitis A virus, simian human immunodeficiency virus, simian immunodeficiency virus, simian parainfluenza virus, Simian rotavirus SA11, Simian sarcoma virus, simian T cell lymphotrophic virus, Simian type D virus 1, Simian vancella herpesvirus, simian virus, simian virus 40, Simplexvirus, *Simulium vittatum* densovirus, Sin Nombre virus, Sindbis virus, Sint1em's onion latent virus, Sixgun city virus, Skunkpox virus, Smallpox virus, Smelt reovirus, *Smerinthus ocellata* NPV, *Smithiantha* virus, Snakehead rhabdovirus, Snowshoe hare virus, Snyder-Theilen feline sarcoma virus, Sobemovirus, Sofyn virus, Soil-borne wheat mosaic virus, Sokoluk virus, *Solanum apical* leaf curl virus, *Solanum nodiflorum* mottle virus, Solanurn yellows virus, Soldado virus, Somerville virus 4, Sonchus mottle virus, Sonchus virus, Sonchus yellow net virus, Sorghum chlorotic spot virus, Sorghum mosaic virus, Sorghum virus, Sororoca virus, Soursop yellow blotch virus, South African passiflora virus, South American hemorrhagic fever viruses, South African passiflora virus, South River virus, Southern bean mosaic virus, Southern potato latent virus, Sowbane mosaic virus, Sowthistle yellow vein virus, Soybean chlorotic mottle virus, Soybean crinkle leaf virus, Soybean dwarf virus, Soybean mosaic virus, SPAr-2317 virus, *Sparganothis pettitana* NPV, sparrowpox virus, Spartina mottle virus, Spectacled caimanpox virus, SPH 114202 virus, Sphenicid herpesvirus 1, Sphinx ligustri NPV, Spider monkey herpesvirus, *Spilarctia subcarnea* NPV, *Spilonota ocellana* NPV, *Spilosoma lubricipeda* NPV, Spinach latent virus, Spinach temperate virus, Spiroplasma phage 1, *Spiroplasma* phage 4, *Spiroplasma* phage aa, *Spiroplasma* phage C1/T52, *Spodoptera exempta* cypovirus, *Spodoptera exigua* virus, *Spodoptera frugiperda* virus, *Spodoptera latifascia* virus, *Spodoptera littoralis*, *Spodoptera mauritia* virus, *Spodoptera ornithogalli* virus, Spondweni virus, spring beauty latent virus, Spring viremia of carp virus, Spumavirus (SFV, HFV), Squash leaf curl virus, squash mosaic virus, squirrel fibroma virus, Squirrel monkey herpesvirus, squirrel monkey retrovirus, SR-11 virus, Sri Lankan passionfruit mottle virus, Sripur virus, SSV 1 virus group, StAbbs Head virus, St. Louis encephalitis virus, *Staphylococcus* phage 107, *Staphylococcus* phage 187, *Staphylococcus* phage 2848A, *Staphylococcus* phage 3A, *Staphylococcus* phage 44A HJD, *Staphylococcus* phage 77, *Staphylococcus* phage B11-M15, *Staphylococcus* phage Twort, Starlingpox virus, Statice virus Y, P, STLV (simian T lymphotropic virus) type I, STLV (simian T lymphotropic virus) type II, STLV (simian T lymphotropic virus) type III, stomatitis papulosa virus, Stratford virus, Strawberry crinkle virus, Strawberry latent ringspot virus, Strawberry mild yellow edge virus, Strawberry vein banding virus, *Streptococcus* phage 182, *Streptococcus* phage 2BV, *Streptococcus* phage A25, *Streptococcus* phage 24, *Streptococcus* phage PE1, *Streptococcus* phage VD13, *Streptococcus* phage fD8, *Streptococcus* phage CP-1, *Streptococcus* phage Cvir, *Streptococcus* phage H39, Strigid herpesvirus 1, Striped bass reovirus, Striped Jack nervous, necrosis virus, Stump-tailed macaque virus, submaxillary virus, Subterranean clover mottle virus, Subterranean clover mottle virus satellite, Subterranean clover red leaf virus, Subterranean clover stunt virus, Sugarcane bacilliform virus, Sugarcane mild mosaic virus, Sugarcane mosaic virus, Sugarcane streak virus, suid alphaherpesvirus 1, suid herpesvirus 2, Suipoxvirus, Sulfolobus virus 1, Sunday Canyon virus, Sunflower crinkle virus, Sunflower mosaic virus, Sunflower rugose mosaic virus, Sunflower yellow blotch virus, Sunflower yellow ringspot virus, Sun-hemp mosaic virus, swamp fever virus, Sweet clover necrotic mosaic virus, Sweet potato A virus, Sweet potato chlorotic leafspot virus, Sweet potato feathery mottle virus, Sweet potato internal cork virus, Sweet potato latent virus, Sweet potato mild mottle virus, Sweet potato russet crack virus, Sweet potato vein mosaic virus, Sweet potato yellow dwarf virus, Sweetwater Branch virus, Swine cytomegalovirus, Swine Flu, Swine infertility and respiratory syndrome virus, swinepox virus, Swiss mouse leukemia virus, Sword bean distortion mosaic virus, *Synaxis jubararia* NPV, *Synaxis pallulata* NPV, Synetaeris tenuifemur virus, *Syngrapha selecta* NPV, T4 phage, T7 phage, TAC virus, Tacaiuma virus, Tacaribe complex virus, Tacaribe virus, Tadpole edema virus LT 1-4, Taggert virus, Tahyna virus, Tai virus, Taiassui virus, Tamana bat virus, Tamarillo mosaic virus, Tamdy virus, [[Tamiami virus, Tanapox virus, Tanga virus, Tanjong Rabok virus, Taro bacilliform virus, Badnavirus Tataguine virus, Taterapox virus, Taterapox virus, Teasel mosaic virus, Tehran virus, Telfairia mosaic virus, Telok Forest virus, Tembe virus, Tembusu virus, Tench reovirus, Tensaw virus, Tenvivirus, Tephrosia symptomless virus, Termeil virus, Tete virus, *Tetralopha scortealis* NPV, *Tetropium cinnamopterum* NPV, Texas pepper virus, Thailand virus, *Thaumetopoea pityocampa* virus, Theiler's encephalomyelitis virus, Theiler's virus, *Theophila mandarina* NPV, *Theretra japonica* NPV, *Thermoproteus* virus 1, *Thermoproteus* virus 2, *Thermoproteus* virus 3, *Thermoproteus* virus 4, Thiafora virus, Thimiri virus, Thistle mottle virus, Thogoto virus, Thormodseyjarklettur virus, *Thosea asigna* virus, *Thosea baibarana* NPV, *Thosea sinensis* GV, Thottapalayam virus, *Thylidolpteryx ephemeraeformis* NPV, *Thymelicus lineola* NPV, Tibrogargan virus, *Ticera castanea* NPV, Tick borne encephalitis virus (TBEV)—European and Far Eastern subtypes, Tillamook virus, Tilligerry virus, Timbo virus, Tilmboteua virus, Tilmaroo virus, Tindholmur virus, *Tinea pellionella* NPV, *Tineola hisselliella* NPV, *Tinpula paludosa* NPV, *Tinracola plagiata* NPV, Tioman virus, Tlacotalpan virus, Tobacco bushy top virus, Tobacco etch virus, Tobacco leaf curl virus, Tobacco mild green mosaic virus, tobacco mosaic virus, Tobacco mosaic virus satellite, Tobacco mottle virus, Tobacco necrosis virus, Tobacco necrosis virus satellite, Tobacco necrosis virus small satellite, Tobacco necrotic dwarf virus, tobacco rattle virus, Tobacco ringspot virus, Tobacco streak virus, Tobacco stunt virus, Tobacco vein banding mosaic virus, Tobacco vein distorting virus Tobacco vein mottling virus, Tobacco wilt virus, Tobacco yellow dwarf virus, Tobacco yellow net virus, Tobacco yellow vein virus, Tobamovirus Tobravirus, Togavirus, Tomato apical stunt viroid, Tomato aspermy virus, Tomato black ring virus, Tomato black ring virus satellite, Tomato bunchy top viroid, tomato bushy stunt virus, Tomato bushy stunt virus satellite, Tomato golden mosaic virus, Tomato leaf crumple virus, Tomato leaf curl virus, Tomato leafroll virus, Tomato mosaic virus, Tomato mottle virus, Tomato pale chlorosis virus, Tomato planta macho viroid, Tomato pseudo-curly top virus, Tomato ringspot virus, Tomato spotted wilt virus, Tomato top necrosis virus, Tomato vein yellowing virus, Tomato yellow dwarf virus, Tomato yellow leaf curl virus, Tomato yellow mosaic virus, Tomato yellow top virus, Tombusvirus, Tongan vanilla virus, Torovirus, Torque teno virus, *Tortrix loeflingiana* NPV, *Tortrix viridana* NPV, Toscana virus, Tospovirus, *Toxorhynchites brevipalpis* NPV, *Trabala vishnou* NPV, Tradescantia/Zebrina virus, Trager duck spleen necrosis virus, Tranosema sp. Virus, transforming virus, Tree shrew adenovirus 1, Tree shrew herpesvirus, Triatoma virus, Tribec virus, *Trichiocampus irregularis* NPV, *Trichiocampus viminalis* NPV, *Trichomonas vaginalis* virus, *Trichoplusia ni* cypovirus 5, *Trichoplusia ni* granulovirus, *Trichoplusia ni* MNPV, *Trichoplusia ni* Single SNPV, *Trichoplusia ni* virus, Trichosanthes mottle virus, *Triticum aestivum* chlorotic spot virus, Trivittatus virus, Trombetas virus, Tropaeolum virus 1, Tropaeolum virus 2, Trubanarnan virus, Tsuruse virus, Tucunduba virus, Tulare apple mosaic virus, Tulip band breaking virus, Tulip breaking virus, Tulip chlorotic blotch virus, Tulip top breaking virus, Tulip virus X, tumor virus, Tupaia virus, Tupaiid herpesvirus 1, Turbot herpesvirus, Turbot reovirus, Turkey adenoviruses 1 to 3, Turkey coronavirus, Turkey herpesvirus 1, turkey rhinotracheitis virus, turkeypox virus, Turlock virus, Turnip crinkle virus, Turnip crinkle virus satellite, Turnip mild yellows virus, Turnip mosaic virus, Turnip rosette virus, turnip yellow mosaic virus, Turuna virus, Tymovirus, Tyuleniy virus, type C retroviruses, type D oncovirus, type D retrovirus group, Uasin Gishu disease virus, Uganda S virus, *Ugymyia sericariae* NPV, ulcerative disease rhabdovirus, Ullucus mild mottle virus, Ullucus mosaic virus, Ullucus virus C, Umatilla virus, Umbre virus, Una virus, Upolu virus, UR2 sarcoma virus, *Uranotaenia sapphirina* NPV, *Urbanus proteus* NPV, Urucuri virus, *Ustilago maydis* virus 1, *Ustilago maydis* virus 4, *Ustilago maydis* virus 6, Usutu virus, Uting a virus, Utive virus, Uukuniemi virus group, Vaccinia virus, Vaeroy virus, Vallota mosaic virus, *Vanessa atalanta* NPV, *Vanessa cardui* NPV, *Vanessa prorsa* NPV, Vanilla mosaic virus, Vanilla necrosis virus, Varicella zoster virus, Varicellovirus, Varicola virus, variola major virus, variola virus, Vasin Gishu disease virus, Vellore virus, Velvet tobacco mottle virus, Velvet tobacco mottle virus satellite, Venezuelan equine encephalitis virus, Venezuelan equine encephalomyelitis virus, Venezuelan hemorrhagic fever virus, Vesicular stomatitis virus, Vesiculovirus, *Vibrio* phage 06N-22P, *Vibrio* phage 06N-58P, *Vibrio* phage 4996, *Vibrio* phage a3a, *Vibrio* phage I, *Vibrio* phage II, *Vibrio* phage m, *Vibrio* phage IV, *Vibrio* phage kappa, *Vibrio* phage nt-1, *Vibrio* phage OXN-52P, *Vibrio* phage OXN-IOOP, *Vibrio* phage v6, *Vibrio* phage Vfl2, *Vibrio* phage Vf33, *Vibrio* phage VP1, *Vibrio* phage VP11, *Vibrio* phage VP3, *Vibrio* phage VP5, *Vibrio* phage X29, Vicia cryptic virus, *Vigna sinensis* mosaic virus, Vilyuisk virus, Vinces virus, Viola mottle virus, viper retrovirus, viral haemorrhagic septicemia virus, virus-like particle, Visna Maedi virus, Visna virus, Voandzeia mosaic virus, Voandzeia necrotic mosaic virus, volepox virus, Wad Medani virus, Wallal virus, Walleye epidermal hyperplasia, Walrus calicivirus, Wanowrie virus, Warrego virus, Watermelon chlorotic stunt virus, Watermelon curly mottle virus, Watermelon mosaic virus 1, Watermelon mosaic virus 2, Weddel water-borne virus, Weldona virus, Wesselsbron virus, West Nile virus, western equine encephalitis virus, western equine encephalomyelitis virus, Wexford virus, Whataroa virus, Wheat American striate mosaic virus, Wheat chlorotic streak virus, Wheat dwarf virus, Wheat rosette stunt virus, Wheat streak mosaic virus, Wheat yellow leaf virus, Wheat yellow mosaic virus, White bryony virus, White clover cryptic virus 1, White clover cryptic virus 2, White clover cryptic virus 3, White clover mosaic virus, White lupinrnosaic virus, Wild cucumber mosaic virus, Wild potato mosaic virus, Wildbeest herpesvirus, Wineberry latent virus, Winter wheat mosaic virus, Winter wheat Russian mosaic virus, *Wiseana cervinata* virus, *Wiseana signata* virus, *Wiseana umbraculata* virus, Wissadula mosaic virus, Wisteria vein mosaic virus, Witwatersrand virus, Wongal virus, Wongorr virus, Winter Vomiting Virus, woodchuck hepatitis B virus, Woodchuck herpesvirus marmota 1, woolly monkey sarcoma virus, wound tumor virus, WRSV virus, WVU virus 2937, WW virus 71 to 212, *Wyeomyia smithii* NPV, Wyeomyia virus, *Xanthomonas* phage Cf, *Xanthomonas* phage Cflt, *Xanthomonas* phage RR66, *Xanthomonas* phage Xf, *Xanthomonas* phage Xf2, *Xanthomonas* phage XP5, *Xenopus* virus T21, Xiburema virus, Xingu virus, *Xylena curvimacula* NPV, Y73 sarcoma virus, Yaba monkey tumor virus, Yaba-1 virus, Yaba-7 virus, Yacaaba virus, Yam mosaic virus, Yaounde virus, Yaquina Head virus, Yatapoxvirus, Yellow fever virus, Yogue virus, Yokapox virus, Yokase virus, *Yponomeuta cognatella* NPV, *Yponomeuta evonymella* NPV, *Yponomeuta malinellus* NPV, *Yponomeuta padella* NPV, *Yucca baciliform* virus, Yug Bogdanovac virus, Zaliv Terpeniya virus, *Zea mays* virus, Zegla virus, *Zeiraphera diniana* virus, *Zeiraphera pseudotsugana* NPV, Zika virus, Zirqa virus, Zoysia mosaic virus, Zucchini yellow fleck virus, Zucchini yellow mosaic virus, and Zygocactus virus.

In one embodiment the antimicrobial composition according to the present invention is used to inhibit, kill, and/or prevent the growth of one or more fungi, such as those described elsewhere in the application.

The antimicrobial composition can also be used as an antimicrobial detergent, an antimicrobial hand wash, an antimicrobial toothpaste, an antimicrobial mouthwash, an antimicrobial textile treatment etc.

Use of the Composition from *C. finmarchicus* as a Pharmaceutical

In one embodiment, the present invention relates to a pharmaceutical composition obtained from *Calanus finmarchicus*.

The composition obtained from *Calanus finmarchicus* can in one embodiment of the present invention be used as a medicament.

In one embodiment of the present invention a composition obtained from *Calanus finmarchicus* is used in the treatment of microbial infections in an individual in need thereof.

In another embodiment the composition obtained from *Calanus finmarchicus* is used for the manufacture of a medicament for the treatment microbial infections.

The treatment can be ameliorating, curative or prophylactic treatment of one or more infectious diseases.

An infectious disease is in one embodiment a clinically evident disease resulting from the presence of pathogenic agents, including pathogenic viruses, pathogenic bacteria, fungi, protozoa, multicellular parasites, and aberrant proteins known as prions. These pathogens are able to cause disease in human beings, animals and/or plants. Microbial infections include infections caused by bacteria, fungi, protozoans, and viruses.

Infectious pathologies are usually qualified as contagious diseases (also called communicable diseases) due to their potentiality of transmission from one person or species to another. Transmission of an infectious disease may occur through one or more of diverse pathways including physical contact with infected individuals. These infecting agents may also be transmitted through liquids, food, body fluids, contaminated objects, airborne inhalation, or through vector-borne spread.

The term infectivity describes the ability of an organism to enter, survive and multiply in the host, while the infectiousness of a disease indicates the comparative ease with which the disease is transmitted to other hosts. An infection is not synonymous with an infectious disease, as an infection may not cause important clinical symptoms or impair host function.

In a preferred embodiment the present invention relates to treatment of bacterial infections.

In another preferred embodiment, the present invention relates to treatment of fungal infections.

In another embodiment, the present invention relates to treatment of viral infections.

Bacteria

In one embodiment, the composition of the present invention is directed against a bacteria, i.e. it is antibacterial or an antibiotic.

In one embodiment the antimicrobial composition of the present invention can be used as a broad-spectrum antibiotic.

In one embodiment, the antibacterial activity is directed against one or more bacteria selected from the group consisting of Gram positive bacteria, Gram negative bacteria, aerobic bacteria, anaerobic bacteria.

In one embodiment the composition according to the present invention can be used for treatment of one or more diseases caused one or more bacteria such as one or more of the bacteria selected from the group consisting of *Acetobacter aurantius, Acinetobacter* species: *Acinetobacter baumannii, Acinetobacter calcoaceticus, Acinetobacter johnsonii, Acinetobacter junii, Acinetobacter lwoffii, Acinetobacter radioresistens, Acinetobacter septicus, Acinetobacter schindleri, Acinetobacter ursingii; Actinomyces* species: *Actinomyces bovis, Actinomyces bowdenii, Actinomyces canis, Actinomyces cardiffensis, Actinomyces catuli, Actinomyces coleocanis, Actinomyces dentalis, Actinomyces denticolens, Actinomyces europaeus, Actinomyces funkei, Actinomyces georgiae, Actinomyces gerencseriae, Actinomyces graevenitzii, Actinomyces hongkongensis, Actinomyces hordeovulneris, Actinomyces howellii, Actinomyces humiferus, Actinomyces hyovaginalis, Actinomyces israelii, Actinomyces marimammalium, Actinomyces meyeri, Actinomyces naeslundii, Actinomyces nasicola, Actinomyces neuii, Actinomyces odontolyticus, Actinomyces oricola, Actinomyces radicidentis, Actinomyces radingae, Actinomyces slackii, Actinomyces streptomycini, Actinomyces suimastitidis, Actinomyces suis, Actinomyces turicensis, Actinomyces urogenitalis, Actinomyces vaccimaxillae, Actinomyces viscosus; Actinobacillus* species: *Actinobacillus actinomycetemcomitans, Actinobacillus arthritidis, Actinobacillus capsulatus, Actinobacillus delphinicola, Actinobacillus equuli, Actinobacillus hominis, Actinobacillus indolicus, Actinobacillus lignieresii, Actinobacillus minor, Actinobacillus muris, Actinobacillus pleuropneumoniae, Actinobacillus porcinus, Actinobacillus rossii, Actinobacillus scotiae, Actinobacillus seminis, Actinobacillus succinogenes, Actinobacillus suis, Actinobacillus ureae; Aeromonas* species: *Aeromonas allosaccharophila, Aeromonas bestiarum, Aeromonas bivalvium, Aeromonas encheleia, Aeromonas enteropelogenes, Aeromonas euchrenophila, Aeromonas hydrophila, Aeromonas ichthiosmia, Aeromonas jandaei, Aeromonas media, Aeromonas molluscorum, Aeromonas popoffii, Aeromonas punctata, Aeromonas salmonicida, Aeromonas schubertii, Aeromonas sharmana, Aeromonas simiae, Aeromonas sobria, Aeromonas veronii; Afipia felis, Agrobacterium* species: *Agrobacterium radiobacter, Agrobacterium rhizogenes, Agrobacterium rubi, Agrobacterium tumefaciens; Agromonas* species, *Alcaligenes* species: *Alcaligenes aquatilis, Alcaligenes eutrophus, Alcaligenes faecalis, Alcaligenes latus, Alcaligenes xylosoxidans; Alishewanella* species, *Alterococcus* species, *Anaplasma phagocytophilum, Anaplasma marginale, Aquamonas* species, *Arcanobacterium haemolyticum, Aranicola* species, *Arsenophonus* species, *Azotivirga* species, *Azotobacter vinelandii, Azotobacter chroococcum,* Bacillary dysentery (Shigellosis), *Bacillus* species: *Bacillus abortus* (*Brucella melitensis* biovar *abortus*), *Bacillus anthracis* (Anthrax), *Bacillus brevis, Bacillus cereus, Bacillus coagulans, Bacillus fusiformis, Bacillus globigii, Bacillus licheniformis, Bacillus megaterium, Bacillus mycoides, Bacillus natto, Bacillus stearothermophilus, Bacillus subtilis, Bacillus sphaericus, Bacillus thuringiensis; Bacteroides* species: *Bacteroides forsythus* (*Tannerella forsythensis*), *Bacteroides acidifaciens, Bacteroides distasonis* (reclassified as *Parabacteroides distasonis*), *Bacteroides gingivalis, Bacteroides gracilis, Bacteroides fragilis, Bacteroides oris, Bacteroides ovatus, Bacteroides putredinis, Bacteroides pyogenes, Bacteroides stercoris, Bacteroides suis, Bacteroides tectus, Bacteroides thetaiotaomicron, Bacteroides vulgatus; Bartonella* species: *Bartonella alsatica, Bartonella bacilliformis, Bartonella birtlesii, Bartonella bovis, Bartonella capreoli, Bartonella clarridgeiae, Bartonella doshiae, Bartonella elizabethae, Bartonella grahamii, Bartonella henselae* (cat scratch fever), *Bartonella koehlerae, Bartonella muris, Bartonella peromysci, Bartonella quintana, Bartonella rochalimae, Bartonella schoenbuchii, Bartonella talpae, Bartonella taylorii, Bartonella tribocorum, Bartonella vinsonii* spp. Arupensis, *Bartonella vinsonii* spp. Berkhoffii, *Bartonella vinsonii* spp. Vinsonii, *Bartonella washoensis*; BCG (Bacille Calmette-Guerin), *Bergeyella zoohelcum* (*Weeksella zoohelcum*), *Bifidobacterium bifidum, Blastobacter* species, *Blochmannia* species, *Bordetella* species: '*Bordetella ansorpii*', *Bordetella avium, Bordetella bronchiseptica, Bordetella hinzii, Bordetella holmesii, Bordetella parapertussis, Bordetella pertussis* (Whooping cough), *Bordetella petrii, Bordetella trematum; Borrelia* species: *Borrelia burgdorferi, Borrelia afzelii, Borrelia anserina, Borrelia garinii, Borrelia valaisiana, Borrelia hermsii, Borrelia Parkeri, Borrelia recurrentis; Bosea* species, *Bradyrhizobium* species, *Brenneria* species, *Brucella* species: *Brucella abortus, Brucella canis, Brucella melitensis, Brucella neotomae, Brucella ovis, Brucella suis, Brucella pinnipediae; Buchnera* species, *Budvicia* species, *Burkholderia* species: *Burkholderia cepacia* (*Pseudomonas cepacia*), *Burkholderia mallei* (*Pseudomonas mallei/Actinobacillus mallei*), *Burkholderia pseudomallei* (*Pseudomonas pseudomallei*); *Buttiauxella* species, *Calymmatobacterium granulomatis, Campylobacter* species: *Campylobacter coli, Campylobacter concisus, Campylobacter curvus, Campylobacter fetus, Campylobacter gracilis, Campylobacter helveticus, Campylobacter hominis, Campylobacter hyointestinalis, Campylobacter insulaenigrae, Campylobacter jejuni, Campylobacter lanienae, Campylobacter lari, Campylobacter mucosalis, Campylobacter rectus, Campylobacter showae, Campylobacter sputorum, Campylobacter upsaliensis; Capnocytophaga canimorsus* (Dysgonic fermenter type 2), *Corynebacterium* species, *Cardiobacterium hominis,*

*Cedecea* species, *Chlamydia* species: *Chlamydia trachomatis* (Lymphogranuloma venereum), *Chlamydia muridarum*, *Chlamydia suis*; *Chlamydophila* species: *Chlamydophila pneumoniae*, *Chlamydophila psittaci* (Psittacosis), *Chlamydophila pecorum*, *Chlamydophila abortus*, *Chlamydophila felis*, *Chlamydophila caviae*; *Citrobacter* species: *Citrobacter amalonaticus*, *Citrobacter braakii*, *Citrobacter farmeri*, *Citrobacter freundii*, *Citrobacter gillenii*, *Citrobacter intermedius*, *Citrobacter koseri* aka *Citrobacter diversus*, *Citrobacter murliniae*, *Citrobacter rodentium*, *Citrobacter sedlakii*, *Citrobacter werkmanii*, *Citrobacter youngae*; *Clostridium* species: *Clostridium botulinum*, *Clostridium difficile*, *Clostridium novyi*, *Clostridium septicum*, *Clostridium tetani* (Tetanus), *Clostridium welchii* (*Clostridium perfringens*); *Corynebacterium* species: *Corynebacterium diphtheriae* (Diphtheria), *Corynebacterium amycolatum*, *Corynebacterium aquaticum*, *Corynebacterium bovis*, *Corynebacterium equi*, *Corynebacterium flavescens*, *Corynebacterium glutamicum*, *Corynebacterium haemolyticum*, *Corynebacterium jeikeiun* (corynebacteria of group JK), *Corynebacterium minutissimum* (Erythrasma), *Corynebacterium parvum* (also called *Propionibacterium acnes*), *Corynebacterium pseudodiptheriticum* (also called *Corynebacterium hofmannii*), *Corynebacterium pseudotuberculosis* (also called *Corynebacterium ovis*), *Corynebacterium pyogenes*, *Corynebacterium urealyticum* (corynebacteria of group D2), *Corynebacterium renale*, *Corynebacterium striatum*, *Corynebacterium tenuis* (*Trichomycosis palmellina*, *Trichomycosis axillaris*), *Corynebacterium ulcerans*, *Corynebacterium xerosis*; *Coxiella burnetii* (Q fever), *Cronobacter* species: *Cronobacter sakazakii*, *Cronobacter malonaticus*, *Cronobacter turicensis*, *Cronobacter muytjensii*, *Cronobacter dublinensis*; *Delftia acidovorans* (*Comamonas acidovorans*), *Dickeya* species, *Edwardsiella* species, *Eikenella corrodens*, *Enterobacter* species: *Enterobacter aerogenes*, *Enterobacter cloacae*, *Enterobacter sakazakii*; *Enterococcus* species: *Enterococcus avium*, *Enterococcus durans*, *Enterococcus faecalis* (*Streptococcus faecalis*/*Streptococcus* Group D), *Enterococcus faecium*, *Enterococcus solitarius*, *Enterococcus galllinarum*, *Enterococcus maloratus*; *Ehrlichia chaffeensis*, *Erysipelothrix rhusiopathiae*, *Erwinia* species, *Escherichia* species: *Escherichia adecarboxylata*, *Escherichia albertii*, *Escherichia blattae*, *Escherichia coli*, *Escherichia fergusonii*, *Escherichia hermannii*, *Escherichia vulneris*; *Ewingella* species, *Flavobacterium* species: *Flavobacterium aquatile*, *Flavobacterium branchiophilum*, *Flavobacterium columnare*, *Flavobacterium flevense*, *Flavobacterium gondwanense*, *Flavobacterium hydatis*, *Flavobacterium johnsoniae*, *Flavobacterium pectinovorum*, *Flavobacterium psychrophilum*, *Flavobacterium saccharophilum*, *Flavobacterium salegens*, *Flavobacterium scophthalmum*, *Flavobacterium succinans*; *Francisella tularensis* (Tularaemia), *Francisella novicida*, *Francisella philomiragia*, *Fusobacterium* species: *Fusobacterium necrophorum* (Lemierre syndrome/*Sphaerophorus necrophorus*), *Fusobacterium nucleatum*, *Fusobacterium polymorphum*, *Fusobacterium novum*, *Fusobacterium mortiferum*, *Fusobacterium varium*; *Gardnerella vaginalis*, *Gemella haemolysans*, *Gemella morbillorum* (*Streptococcus morbillorum*), *Grimontella* species, *Haemophilus* species: *Haemophilus aegyptius* (Koch-Weeks bacillus), *Haemophilus aphrophilus*, *Haemophilus avium*, *Haemophilus ducreyi* (Chancroid), *Haemophilus felis*, *Haemophilus haemolyticus*, *Haemophilus influenzae* (Pfeiffer bacillus), *Haemophilus paracuniculus*, *Haemophilus parahaemolyticus*, *Haemophilus parainfluenzae*, *Haemophilus paraphrophilus* (*Aggregatibacter aphrophilus*), *Haemophilus pertussis*, *Haemophilus pittmaniae*, *Haemophilus somnus*, *Haemophilus vaginalis*; *Hafnia* species, *Hafnia alvei*, *Helicobacter* species: *Helicobacter acinonychis*, *Helicobacter anseris*, *Helicobacter aurati*, *Helicobacter bilis*, *Helicobacter bizzozeronii*, *Helicobacter brantae*, *Helicobacter Canadensis*, *Helicobacter canis*, *Helicobacter cholecystus*, *Helicobacter cinaedi*, *Helicobacter cynogastricus*, *Helicobacter felis*, *Helicobacter fennelliae*, *Helicobacter ganmani*, *Helicobacter heilmannii* (*Gastrospirillum hominis*), *Helicobacter hepaticus*, *Helicobacter mesocricetorum*, *Helicobacter marmotae*, *Helicobacter muridarum*, *Helicobacter mustelae*, *Helicobacter pametensis*, *Helicobacter pullorum*, *Helicobacter pylori* (stomach ulcer), *Helicobacter rappini*, *Helicobacter rodentium*, *Helicobacter salomonis*, *Helicobacter trogontum*, *Helicobacter typhlonius*, *Helicobacter winghamensis*; Human granulocytic ehrlichiosis (*Anaplasma phagocytophilum*/*Ehrlichia phagocytophila*), Human monocytotropic ehrlichiosis (Monocytic ehrlichiosis/*Ehrlichia chaffeensis*), *Klebsiella* species: *Klebsiella granulomatis* (*Calymmatobacterium granulomatis*), *Klebsiella mobilis*, *Klebsiella ornithinolytica*, *Klebsiella oxytoca*, *Klebsiella ozaenae*, *Klebsiella planticola*, *Klebsiella pneumoniae*, *Klebsiella rhinoscleromatis*, *Klebsiella singaporensis*, *Klebsiella terrigena*, *Klebsiella trevisanii*, *Klebsiella variicola*; *Kingella kingae*, *Kluyvera* species, *Lactobacillus* species: *Lactobacillus acetotolerans*, *Lactobacillus acidifarinae*, *Lactobacillus acidipiscis*, *Lactobacillus acidophilus* (*Doderlein bacillus*), *Lactobacillus agilis*, *Lactobacillus algidus*, *Lactobacillus alimentarius*, *Lactobacillus amylolyticus*, *Lactobacillus amylophilus*, *Lactobacillus amylotrophicus*, *Lactobacillus amylovorus*, *Lactobacillus animalis*, *Lactobacillus antri*, *Lactobacillus apodemi*, *Lactobacillus aviarius*, *Lactobacillus bifermentans*, *Lactobacillus brevis*, *Lactobacillus buchneri*, *Lactobacillus camelliae*, *Lactobacillus casei*, *Lactobacillus catenaformis*, *Lactobacillus ceti*, *Lactobacillus coleohominis*, *Lactobacillus collinoides*, *Lactobacillus composti*, *Lactobacillus concavus*, *Lactobacillus coryniformis*, *Lactobacillus crispatus*, *Lactobacillus crustorum*, *Lactobacillus curvatus*, *Lactobacillus delbrueckii*, *Lactobacillus delbrueckii* subsp. *Bulgaricus*, *Lactobacillus delbrueckii* subsp. *Lactis*, *Lactobacillus diolivorans*, *Lactobacillus equi*, *Lactobacillus equigenerosi*, *Lactobacillus farraginis*, *Lactobacillus farciminis*, *Lactobacillus fermentum*, *Lactobacillus formicalis*, *Lactobacillus fructivorans*, *Lactobacillus frumenti*, *Lactobacillus fuchuensis*, *Lactobacillus gallinarum*, *Lactobacillus gasseri*, *Lactobacillus gastricus*, *Lactobacillus ghanensis*, *Lactobacillus graminis*, *Lactobacillus hammesii*, *Lactobacillus hamsteri*, *Lactobacillus harbinensis*, *Lactobacillus hayakitensis*, *Lactobacillus helveticus*, *Lactobacillus hilgardii*, *Lactobacillus homohiochii*, *Lactobacillus iners*, *Lactobacillus ingluviei*, *Lactobacillus intestinalis*, *Lactobacillus jensenii*, *Lactobacillus johnsonii*, *Lactobacillus kalixensis*, *Lactobacillus kefuranofaciens*, *Lactobacillus kefiri*, *Lactobacillus kimchii*, *Lactobacillus kitasatonis*, *Lactobacillus kunkeei*, *Lactobacillus leichmannii*, *Lactobacillus lindneri*, *Lactobacillus malefermentans*, *Lactobacillus mali*, *Lactobacillus manihotivorans*, *Lactobacillus mindensis*, *Lactobacillus mucosae*, *Lactobacillus murinus*, *Lactobacillus nagelii*, *Lactobacillus namurensis*, *Lactobacillus nantensis*, *Lactobacillus oligofermentans*, *Lactobacillus oris*, *Lactobacillus panis*, *Lactobacillus pantheris*, *Lactobacillus parabrevis*, *Lactobacillus parabuchneri*, *Lactobacillus paracollinoides*, *Lactobacillus parafarraginis*, *Lactobacillus parakefiri*, *Lactobacillus paralimentarius*, *Lactobacillus parakefiri*, *Lactobacillus paralimentarius*, *Lactobacillus paraplantarum*, *Lactobacillus pentosus*, *Lactobacillus perolens*, *Lactobacillus plantarum*, *Lactobacillus pontis*, *Lactobacillus psittaci*, *Lactobacillus rennini*, *Lactobacillus reuteri*,

*Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae, Lactobacillus zymae; Leclercia species, Legionella species: Legionella adelaidensis, Legionella anisa, Legionella beliardensis, Legionella birminghamensis, Legionella bozemanii, Legionella brunensis, Legionella busanensis, Legionella cherrii, Legionella cincinnatiensis, Legionella donaldsonii, Legionella drancourtii, Legionella drozanskii, Legionella erythra, Legionella fairfieldensis, Legionella fallonii, Legionella feeleii, Legionella geestiana, Legionella genomospecies, Legionella gratiana, Legionella gresilensis, Legionella hackeliae, Legionella impletisoli, Legionella israelensis, Legionella jamestowniensis, 'Candidatus Legionella jeonii', Legionella jordanis, Legionella lansingensis, Legionella londiniensis, Legionella longbeachae, Legionella lytica, Legionella maceachernii, Legionella micdadei, Legionella moravica, Legionella nautarum, Legionella oakridgensis, Legionella parisiensis, Legionella pneumophila, Legionella quateirensis, Legionella quinlivanii, Legionella rowbothamii, Legionella rubrilucens, Legionella sainthelensi, Legionella santicrucis, Legionella shakespearei, Legionella spiritensis, Legionella steigerwaltii, Legionella taurinensis, Legionella tucsonensis, Legionella wadsworthii, Legionella waltersii, Legionella worsleiensis, Legionella yabuuchiae; Leminorella species, Leptospira species: Leptospira interrogans, Leptospira kirschneri, Leptospira noguchii, Leptospira alexanderi, Leptospira weilii, Leptospira genomospecies 1, Leptospira borgpetersenii, Leptospira santarosai, Leptospira inadai, Leptospira fainei, Leptospira broomii, Leptospira licerasiae, Leptospira biflexa, Leptospira meyeri, Leptospira wolbachii, Leptospira genomospecies 3, Leptospira genomospecies 4, Leptospira genomospecies 5;* Lepromatous leprosy (Danielssen-Boeck disease), *Leptospira canicola, Leptospira hebdomadis,* Leptospirosis (Weil disease/*Leptospira icterohaemorrhagiae/Leptospira interrogans* serovar *icterohaemorrhagiae*), *Leptotrichia, Leuconostoc* species: *Leuconostoc carnosum, Leuconostoc citreum, Leuconostoc durionis, Leuconostoc fallax, Leuconostoc ficulneum, Leuconostoc fructosum, Leuconostoc garlicum, Leuconostoc gasicomitatum, Leuconostoc gelidum, Leuconostoc inhae, Leuconostoc kimchii, Leuconostoc lactis, Leuconostoc mesenteroides, Leuconostoc pseudoficulneum, Leuconostoc pseudomesenteroides; Listeria* species: *Listeria grayi, Listeria innocua, Listeria ivanovii, Listeria monocytogenes* (Listeriosis), *Listeria seeligeri, Listeria welshimeri; Methanobacterium extroquens, Microbacterium multiforme, Micrococcus* species: *Micrococcus antarcticus, Micrococcus flavus, Micrococcus luteus, Micrococcus lylae, Micrococcus mucilaginosis, Micrococcus roseus, Micrococcus sedentarius; Mobiluncus, Moellerella* species, *Morganella* species, *Moraxella* species: *Moraxella atlantae, Moraxella boevrei, Moraxella bovis, Moraxella canis, Moraxella caprae, Moraxella catarrhalis* (*Branhamella catarrhalis*), *Moraxella caviae, Moraxella cuniculi, Moraxella equi, Moraxella lacunata, Moraxella lincolnii, Moraxella nonliquefaciens, Moraxella oblonga, Moraxella osloensis, Moraxella saccharolytica; Morganella morganii, Mycobacterium* species: *Mycobacterium abscessus, Mycobacterium africanum, Mycobacterium agri, Mycobacterium aichiense, Mycobacterium alvei, Mycobacterium arupense, Mycobacterium asiaticum, Mycobacterium aubagnense, Mycobacterium aurum, Mycobacterium austroafricanum, Mycobacterium avium* (Battey disease/Lady Windermere syndrome), *Mycobacterium avium paratuberculosis* (implicated in Crohn's disease in humans and Johne's disease in sheep), *Mycobacterium avium silvaticum, Mycobacterium avium "hominissuis", Mycobacterium colombiense, Mycobacterium boenickei, Mycobacterium bohemicum, Mycobacterium bolletii, Mycobacterium botniense, Mycobacterium bovis* (Bovine tuberculosis), *Mycobacterium branderi, Mycobacterium brisbanense, Mycobacterium brumae, Mycobacterium canariasense, Mycobacterium caprae, Mycobacterium celatum, Mycobacterium chelonae, Mycobacterium chimaera, Mycobacterium chitae, Mycobacterium chlorophenolicum, Mycobacterium chubuense, Mycobacterium conceptionense, Mycobacterium confluentis, Mycobacterium conspicuum, Mycobacterium cookii, Mycobacterium cosmeticum, Mycobacterium diernhoferi, Mycobacterium doricum, Mycobacterium duvalii, Mycobacterium elephantis, Mycobacterium fallax, Mycobacterium farcinogenes, Mycobacterium flavescens, Mycobacterium florentinum, Mycobacterium fluoroanthenivorans, Mycobacterium fortuitum, Mycobacterium fortuitum* subsp. *Acetamidolyticum, Mycobacterium frederiksbergense, Mycobacterium gadium, Mycobacterium gastri, Mycobacterium genavense, Mycobacterium gilvum, Mycobacterium goodii, Mycobacterium gordonae* (*Mycobacterium aquae*), *Mycobacterium haemophilum, Mycobacterium hassiacum, Mycobacterium heckeshornense, Mycobacterium heidelbergense, Mycobacterium hiberniae, Mycobacterium hodleri, Mycobacterium holsaticum, Mycobacterium houstonense, Mycobacterium immunogenum, Mycobacterium interjectum, Mycobacterium intermedium, Mycobacterium intracellulare, Mycobacterium kansasii, Mycobacterium komossense, Mycobacterium kubicae, Mycobacterium kumamotonense, Mycobacterium lacus, Mycobacterium lentiflavum, Mycobacterium leprae* (causes leprosy or Hansen disease/Hanseniasis), *Mycobacterium lepraemurium, Mycobacterium madagascariense, Mycobacterium mageritense, Mycobacterium malmoense, Mycobacterium marinum* (Fish tank granuloma), *Mycobacterium massiliense, Mycobacterium microti, Mycobacterium monacense, Mycobacterium montefiorense, Mycobacterium moriokaense, Mycobacterium mucogenicum, Mycobacterium murale, Mycobacterium nebraskense, Mycobacterium neoaurum, Mycobacterium neworleansense, Mycobacterium nonchromogenicum, Mycobacterium novocastrense, Mycobacterium obuense, Mycobacterium palustre, Mycobacterium parafortuitum, Mycobacterium parascrofulaceum, Mycobacterium parmense, Mycobacterium peregrinum, Mycobacterium phlei, Mycobacterium phocaicum, Mycobacterium pinnipedii, Mycobacterium porcinum, Mycobacterium poriferae, Mycobacterium pseudoshottsii, Mycobacterium pulveris, Mycobacterium psychrotolerans, Mycobacterium pyrenivorans, Mycobacterium rhodesiae, Mycobacterium saskatchewanense, Mycobacterium scrofulaceum, Mycobacterium senegalense, Mycobacterium seoulense, Mycobacterium septicum, Mycobacterium shimoidei, Mycobacterium shottsii, Mycobacterium simiae, Mycobacterium smegmatis, Mycobacterium sphagni, Mycobacterium szulgai, Mycobacterium terrae, Mycobacterium thermoresistibile, Mycobacterium tokaiense, Mycobacterium triplex, Mycobacterium triviale, Mycobacterium tuberculosis* (major cause of human tuberculosis), *Mycobacterium bovis, Mycobacterium africanum, Mycobacterium canetti, Mycobacterium caprae, Mycobacterium pinnipedii', Mycobacterium tusciae, Mycobacterium ulcerans* (causes Bairnsdale ulcer/

Buruli ulcer), *Mycobacterium vaccae, Mycobacterium vanbaalenii, Mycobacterium wolinskyi, Mycobacterium xenopi*; *Mycoplasma* species: *Mycoplasma fermentans, Mycoplasma genitalium, Mycoplasma hominis, Mycoplasma penetrans, Mycoplasma phocacerebrale, Mycoplasma pneumoniae, Nanukayami* (Seven-day fever/Gikiyami), *Neisseria* species: *Neisseria gonorrhoea* (Gonococcus/Gonorrhea), *Neisseria meningiditis* (Meningococcus), *Neisseria sicca, Neisseria cinerea, Neisseria elongata, Neisseria flavescens, Neisseria lactamica, Neisseria mucosa, Neisseria polysaccharea, Neisseria subflava; Nitrobacter* species, *Nocardia* species: *Nocardia asteroides, Nocardia brasiliensis, Nocardia caviae*; Noma (cancrum oris/gangrenous stomatitis), *Obesumbacterium, Oligotropha* species, *Orientia tsutsugamushi* (Scrub typhus), *Oxalobacter formigenes, Pantoea* species: *Pantoea agglomerans, Pantoea ananatis, Pantoea citrea, Pantoea dispersa, Pantoea punctata, Pantoea stewartii, Pantoea terrea; Pasteurella* species: *Pasteurella aerogenes, Pasteurella anatis, Pasteurella avium, Pasteurella bettyae, Pasteurella caballi, Pasteurella canis, Pasteurella dagmatis, Pasteurella gallicida, Pasteurella gallinarum, Pasteurella granulomatis, Pasteurella langaaensis, Pasteurella lymphangitidis, Pasteurella mairii, Pasteurella multocida, Pasteurella pneumotropica, Pasteurella skyensis, Pasteurella stomatis, Pasteurella testudinis, Pasteurella trehalosi, Pasteurella tularensis, Pasteurella ureae, Pasteurella volantium; Pediococcus* species: *Pediococcus acidilactici, Pediococcus cellicola, Pediococcus claussenii, Pediococcus damnosus, Pediococcus dextrinicus, Pediococcus ethanolidurans, Pediococcus inopinatus, Pediococcus parvulus, Pediococcus pentosaceus, Pediococcus stilesii; Peptostreptococcus* species: *Peptostreptococcus anaerobius, Peptostreptococcus asaccharolyticus, Peptostreptococcus harei, Peptostreptococcus hydrogenalis, Peptostreptococcus indoliticus, Peptostreptococcus ivorii, Peptostreptococcus lacrimalis, Peptostreptococcus lactolyticus, Peptostreptococcus magnus, Peptostreptococcus micros, Peptostreptococcus octavius, Peptostreptococcus prevotii, Peptostreptococcus tetradius, Peptostreptococcus vaginalis; Photorhabdus* species, *Photorhizobium* species, *Plesiomonas shigelloides, Porphyromonas gingivalis, Pragia* species, *Prevotella, Propionibacterium* species: *Propionibacterium acnes, Propionibacterium propionicus; Proteus* species: *Proteus mirabilis, Proteus morganii, Proteus penneri, Proteus rettgeri, Proteus vulgaris; Providencia* species: *Providencia friedericiana, Providencia stuartii; Pseudomonas* species: *Pseudomonas aeruginosa, Pseudomonas alcaligenes, Pseudomonas anguilliseptica, Pseudomonas argentinensis, Pseudomonas borbori, Pseudomonas citronellolis, Pseudomonas flavescens, Pseudomonas mendocina, Pseudomonas nitroreducens, Pseudomonas oleovorans, Pseudomonas pseudoalcaligenes, Pseudomonas resinovorans, Pseudomonas straminea, Pseudomonas aurantiaca, Pseudomonas aureofaciens, Pseudomonas chlororaphis, Pseudomonas fragi, Pseudomonas lundensis, Pseudomonas taetrolens, Pseudomonas Antarctica, Pseudomonas azotoformans, Pseudomonas brassicacearum, Pseudomonas brenneri, Pseudomonas cedrina, Pseudomonas corrugate, Pseudomonas fluorescens, Pseudomonas gessardii, Pseudomonas libanensis, Pseudomonas mandelii, Pseudomonas marginalis, Pseudomonas mediterranea, Pseudomonas meridiana, Pseudomonas migulae, Pseudomonas mucidolens, Pseudomonas orientalis, Pseudomonas panacis, Pseudomonas proteolytica, Pseudomonas rhodesiae, Pseudomonas synxantha, Pseudomonas thivervalensis, Pseudomonas tolaasii, Pseudomonas veronii, Pseudomonas denitrificans, Pseudomonas pertucinogena, Pseudomonas cremoricolorata, Pseudomonas fulva, Pseudomonas monteilii, Pseudomonas mosselii, Pseudomonas oryzihabitans, Pseudomonas parafulva, Pseudomonas plecoglossicida, Pseudomonas putida, Pseudomonas balearica, Pseudomonas luteola, Pseudomonas stutzeri, Pseudomonas amygdale, Pseudomonas avellanae, Pseudomonas caricapapayae, Pseudomonas cichorii, Pseudomonas coronafaciens, Pseudomonas ficuserectae, Pseudomonas meliae, Pseudomonas savastanoi, Pseudomonas syringae, Pseudomonas viridiflava, Pseudomonas abietaniphila, Pseudomonas acidophila, Pseudomonas agarici, Pseudomonas alcaliphila, Pseudomonas alkanolytica, Pseudomonas amyloderamosa, Pseudomonas asplenii, Pseudomonas azotifigens, Pseudomonas cannabina, Pseudomonas coenobios, Pseudomonas congelans, Pseudomonas costantinii, Pseudomonas cruciviae, Pseudomonas delhiensis, Pseudomonas excibis, Pseudomonas extremorientalis, Pseudomonas frederiksbergensis, Pseudomonas fuscovaginae, Pseudomonas gelidicola, Pseudomonas grimontii, Pseudomonas indica, Pseudomonas jessenii, Pseudomonas jinjuensis, Pseudomonas kilonensis, Pseudomonas knackmussii, Pseudomonas koreensis, Pseudomonas lini, Pseudomonas lutea, Pseudomonas moraviensis, Pseudomonas otitidis, Pseudomonas pachastrellae, Pseudomonas palleroniana, Pseudomonas papaveris, Pseudomonas peli, Pseudomonas perolens, Pseudomonas poae, Pseudomonas pohangensis, Pseudomonas psychrophila, Pseudomonas psychrotolerans, Pseudomonas rathonis, Pseudomonas reptilivora, Pseudomonas resiniphila, Pseudomonas rhizosphaerae, Pseudomonas rubescens, Pseudomonas salomonii, Pseudomonas segitis, Pseudomonas septica, Pseudomonas simiae, Pseudomonas suis, Pseudomonas thermotolerans, Pseudomonas tremae, Pseudomonas trivialis, Pseudomonas turbinellae, Pseudomonas tuticorinensis, Pseudomonas umsongensis, Pseudomonas vancouverensis, Pseudomonas vranovensis, Pseudomonas xanthomarina; Rahnella* species, *Ralstonia* species: *Ralstonia basilensis, Ralstonia campinensis, Ralstonia eutropha, Ralstonia gilardii, Ralstonia insidiosa, Ralstonia mannitolilytica, Ralstonia metallidurans, Ralstonia paucula, Ralstonia pickettii, Ralstonia respiraculi, Ralstonia solanacearum, Ralstonia syzygii, Ralstonia taiwanensis; Raoultella* species, *Rhodoblastus* species, *Rhodopseudomonas* species, *Rhinoscleroma, Rhizobium radiobacter, Rhodococcus equi, Rickettsia* species: *Rickettsia africae, Rickettsia akari, Rickettsia australis, Rickettsia conorii, Rickettsia felis, Rickettsia japonica, Rickettsia mooseri, Rickettsia prowazekii* (Typhus fever), *Rickettsia rickettsii, Rickettsia siberica, Rickettsia typhi, Rickettsia conorii, Rickettsia africae, Rickettsia psittaci, Rickettsia quintana, Rickettsia rickettsii, Rickettsia trachomae; Rothia dentocariosa, Salmonella* species: *Salmonella arizonae, Salmonella Bongori, Salmonella enterica, Salmonella enteriditis, Salmonella paratyphi, Salmonella typhi* (Typhoid fever), *Salmonella typhimurium, Salmonella salamae, Salmonella arizonae, Salmonella diarizonae, Salmonella houtenae, Salmonella indica; Samsonia* species, *Serratia* species: *Serratia entomophila, Serratia ficaria, Serratia fonticola, Serratia grimesii, Serratia liquefaciens, Serratia marcescens, Serratia odoriferae, Serratia plymuthica, Serratia proteamaculans, Serratia quinivorans, Serratia rubidaea, Serratia ureilytica; Shewanella putrefaciens, Shigella boydii, Shigella dysenteriae, Shigella flexneri, Shigella sonnei, Sodalis* species, *Spirillum* species: *Spirillum minus* rat bite fever, *Staphylococcus* species: *Staphylococcus aureus, Staphylococcus auricularis, Staphylococcus capitis, Staphylococcus caprae, Staphylococcus cohnii, Staphylococcus epidermidis, Staphylococcus felis, Staphylococcus haemolyticus, Staphylococcus*

*hominis, Staphylococcus intermedius, Staphylococcus lugdunensis, Staphylococcus pettenkoferi, Staphylococcus saprophyticus, Staphylococcus schleiferi, Staphylococcus simulans, Staphylococcus vitulus, Staphylococcus warneri, Staphylococcus xylosus; Stenotrophomonas* species: *Stenotrophomonas acidaminiphila, Stenotrophomonas dokdonensis, Stenotrophomonas koreensis, Stenotrophomonas maltophilia, Stenotrophomonas nitritireducens, Stenotrophomonas rhizophila; Streptobacillus* species: *Streptobacillus moniliformis* (Streptobacillary rat bite fever); *Streptococcus* species: *Streptococcus* Group A, *Streptococcus* Group B, *Streptococcus agalactiae, Streptococcus aginosus, Streptococcus avium, Streptococcus bovis, Streptococcus canis, Streptococcus cricetus, Streptococcus faceium, Streptococcus faecalis, Streptococcus ferus, Streptococcus gallinarum, Streptococcus lactis, Streptococcus milleri, Streptococcus mitior, Streptococcus mitis, Streptococcus mutans, Streptococcus oralis, Streptococcus peroris, Streptococcus pneumoniae, Streptococcus pyogenes, Streptococcus ratti, Streptococcus salivarius, Streptococcus sanguinis, Streptococcus sobrinus, Streptococcus parasanguinis, Streptococcus suis, Streptococcus thermophilus, Streptococcus vestibularis, Streptococcus viridans, Streptococcus uberis, Streptococcus zooepidemicus; Tatumella* species, *Trabulsiella* species, *Treponema* species: *Treponema carateum* (Pinta), *Treponema denticola, Treponema endemicum* (Bejel), *Treponema pallidum* (Syphilis), *Treponema pertenue* (Yaws); *Tropheryma whipplei* (Whipple disease), Tuberculoid leprosy, *Ureaplasma urealyticum, Veillonella, Vibrio* species: *Vibrio aerogenes, Vibrio aestuarianus, Vibrio agarivorans, Vibrio albensis, Vibrio alginolyticus, Vibrio brasiliensis, Vibrio calviensis, Vibrio campbellii, Vibrio chagasii, Vibrio cholerae* (Cholera), *Vibrio cincinnatiensis, Vibrio Comma, Vibrio coralliilyticus, Vibrio crassostreae, Vibrio cyclitrophicus, Vibrio diabolicus, Vibrio diazotrophicus, Vibrio ezurae, Vibrio fischeri, Vibrio fluvialis, Vibrio fortis, Vibrio furnissii, Vibrio gallicus, Vibrio gazogenes, Vibrio gigantis, Vibrio halioticoli, Vibrio harveyi, Vibrio hepatarius, Vibrio hispanicus, Vibrio ichthyoenteri, Vibrio kanaloae, Vibrio lentus, Vibrio litoralis, Vibrio logei, Vibrio mediterranei, Vibrio metschnikovii, Vibrio mimicus, Vibrio mytili, Vibrio natriegens, Vibrio navarrensis, Vibrio neonatus, Vibrio neptunius, Vibrio nereis, Vibrio nigripulchritudo, Vibrio ordalii, Vibrio orientalis, Vibrio pacinii, Vibrio parahaemolyticus, Vibrio pectenicida, Vibrio penaeicida, Vibrio pomeroyi, Vibrio ponticus, Vibrio proteolyticus, Vibrio rotiferianus, Vibrio ruber, Vibrio rumoiensis, Vibrio salmonicida, Vibrio scophthalmi, Vibrio splendidus, Vibrio superstes, Vibrio tapetis, Vibrio tasmaniensis, Vibrio tubiashii, Vibrio vulnificus, Vibrio wodanis, Vibrio xuii; Vogesella indigofera, Wigglesworthia* species, *Wolbachia* species, *Xenorhabdus* species, *Yersinia enterocolitica, Yersinia pestis, Yersinia pseudotuberculosis*, and *Yokenella* species.

In a preferred embodiment, the antibacterial activity is directed against one or more pathogenic bacteria. More preferred, the antibacterial activity is directed against the bacteria selected from the group comprising *Pseudomonas, Enterococcus, Listeria, Bacillus, Staphylococcus, Escherichia, Salmonella* and *Clostridium*. In an even more preferred embodiment the bacteria are selected from the group comprising *Pseudomonas aeruginosa, Enterococcus faecalis, Listeria monocytogenes, Bacillus cereus, Staphylococcus aureus, Escherichia coli, Salmonella berta, Clostridium perfringens* and *Clostridium bifermentans*.

In another embodiment the antibacterial activity is directed against on or more bacteria resistant to one or more conventional antibiotics. Examples of resistant or multiresistant bacteria include but are not limited to meticillin-resistant *S. aureus*, and multiresistant *P. aeruginosa, Klebsiella pneumoniae* and *Acinetobacter*.

Methicillin Resistant *Staphylococcus aureus* (MRSA)

The strain is resistant to all β-lactam antibiotics. The treatment of MRSA is therefore difficult. The strain can cause both local and systemic infections.

*Klebsiella pneumoniae*, Multiresistant Clinical Isolate

The strain has a plasmid-mediated, broad spectrum β-lactamase (*Klebsiella Pneumoniae* Carbapenemase (KPC) and is resistant to all clinical relevant β-lactam antibiotics. Furthermore, it is in vitro resistant to many other non β-lactam antibiotics. Infections with such microbes are difficult to treat with available antibiotics. *K. pneumoniae* is a common cause of urinary tract infections, but can also cause systemic infections.

*Pseudomonas aeruginosa*, Multiresistant Clinical Isolate

*P. aeruginosa* is naturally resistant to a range of different antibiotics, and the spectre of efficient agents is narrow. Additionally, it has a high ability to develop resistance to new antibiotics. The actual strain is in vitro resistant to, or has reduced susceptibility to antimicrobial agents commonly used in the treatment of *P. aeruginosa* infections. Severe infections with *P. aeruginosa* occur with immune deficient patients and with weak, hospitalized patients.

*Acinetobacter*, Multiresistant Clinical Isolate

*Acinetobacter* is naturally resistant to a range of different antibiotics, and the spectre of efficient agents is narrow. With one exception, the actual isolate in vitro resistant to, or have reduced susceptibility to all antimicrobial agents used for treatment of *Acinetobacter* infections. Severe infections with *Acinetobacter* occur with immune deficient patients and with weak, hospitalized patients.

Fungi

In one embodiment the antimicrobial activity of the composition of the present invention is directed against a fungus, i.e. it is an antifungal. Some examples of fungi include yeasts, molds and mushrooms.

In one embodiment the antifungal activity is directed against one or more pathogenic fungi selected from the group consisting of, but not limited to *Candida, Aspergillus, Cryptococcus, Histoplasma, Pneumocystis, Stachybotrys*.

In one embodiment the antifungal activity is directed against one or more non-pathogenic fungi.

In a preferred embodiment, the antifungal activity is directed against a yeast, more preferred against *Saccharomyces cerevisiae*.

In another preferred embodiment the antifungal activity is directed against a mold, more preferred against *Aspergillus niger*.

In one embodiment, the antifungal activity is not directed against *Candida albicans*.

Virus

In one embodiment the present invention relates to treatment of one or more diseases caused by one or more vira such as one or more vira selected from the group consisting of Abelson murine leukemia virus (Ab-MLV, A-MuLV), acute laryngotracheobronchitis virus (or HPIV), Adelaide River virus, Adeno-associated virus group (Dependevirus), Adenovirus, African horse sickness virus, African swine fever virus, AIDS virus, Aleutian mink disease, parvovirus, alfalfa mosaic virus, Alphaherpesvirinae (including HSV 1 and 2 and varicella), Alpharetrovirus (Avian leukosis virus, Rous sarcoma virus), Alphavirus, alkhurma virus, ALV related virus, Amapari virus, Andean potato mottle virus, Aphthovirus, Aquareovirus, arbovirus, arbovirus C, arbovirus group A, arbovirus group B, Arenavirus group, Argentine hemorrhagic fever virus, Argentinian hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, Avian leukosis virus (ALV), avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus (Cercopithecine herpesvirus 1), B19 virus (Parvovirus B19), Babanki virus, baboon herpesvirus, bacterial virus, baculovirus, barley yellow dwarf virus, Barmah Forest virus, bean pod mottle virus, bean rugose mosaic virus, Bebaru virus, Berrimah virus, Betaherpesvirinae, betaretrovirus, Bird flu, Birnavirus, Bittner virus, BK virus, Black Creek Canal virus, bluetongue virus, Bolivian hemorrhagic fever virus, Borna disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, bracovirus, broad bean mottle virus, broad bean stain virus, brome mosaic virus, Bromovirus, Buggy Creek virus, bullet shaped virus group, Bunyamwera virus, Bunyavirus, Burkitt's lymphoma virus, Bwamba Fever, Bwattany hetero virus, CA virus (Croup-associated virus/parainfluenza vius type 2), Calicivirus, California encephalitis virus, camelpox virus, canarypox virus, canid A herpesvirus, canine coronavirus, canine distemper virus, canine herpesvirus, canine minute virus, canine parvovirus, Cano Delgadito virus, Capillovirus, caprine arthritis virus, caprine encephalitis virus, Caprine Herpes Virus, Capripox virus, Cardiovirus, Carlavirus, Carmovirus, carrot mottle virus, Cassia yellow blotch virus, Caulimovirus, Cauliflower mosaic virus, caviid herpesvirus 1, Cercopithecine herpesvirus 1, Cercopithecine herpesvirus 2, cereal yellow dwarf virus, Chandipura virus, Changuinola virus, channel catfish virus, Charleville virus, chickenpox virus, Chikungunya virus, chimpanzee herpesvirus, Chordopoxyirinae, chub reovirus, chum salmon virus, Closterovirus, Cocal virus, Coho salmon virus, coital exanthema virus, Colorado tick fever virus, Coltivirus Columbia SK virus, Commelina yellow mottle virus, Common cold virus, Comovirus, Condylomata accuminata, congenital cytomegalovirus, contagious eethyma virus, contagious pustular dermatitis virus, Coronavirus, Corriparta virus, coryza virus, cowpea chlorotic mottle virus, cowpea mosaic virus, cowpea virus, cowpox virus, coxsackie virus, CPV (cytoplasmic polyhedrosis virus), cricket paralysis virus, Crimean-Congo hemorrhagic fever virus, croup associated virus, Crypotovirus, Cucumovirus, Cypovirus, Cytomegalovirus (HCMV or Human Herpesvirus 5 HHV-5), cytoplasmic polyhedrosis virus, Cytorhabdovirus, deer papillomavirus, Deltaretrovirus (Human T-lymphotropic virus), Deformed wing virus DWV, Dengue, Densovirus, Dependovirus, Dhori virus, Dianthovirus, diplorna virus, DNA virus, Dobrava-Belgrade Virus, Dog Flu, Drosophila C virus, duck hepatitis B virus, duck hepatitis virus 1, duck hepatitis virus 2, duovirus, Duvenhage virus, eastern equine encephalitis virus, eastern equine encephalomyelitis virus, Ebola virus, Ebola-like virus, Echovirus, echovirus 10, echovirus 28, echovirus 9, ectromelia virus, EEE virus (Eastern equine encephalitis virus), EIA virus (equine infectious anemia), EMC virus (Encephalomyocarditis), Emiliania huxleyi virus 86, encephalitis virus, encephalomyocarditis virus, Endogenous retrovirus, Enterovirus, Entomopoxyirinae, Entomopoxvirus A, Entomopoxvirus B, Entomopoxvirus C, enzyme elevating virus, epidemic hemorrhagic fever virus, epizootic hemorrhagic disease virus, Epsilonretrovirus, Epstein-Barr virus (EBV; Human herpesvirus 4 HHV-4), equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, Fabavirus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Fijivirus, Filovirus, Flanders virus, Flavivirus, foot and mouth disease virus, Fort Morgan virus, Four Corners hantavirus, fowl adenovirus 1, Fowlpox virus, Friend virus, Furovirus, Gammaherpesvirinae, gammaretrovirus, GB virus C (GBV-C; formerly Hepatitis G virus), Geminivirus, German measles virus, Getah virus, gibbon ape leukemia virus, green monkey virus (mullburg), glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantavirus, hard clam reovirus, hare fibroma virus, HCMV (human cytomegalovirus), helper virus, hemadsorption virus 2, hemagglutinating virus of Japan, hemorrhagic fever virus, Hendra virus, Henipaviruses, Hepadnavirus, hepatitis A virus, hepatitis B virus, hepatitis C virus, hepatitis D (delta) virus, hepatitis E virus, hepatitis F virus, hepatitis G virus, hepatitis nonA nonB virus, hepatoencephalomyelitis reovirus 3, Hepatovirus, heron hepatitis B virus, herpes B virus, Herpes simplex virus, herpes simplex virus 1, herpes simplex virus 2, Herpesvirus, Herpes zoster, Herpes virus 6, Herpes virus 7, Herpes virus 8, Herpesvirus ateles, Herpesvirus hominis, Herpesvirus saimiri, Herpesvirus suis, Herpesvirus varicellae, Highlands J virus, Hirame rhabdovirus, HIV-1, hog cholera virus, Hordeivirus, Horse Flu, HTLV-1, HTLV-2, human adenovirus 2, human alphaherpesvirus 1, human alphaherpesvirus 2, human alphaherpesvirus 3, human B lymphotropic virus, human betaherpesvirus 5, human coronavirus, Human enterovirus A, Human enterovirus B, Human Flu, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus (HIV), human immunodeficiency virus 1, human immunodeficiency virus 2, Human metapneumovirus, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, ichnovirus, llarvirus, infantile gastroenteritis virus, infectious bovine rhinotracheitis virus, infectious haematopoietic necrosis virus, infectious pancreatic necrosis virus, influenza virus, influenzavirus A, influenzavirus B, influenzavirus C, influenzavirus D, influenzavirus pr8, insect iridescent virus, insect virus, interfering virus, iridovirus, Isavirus, Japanese B virus, Japanese encephalitis virus, JC virus, Junin virus, Johnson grass mosaic virus, Kaposi's sarcoma-associated herpesvirus, Kemerovo virus, Kilham's rat virus, Klamath virus, Kolongo virus, Korean hemorrhagic fever virus, kumba virus, Kumlinge virus, Kunjin virus, Kyasanur forest disease, Kyzylagach virus, La Crosse virus, lactic dehydrogenase elevating virus, Lagos bat virus, Lambda phage, langat virus, Langur virus, lapine parvovirus, Lassa fever virus, Lassa virus, latent rat virus, LCM virus, Leaky virus, Lentivirus, Leporipoxvirus, leukemia virus, leukovirus, louping ill virus, lumpy skin disease virus, Luteovirus, lymphadenopathy associated virus, Lymphocytic choriomeningitis virus (LCMV), Lymphocryptovirus, lymphocytic choriomeningitis virus, lymphoproliferative virus group, Lyssavirus, Machupo virus, mad itch virus, maize chlorotic dwarf virus, maize rough dwarf virus, mammalian type B oncovirus group, mammalian type B retroviruses, mammalian type C retrovirus group, mammalian type D retroviruses, mammary tumor virus, Mapuera virus, Marafivirus, Marburg virus, Marburg-like virus, Mason Pfizer monkey virus, Mastadenovirus, Mayaro virus, ME virus, Measles virus, Melandrium yellow fleck virus, Menangle virus, Mengo virus, Mengovirus, Merkel cell polyomavirus, Middelburg virus, milkers nodule virus, mink enteritis virus, minute virus of mice, MLV related virus, MM virus, Mokola virus, Molluscipoxvirus, Molluscum contagiosum virus, Moloney murine leukemia virus (M-MuLV), monkey B virus, Monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, Sal mucosal disease virus, Mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Necrovirus, Neethling virus, Nelson Bay virus, NemtickVirus, Nepovirus, neurotropic virus, New World Arenavirus, newborn pneumonitis virus, Newcastle disease virus, Nipah virus, noncytopathogenic virus, Norovirus, Norwalk virus, nuclear polyhedrosis virus (NPV), nipple neck virus, O'nyong'nyong virus, oat sterile dwarf virus, Ockelbo virus, Omsk hemorrhagic fever virus, oncogenic virus, oncogenic viruslike particle, oncornavirus, Orbivirus, Orf virus, Oropouche virus, Orthohepadnavirus, orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, Parainfluenza virus human (HPIV), parainfluenza virus type 1 human (HPIV-1), parainfluenza virus type 2 human (HPIV-2), parainfluenza virus type 3 human (HPIV-3), parainfluenza virus type 4 human (HPIV-4), Paramyxovirus, Parapoxvirus, paravaccinia virus, parsnip yellow fleck virus, Parvovirus, Parvovirus B19, pea enation mosaic virus, Pestivirus, Phlebovirus, phocine distemper virus, Phytoreovirus, Picodnavirus, Picornavirus, pig cytomegalovirus, pigeonpox virus, Piry virus, Pixuna virus, plant rhabdovirus group, plant virus, pneumonia virus of mice, Pneumovirus, Poliomyelitis virus, Poliovirus, Polydnavirus, polyhedral virus, Polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, Potato leaf roll virus, Potato mop top virus, Potato virus Y, Potexvirus, Potyvirus, Powassan encephalitis virus, Poxvirus, poxvirus variolae, Prospect Hill virus, provirus, pseudocowpox virus, pseudorabies virus, psittacinepox virus, Puumala virus, Qalyub virus, Quail pea mosaic virus, quailpox virus, Queensland fruitfly virus, Quokkapox virus, rabbit fibroma virus, rabbit kidney vaculolating virus, rabbit papillomavirus, Rabies virus, raccoon parvovirus, raccoonpox virus, radish mosaic virus, Ranikhet virus, rat cytomegalovirus, rat parvovirus, rat virus, Rauscher's virus, recombinant vaccinia virus, recombinant virus, Red Clover Necrotic Mosaic Virus, reovirus, reovirus 1, reovirus 2, reovirus 3, reptilian type C virus, Respiratory syncytial virus, respiratory virus, reticuloendotheliosis virus, Retrovirus, Rhabdovirus, Rhabdovirus carpia, Rhadinovirus, Rhinovirus, Rhizidiovirus, rice dwarf virus, rice gall dwarf virus, rice hoja blanca virus, rice ragged stunt virus, Rift Valley fever virus, Riley's virus, rinderpest virus, RNA tumor virus, RNA virus, Roseolovirus, Ross River virus, Rotavirus, rougeole virus, Rous sarcoma virus, Rubella virus, rubeola virus, Rubivirus, Russian autumn encephalitis virus, S6-14-03 virus, SA 11 simian virus, SA 15, SA2 virus, SA6 virus, SA8 virus, Sabia virus, Sabio virus, Sabo virus, Saboya virus, *Sabulodes caberata* GV, Sacbrood virus, *Saccharomyces cerevisiae* virus L-A, *Saccharomyces cerevisiae* virus La, *Saccharomyces cerevisiae* virus LBC, Sagiyama virus, Saguaro cactus virus, Saimiriine herpesvirus 1, Saimiriine herpesvirus 2, Sainpaulia leaf necrosis virus, SaintAbb's Head virus, Saint-Floris virus, Sakhalin virus, Sal Vieja virus, Salanga virus, Salangapox virus, Salehabad virus, salivary gland virus, Salmonid herpesvirus 1, Salmonid herpesvirus 2, Salmonis virus, Sambucus vein clearing virus, *Samia cynthia* NPV, *Samia pryeri* NPV, *Samia ricini* NPV, Sammons' Opuntia virus, SanAngelo virus, San Juan virus, San Miguel sealion virus, San Perlita virus, Sand rat nuclear inclusion agents, Sandfly fever Naples virus, Sandfly fever Sicilian virus, Sandjimba virus, Sango virus, Santa Rosa virus, Santarem virus, Santosai temperate virus, Sapphire II virus, Sapporo-like virus, Saraca virus, *Sarracenia purpurea* virus, SARS virus, satellite virus, Sathuperi virus, Satsuma dwarf virus, *Saturnia pavonia* virus, *Saturnia pyri* NPV, Saumarez Reef virus, Sawgrass virus, *Sceliodes cordalis* NPV, Schefflera ringspot virus, Sciaphila duplex GV, *Scirpophaga incertulas* NPV, Sciurid herpesvirus, Sciurid herpesvirus 2, *Scoliopteryx libatrix* NPV, *Scopelodes contracta* NPV, *Scopelodes venosa* NPV, *Scopula subpunctaria* NPV, *Scotogramma trifolii* GV, *Scotogramma trifolu* NPV, Scrophularia mottle virus, SDAV (sialodacryoadenitis virus), sealpox virus, *Selenephera lunigera* NPV, Selepa celtis GV, Seletar virus, *Selidosema suavis* NPV, *Semidonta biloba* NPV, *Semiothisa sexmaculata* GV, Semliki Forest Virus, Sena Madureira virus, Sendai virus, SENV-D, SENV-H, Seoul virus, Sepik virus, Serra do Navio virus, Serrano golden mosaic virus, Sesame yellow mosaic virus, *Sesamia calamistis* NPV, *Sesamia cretica* GV, *Sesamia inferens* NPV, *Sesamia nonagrioides* GV, *Setora nitens* virus, Shallot latent virus, Shamonda virus, Shark River virus, Sheep associated malignant catarrhal fever, Sheep papillomavirus, Sheep pulmonary adenomatosis associated herpesvirus, sheeppox virus, Shiant Islands virus, Shokwe virus, Shope fibroma virus, Shope papilloma virus, Shuni virus, Siamese cobra herpesvirus, Sibine fusca densovirus, Sida golden mosaic virus (SiGMV), Sida golden yellow vein virus (SiGYVV), Sigma virus, Sikte water-borne virus, Silverwater virus, Simbu virus, Simian adenoviruses 1 to 27, Simian agent virus 12, Simian enterovirus 1 to 18, simian foamy virus, Simian hemorrhagic fever virus, simian hepatitis A virus, simian human immunodeficiency virus, simian immunodeficiency virus, simian parainfluenza virus, Simian rotavirus SA11, Simian sarcoma virus, simian T cell lymphotrophic virus, Simian type D virus 1, Simian vancella herpesvirus, simian virus, simian virus 40, Simplexvirus, *Simulium vittatum* densovirus, Sin Nombre virus, Sindbis virus, Sint1em's onion latent virus, Sixgun city virus, Skunkpox virus, Smallpox virus, Smelt reovirus, *Smerinthus ocellata* NPV, Smithiantha virus, Snakehead rhabdovirus, Snowshoe hare virus, Snyder-Theilen feline sarcoma virus, Sobemovirus, Sofyn virus, Soil-borne wheat mosaic virus, Sokoluk virus, *Solanum apical* leaf curl virus, *Solanum nodiflorum* mottle virus, Solanurn yellows virus, Soldado virus, Somerville virus 4, Sonchus mottle virus, Sonchus virus, Sonchus yellow net virus, Sorghum chlorotic spot virus, Sorghum mosaic virus, Sorghum virus, Sororoca virus, Soursop yellow blotch virus, South African passiflora virus, South American hemorrhagic fever viruses, South African passiflora virus, South River virus, Southern bean mosaic virus, Southern potato latent virus, Sowbane mosaic virus, Sowthistle yellow vein virus, Soybean chlorotic mottle virus, Soybean crinkle leaf virus, Soybean dwarf virus, Soybean mosaic virus, SPAr-2317 virus, *Sparganothis pettitana* NPV, sparrowpox virus, Spartina mottle virus, Spectacled caimanpox virus, SPH 114202 virus, Sphenicid herpesvirus 1, *Sphinx ligustri* NPV, Spider monkey herpesvirus, *Spilarctia subcarnea* NPV, *Spilonota ocellana* NPV, *Spilosoma lubricipeda* NPV, Spinach latent virus, Spinach temperate virus, *Spiroplasma* phage 1, *Spiroplasma* phage 4, *Spiroplasma* phage aa, *Spiroplasma* phage C1/T52, *Spodoptera exempta* cypovirus, *Spodoptera exigua* virus, *Spodoptera frugiperda* virus, *Spodoptera latifascia* virus, *Spodoptera littoralis*, *Spodoptera mauritia* virus, *Spodoptera ornithogalli* virus, Spondweni virus, spring beauty latent virus, Spring viremia of carp virus, Spumavirus (SFV, HFV), Squash leaf curl virus, squash mosaic virus, squirrel fibroma virus, Squirrel monkey herpesvirus, squirrel monkey retrovirus, SR-11 virus, Sri Lankan passionfruit mottle virus, Sripur virus, SSV 1 virus group, StAbbs Head virus, St. Louis encephalitis virus, *Staphylococcus* phage 107, *Staphylococcus* phage 187, *Staphylococcus* phage 2848A, *Staphylococcus* phage 3A, *Staphylococcus* phage 44A HJD, *Staphylococcus* phage 77, *Staphylococcus* phage B11-M15, *Staphylococcus* phage Twort, Starlingpox virus, Statice virus Y, P, STLV (simian T lymphotropic virus) type I, STLV (simian T lymphotropic virus) type II, STLV (simian T lymphotropic virus) type III, stomatitis papulosa virus, Stratford virus, Strawberry crinkle virus, Strawberry latent ringspot virus, Strawberry mild yellow edge virus, Strawberry vein banding virus, *Streptococcus* phage 182, *Streptococcus* phage 2BV, *Streptococcus* phage A25, *Streptococcus* phage 24, *Streptococcus* phage PE1, *Streptococcus* phage VD13, *Streptococcus phage fD*8, *Streptococcus* phage CP-1, *Streptococcus* phage Cvir, *Streptococcus* phage H39, Strigid herpesvirus 1, Striped bass reovirus, Striped Jack nervous, necrosis virus, Stump-tailed macaque virus, submaxillary virus, Subterranean clover mottle virus, Subterranean clover mottle virus satellite, Subterranean clover red leaf virus, Subterranean clover stunt virus, Sugarcane bacilliform virus, Sugarcane mild mosaic virus, Sugarcane mosaic virus, Sugarcane streak virus, suid alphaherpesvirus 1, suid herpesvirus 2, Suipoxvirus, Sulfolobus virus 1, Sunday Canyon virus, Sunflower crinkle virus, Sunflower mosaic virus, Sunflower rugose mosaic virus, Sunflower yellow blotch virus, Sunflower yellow ringspot virus, Sun-hemp mosaic virus, swamp fever virus, Sweet clover necrotic mosaic virus, Sweet potato A virus, Sweet potato chlorotic leafspot virus, Sweet potato feathery mottle virus, Sweet potato internal cork virus, Sweet potato latent virus, Sweet potato mild mottle virus, Sweet potato russet crack virus, Sweet potato vein mosaic virus, Sweet potato yellow dwarf virus, Sweetwater Branch virus, Swine cytomegalovirus, Swine Flu, Swine infertility and respiratory syndrome virus, swinepox virus, Swiss mouse leukemia virus, Sword bean distortion mosaic virus, *Synaxis jubararia* NPV, *Synaxis pallulata* NPV, *Synetaeris tenuifemur* virus, *Syngrapha selecta* NPV, T4 phage, T7 phage, TAC virus, Tacaiuma virus, Tacaribe complex virus, Tacaribe virus, Tadpole edema virus LT 1-4, Taggert virus, Tahyna virus, Tai virus, Taiassui virus, Tamana bat virus, Tamarillo mosaic virus, Tamdy virus, [[Tamiami virus, Tanapox virus, Tanga virus, Tanjong Rabok virus, Taro bacilliform virus, Badnavirus Tataguine virus, Taterapox virus, Taterapox virus, Teasel mosaic virus, Tehran virus, Telfairia mosaic virus, Telok Forest virus, Tembe virus, Tembusu virus, Tench reovirus, Tensaw virus, Tenvivirus, Tephrosia symptomless virus, Termeil virus, Tete virus, *Tetralopha scortealis* NPV, *Tetropium cinnamoptemm* NPV, Texas pepper virus, Thailand virus, *Thaumetopoea pityocampa* virus, Theiler's encephalomyelitis virus, Theiler's virus, *Theophila mandarina* NPV, *Theretra japonica* NPV, *Thermoproteus* virus 1, *Thermoproteus* virus 2, *Thermoproteus* virus 3, *Thermoproteus* virus 4, Thiafora virus, Thimiri virus, Thistle mottle virus, Thogoto virus, Thormodseyjarklettur virus, Thosea asigna virus, *Thosea baibarana* NPV, *Thosea sinensis* GV, Thottapalayam virus, *Thylidolpteryx ephemeraeformis* NPV, *Thymelicus lineola* NPV, Tibrogargan virus, *Ticera castanea* NPV, Tick borne encephalitis virus (TBEV)—European and Far Eastern subtypes, Tillamook virus, Tilligerry virus, Timbo virus, Tilmboteua virus, Tilmaroo virus, Tindholmur virus, *Tinea pellionella* NPV, *Tineola hisselliella* NPV, *Tinpula paludosa* NPV, *Tinracola plagiata* NPV, Tioman virus, Tlacotalpan virus, Tobacco bushy top virus, Tobacco etch virus, Tobacco leaf curl virus, Tobacco mild green mosaic virus, tobacco mosaic virus, Tobacco mosaic virus satellite, Tobacco mottle virus, Tobacco necrosis virus, Tobacco necrosis virus satellite, Tobacco necrosis virus small satellite, Tobacco necrotic dwarf virus, tobacco rattle virus, Tobacco ringspot virus, Tobacco streak virus, Tobacco stunt virus, Tobacco vein banding mosaic virus, Tobacco vein distorting virus Tobacco vein mottling virus, Tobacco wilt virus, Tobacco yellow dwarf virus, Tobacco yellow net virus, Tobacco yellow vein virus, Tobamovirus Tobravirus, Togavirus, Tomato apical stunt viroid, Tomato aspermy virus, Tomato black ring virus, Tomato black ring virus satellite, Tomato bunchy top viroid, tomato bushy stunt virus, Tomato bushy stunt virus satellite, Tomato golden mosaic virus, Tomato leaf crumple virus, Tomato leaf curl virus, Tomato leafroll virus, Tomato mosaic virus, Tomato mottle virus, Tomato pale chlorosis virus, Tomato planta macho viroid, Tomato pseudo-curly top virus, Tomato ringspot virus, Tomato spotted wilt virus, Tomato top necrosis virus, Tomato vein yellowing virus, Tomato yellow dwarf virus, Tomato yellow leaf curl virus, Tomato yellow mosaic virus, Tomato yellow top virus, Tombusvirus, Tongan vanilla virus, Torovirus, Torque teno virus, *Tortrix loeflingiana* NPV, *Tortrix viridana* NPV, Toscana virus, Tospovirus, *Toxorhynchites brevipalpis* NPV, *Trabala vishnou* NPV, Tradescantia/Zebrina virus, Trager duck spleen necrosis virus, *Tranosema* sp. Virus, transforming virus, Tree shrew adenovirus 1, Tree shrew herpesvims, *Triatoma* virus, Tribec virus, *Trichiocampus irregularis* NPV, *Trichiocampus viminalis* NPV, *Trichomonas vaginalis* virus, *Trichoplusia ni* cypovirus 5, *Trichoplusia ni* granulovirus, *Trichoplusia ni* MNPV, *Trichoplusia ni* Single SNPV, *Trichoplusia ni* virus, Trichosanthes mottle virus, *Triticum aestivum* chlorotic spot virus, Trivittatus virus, Trombetas virus, Tropaeolum virus 1, Tropaeolum virus 2, Trubanarnan virus, Tsuruse virus, Tucunduba virus, Tulare apple mosaic virus, Tulip band breaking virus, Tulip breaking virus, Tulip chlorotic blotch virus, Tulip top breaking virus, Tulip virus X, tumor virus, Tupaia virus, Tupaiid herpesvirus 1, Turbot herpesvirus, Turbot reovirus, Turkey adenoviruses 1 to 3, Turkey coronavirus, Turkey herpesvirus 1, turkey rhinotracheitis virus, turkeypox virus, Turlock virus, Turnip crinkle virus, Turnip crinkle virus satellite, Turnip mild yellows virus, Turnip mosaic virus, Turnip rosette virus, turnip yellow mosaic virus, Turuna virus, Tymovirus, Tyuleniy virus, type C retroviruses, type D oncovirus, type D retrovirus group, Uasin Gishu disease virus, Uganda S virus, *Ugymyia sericariae* NPV, ulcerative disease rhabdovirus, Ullucus mild mottle virus, Ullucus mosaic virus, Ullucus virus C, Umatilla virus, Umbre virus, Una virus, Upolu virus, UR2 sarcoma virus, *Uranotaenia sapphirina* NPV, *Urbanus proteus* NPV, Urucuri virus, *Ustilago maydis* virus 1, *Ustilago maydis* virus 4, *Ustilago maydis* virus 6, Usutu virus, Uting a virus, Utive virus, Uukuniemi virus group, Vaccinia virus, Vaeroy virus, Vallota mosaic virus, *Vanessa atalanta* NPV, *Vanessa cardui* NPV, *Vanessa prorsa* NPV, Vanilla mosaic virus, Vanilla necrosis virus, Varicella zoster virus, Varicellovirus, Varicola virus, variola major virus, variola virus, Vasin Gishu disease virus, Vellore virus, Velvet tobacco mottle virus, Velvet tobacco mottle virus satellite, Venezuelan equine encephalitis virus, Venezuelan equine encephalomyelitis virus, Venezuelan hemorrhagic fever virus, Vesicular stomatitis virus, Vesiculovirus, *Vibrio* phage 06N-22P, *Vibrio* phage 06N-58P, *Vibrio* phage 4996, *Vibrio* phage a3a, *Vibrio* phage I, *Vibrio* phage II, *Vibrio* phage m, Vibrio phage IV, *Vibrio* phage kappa, *Vibrio* phage nt-1, *Vibrio* phage OXN-52P, *Vibrio* phage OXN-IOOP, *Vibrio* phage v6, *Vibrio* phage Vfl2, *Vibrio* phage Vf33, *Vibrio* phage VP1, *Vibrio* phage VP11, *Vibrio* phage VP3, *Vibrio* phage VP5, *Vibrio* phage X29, Vicia cryptic virus, Vigna sinensis mosaic virus, Vilyuisk virus, Vinces virus, Viola mottle virus, viper retrovirus, viral haemorrhagic septicemia virus, virus-like particle, Visna Maedi virus, Visna virus, Voandzeia mosaic virus, Voandzeia necrotic mosaic virus, volepox virus, Wad Medani virus, Wallal virus, Walleye epidermal hyperplasia, Walrus calicivirus, Wanowrie virus, Warrego virus, Watermelon chlorotic stunt virus, Watermelon curly mottle virus, Watermelon mosaic virus 1, Watermelon mosaic virus 2, Weddel water-borne virus, Weldona virus, Wesselsbron virus, West Nile virus, western equine encephalitis virus, western equine encephalomyelitis virus, Wexford virus, Whataroa virus, Wheat American striate mosaic virus, Wheat chlorotic streak virus, Wheat dwarf virus, Wheat rosette stunt virus, Wheat streak mosaic virus, Wheat yellow leaf virus, Wheat yellow mosaic virus, White bryony virus, White clover cryptic virus 1, White clover cryptic virus 2, White clover cryptic virus 3, White clover mosaic virus, White lupinrnosaic virus, Wild cucumber mosaic virus, Wild potato mosaic virus, Wildbeest herpesvirus, Wineberry latent virus, Winter wheat mosaic virus, Winter wheat Russian mosaic virus, *Wiseana cervinata* virus, *Wiseana signata* virus, *Wiseana umbraculata* virus, Wissadula mosaic virus, Wisteria vein mosaic virus, Witwatersrand virus, Wongal virus, Wongorr virus, Winter Vomiting Virus, woodchuck hepatitis B virus, Woodchuck herpesvirus marmota 1, woolly monkey sarcoma virus, wound tumor virus, WRSV virus, WVU virus 2937, WW virus 71 to 212, *Wyeomyia smithii* NPV, Wyeomyia virus, *Xanthomonas* phage Cf, *Xanthomonas* phage Cflt, *Xanthomonas* phage RR66, *Xanthomonas* phage Xf, *Xanthomonas* phage Xf2, *Xanthomonas* phage XP5, *Xenopus* virus T21, Xiburema virus, Xingu virus, Xylena curvimacula NPV, Y73 sarcoma virus, Yaba monkey tumor virus, Yaba-1 virus, Yaba-7 virus, Yacaaba virus, Yam mosaic virus, Yaounde virus, Yaquina Head virus, Yatapoxvirus, Yellow fever virus, Yogue virus, Yokapox virus, Yokase virus, *Yponomeuta cognatella* NPV, *Yponomeuta evonymella* NPV, *Yponomeuta malinellus* NPV, *Yponomeuta padella* NPV, *Yucca baciliform* virus, Yug Bogdanovac virus, Zaliv Terpeniya virus, *Zea mays* virus, Zegla virus, *Zeiraphera diniana* virus, *Zeiraphera pseudotsugana* NPV, Zika virus, Zirqa virus, Zoysia mosaic virus, Zucchini yellow fleck virus, Zucchini yellow mosaic virus, and Zygocactus virus.

Microbial Infections

In one embodiment the present invention relates to treatment of one or more microbial infectious diseases by administration of the composition according to the present invention to an individual in need thereof. The infectious disease can be any type of infection including the types of infections mentioned elsewhere herein and those listed in Tables 1, 2, 3, or 4 herein below.

TABLE 1

Human diseases caused by bacteria

| Disease | Casual Agent |
|---|---|
| Strep Throat, Scarlet Fever | *Streptococcus, Pyogenes* |
| Diphtheria | *Corynebacterium diphtheriae* |
| Pertussis (Whooping Cough) | *bordetella pertussis* |
| Meningococcal Meningitis | *Neisseria meningitidis* |
| Haemophilus meningitis | *Haemophilus influenzae* |
| Flavobacterium meningitis | *Flavobacterium meningospecticum* |
| Tuberculosis | *Mycobacterium tuberculosis* |
| Pneumococcal pneumonia | *Sterptococcus pneumoniae* |
| Primary Atypical Pneumonia | *Mycoplasma pneumoniae* |
| Klebsiella pneumonia | *Klebsiella pneumoniae* |
| Serratia pneumonia | *Serratia marcescens* |
| Q Fever | *coxiella burnetti* |
| Psittacosis | *chlamydia psittaci* |
| Botulism | *Clostridium botulinum* |
| Staphylococcal Food Poisoning | *Stephylococcus aureus* |
| Clostridial Food Poisoning | *clostridium perfringes* |
| Typhoid Fever | *Salmonella typhi* |
| Salmonellosis | *Salmonella serotypes* |
| Shigellosis | *shigella serotypes* |
| Cholera | *vibrio cholerae* |
| Brucellosis | *Brucella* Spp. |
| Anthrax | *Bacillus anthracis* |
| Tetanus | *Clostridium tetani* |
| Gas Gangrene | *clostridium perfringes* |
| Bubonic Plague | *yersinia pestis* |
| Relapsing Fever | *Borrelia recurrentis* |
| Rocky Mountain Spotted Fever | *Rickettsia rickettsiae* |
| Epidemic Typhus (Typhus Fever) | *Rickettsia prowazekii* |
| Endemic Typhus (Murine Typhus) | *Rickettsia typhi* |
| Scrub Typhus | *Rickettsia tsutsugamushi* |
| Rickettsialpox | *Rickettsia akari* |
| Tickborne Fevers | *Rickettsia conorii* |
| Syphilis | *Treponema pallidum* |
| Gonorrhea | *Neisseria gonorrhoeae* |
| Chlamydial urethritis | *chlamydia trachomatis* |
| Ureaplasmal urethritis | *Ureaplasma urealyticum* |
| Lymphogranuloma venereum | *Chlamydia trachomatis* |
| Vaginitis | *Gardnerella vaginalis* |
| Mycoplasmal urethritis | *Mycoplasma hominis* |
| Leprosy (hansen's Disease) | *Mycobacterium leprae* |
| Staphylococcal skin diseases | *Staphlococcus aureus* |

TABLE 1-continued

Human diseases caused by bacteria

| Disease | Casual Agent |
|---|---|
| Trachoma | *chlamydia trachomatis* |
| Bacterial Conjuctivitis | *Haemophilus influenze* type III |

TABLE 2

Human diseases caused by virus

| Disease | Causal Agent | Organs Affected |
|---|---|---|
| Influenza | RNA | Respiratory Tract |
| Adenovirus Infections | DNA | Lungs, Eyes |
| Respiratory Syncytial Disease | RNA | Respiratory Tract |
| Rhinovirus Infections | RNA | Upper Respiratory Tract |
| Herpes Simplex | DNA | Skin, Pharynx, Genital organs |
| Chicken pox (Varicella) | DNA | Skin, Nervous System |
| Measles (Rubeola) | RNA | Respiratory Tract, Skin |
| German Measles (Rubella) | RNA | Skin |
| Mumps (Epidemic Parotitis) | RNA | Salivary Glands, Blood |
| Small Pox (Variola) | DNA | Skin, Blood |
| Warts Kawasaki Disease | DNA | Skin |
| Yellow Fever | RNA | Liver, Blood |
| Dengue Fever | RNA | Blood, Muscles |
| Hepatitis A | RNA | Liver |
| Hepatitis B | DNA | Liver |
| NANB Hepatitis | RNA | Liver |
| Viral Gastroenteritis | Many RNA Viruses | Intestine |
| Viral Fevers | Many RNA Viruses | Blood |
| Cytomegalovirus Disease | DNA | Blood, Lungs |
| AIDS | Retrovirus (RNA) | T-lymphocytes |
| Rabies | RNA | Brain, Spinal cord |
| Polio | RNA | Intestine, Brain, Spinal Cord |
| Slow Virus Disease | Prions | Brain |
| Arboviral Enephalitis | Many RNA viruses | Brain |

TABLE 3

Human diseases caused by fungi

| Disease | Casual Agent |
|---|---|
| Cryptococcosis | *Cryptococcus neoformans* |
| Candidiasis, Vaginitis, Thrush, Onychia | *Candida albicans* |
| tinea Pedis | *Trichophyton* Spp. |
| Tinea Captis | *Microsporum* Spp. |
| Tinea Corporis, Tinea Barhae | *Epidermophyton* spp. |
| Histoplasmosis | *Histoplasma capsulatum* |
| Blastomycosis | *Blastomyces dermatitidis* |
| Coccidiodomycosis | *Coccidiodes immitis* |
| Aspergillosis Otomycosis | *Aspergillus* |

TABLE 4

Human diseases caused by protozoa

| Disease | Causal Agent |
|---|---|
| Amoebiasis | *Entamoeba histolytica* |
| Primary Amoebic meningoencephalitis | *Naegleria fowleri* |
| Giardiasis | *Giardia Lamblia* |
| Trichomoniasis | *Trichomonas vaginalis* |

TABLE 4-continued

Human diseases caused by protozoa

| Disease | Causal Agent |
|---|---|
| African Sleeping Sickness | *Trypanosoma brucei* |
| Leishmaniasis (Kala-azar) | *Leishmania donovani* |
| Toxoplasmosis | *Toxoplasma gondii* |
| Malaria | *Plasmodium* spp. |
| Babesiosis | *Babesia microti* |
| Pneumocytosis (PCP) | *Pneumocystis carinii* |

Individual

The individual treated can be a human being or an animal. The animal can be a dog, cat, horse, rabbit, hamster, mouse, rat, monkey, cow, pig, donkey, fish, bird, reptile or any other animal in need of treatment. In one embodiment the animal is a laboratory/test animal. In another embodiment the animal in need of treatment is a pet or livestock such as domesticated cows, pigs, sheep, poultry or farmed fish.

The human being can be a man, a woman, a post-menopausal women, a pregnant woman, a lactating woman, an infant, a child, or an adult. The individual such as a human being can be of any age such as from newborn to 120 years old, for example from 0 to 6 months, such as from 6 to 12 months, for example from 1 to 5 years, such as from 5 to 10 years, for example from 10 to 15 years, such as from 15 to 20 years, for example from 20 to 25 years, such as from 25 to 30 years, for example from 30 to 35 years, such as from 35 to 40 years, for example from 40 to 45 years, such as from 45 to 50 years, for example from 50 to 60 years, such as from 60 to 70 years, for example from 70 to 80 years, such as from 80 to 90 years, for example from 90 to 100 years, such as from 100 to 110 years, for example from 110 to 120 years.

The individual can be of any race such as a Caucasian, a black person, an East Asian person, a person of Mongoloid race, a person of Ethiopian race, a person of Negroid race, a person of American Indian race, a person of Australoid race, or a person of Malayan race.

Said human being or animal can be healthy or have one or more diseases. Said human being or animal can be diagnosed and/or treated for one or more diseases. In one embodiment said individual is genetically disposed for one or more diseases.

In one embodiment, the individual in need of treatment is a individual infected with one or more pathogenic or disease-causing bacteria. Disease-causing bacteria include, but are not limited to the group comprising *Pseudomonas, Enterococcus, Listeria, Bacillus, Staphylococcus, Escherichia, Salmonella* and *Clostridium*. In a preferred embodiment the bacteria are selected from the group comprising *Pseudomonas aeruginosa, Enterococcus faecalis, Listeria monocytogenes, Bacillus cereus, Staphylococcus aureus, Escherichia coli, Salmonella berta, Clostridium perfringens* and *Clostridium bifermentans*.

In one embodiment, the individual in need of treatment is a individual infected with one or more bacteria resistant to one or more antibiotics. Examples of resistant or multiresistant bacteria include but are not limited to meticillin-resistant *S. aureus*, and multiresistant *P. aeruginosa, Klebsiella pneumoniae* and *Acinetobacter.*

In another embodiment, the individual in need of treatment is a individual infected with one or more pathogenic fungi.

Administration Route and Dosage

The composition may be administered using one or more of the following routes of administration.

Routes of administration can broadly be divided into:

Topical: local effect, substance is applied directly where its action is desired.

Enteral: desired effect is systemic (non-local), substance is given via the digestive tract.

Parenteral: desired effect is systemic, substance is given by routes other than the digestive tract.

In one embodiment the antimicrobial composition of the present invention is administered topically.

In one embodiment the antimicrobial composition of the present invention is administered enterally.

In one embodiment the antimicrobial composition of the present invention is administered parentally.

Topical administration include:
Epicutaneous (application onto the skin
Inhalational
Enema
Eye drops (onto the conjunctiva)
Ear drops
Intranasal route (into the nose),
Vaginal Enteral administration is any form of administration that involves any part of the gastrointestinal tract and include:
By mouth (peroral)
By gastric feeding tube, duodenal feeding tube, or gastrostomy
Rectally Parenteral by injection or infusion include:
Intravenous (into a vein)
Intraarterial (into an artery)
Intramuscular (into a muscle),
Intracerebral (into the cerebrum) direct injection into the brain.
Intracerebroventricular (into the cerebral ventricles) administration into the ventricular system of the brain
Intracardiac (into the heart)
Subcutaneous (under the skin),
Intraosseous infusion (into the bone marrow) is, in effect, an indirect intravenous access because the bone marrow drains directly into the venous system.
Intradermal, (into the skin itself)
Intrathecal (into the spinal canal)
Intraperitoneal, (infusion or injection into the peritoneum)
Intravesical infusion is into the urinary bladder.
Intracavernosal injection is into the base of the penis.

Other parenteral administration modes include:
Transdermal (diffusion through the intact skin),
Transmucosal (diffusion through a mucous membrane), e.g. insufflation, sublingual, i.e. under the tongue, vaginal suppositories
Inhalational,
Intracisternal: given between the first and second cervical vertebrae
Other epidural (synonym: peridural) (injection or infusion into the epidural space)
Intravitreal, through the eye Peroral intake may be in the form of
Tablets
Capsules
Mixtures
Liquid
Powder Injections may be either systemic or local injections Other administration modes of the present invention include:
Jet-infusion (micro-drops, micro-spheres, micro-beads) through skin
Drinking solution, suspension or gel
Inhalation
Nose-drops
Eye-drops
Ear-drops
Skin application as ointment, gel, lotion, cream or through a patch
Vaginal application as ointment, gel, crème or washing
Gastro-Intestinal flushing
Rectal washings or by use of suppositories Administration can be performed as
Single administration such as single intake, injection, application, washing
Multiple administrations such as multiple intakes, injections, applications, washings
On single day basis
Over prolonged time as days, month, years Drug dose and regimen can be modified during the course.

A dose or dosage of the composition according to the present invention may be given as a single dose or in divided doses. A single dose occurs only once, with the drug administered either as a bolus or by continuous infusion. Alternatively, the dose may be divided into multiple doses and given recurrently, such as twice (two times), for example three times, such as four times, for example five times, such as six times, for example seven times, such as eight times, for example nine times, such as ten divided doses. Furthermore, the dose may be given repeatedly, i.e. more than once, such as twice (two times), for example three times, such as four times, for example five times, such as six times, for example seven times, such as eight times, for example nine times, such as ten times a day. Alternatively, the dose may be in sustained release form. A bolus is in theory regarded as given immediately, and should be administered in less than 5 minutes.

It follows that the composition according to the present invention may be given once or more daily, or alternatively may be given with intervals of 1 day, such as 2 days, for example 3 days, such as 4 days, such as 5 days, for example 6 days, such as 7 days (1 week), for example 8 days, such as 9 days, such as 10 days, for example 11 days, such as 12 days, for example 13 days, such as 14 days (2 weeks), such as 3 weeks, for example 4 weeks, such as 5 weeks, for example 6 weeks, such as 7 weeks, such as 8 weeks, for example 12 weeks.

In one embodiment the antimicrobial composition according to the present invention is administered to an individual in need thereof at a total daily dosage of from about 0.01 milligram to about 1000 milligram per kilogram of body weight. The dosage regimen may be adjusted within this range or even outside of this range to provide the optimal therapeutic response.

The composition according to the present invention is given in an effective amount to an individual in need thereof. The amount of composition according to the present invention in one preferred embodiment is in the range of from about 0.01 milligram per kg body weight per dose to about 1000 milligram per kg body weight per dose, such as from about 0.01 milligram per kg body weight per dose to about 0.025 milligram per kg body weight per dose, for example from about 0.025 milligram per kg body weight per dose to about 0.05 milligram per kg body weight per dose, such as from about 0.05 milligram per kg body weight per dose to about 0.075 milligram per kg body weight per dose, for example from about 0.075 milligram per kg body weight per dose to about 0.1 milligram per kg body weight per dose, such as from about 0.1 milligram per kg body weight per dose to about 0.25 milligram per kg body weight per dose, such as from about 0.25 milligram per kg body weight per dose to about 0.5 milligram per kg body weight per dose, for example from about 0.5 milligram per kg body weight per dose to about 0.75 milligram per kg body weight per dose, such as from about 0.75 milligram per kg body weight per dose to about 1.0 milligram per kg body weight per dose, for example from about 1.0 milligram per kg body weight per dose to about 2.5 milligram per kg body weight per dose, such as from about 2.5 milligram per kg body weight per dose to about 5 milligram per kg body weight per dose, for example from about 5 milligram per kg body weight per dose to about 7.5 milligram per kg body weight per dose, such as from about 7.5 milligram per kg body weight per dose to about 10 milligram per kg body weight per dose, for example from about 10 milligram per kg body weight per dose to about 25 milligram per kg body weight per dose, such as from about 25 milligram per kg body weight per dose to about 50 milligram per kg body weight per dose, such as from about 50 milligram per kg body weight per dose to about 75 milligram per kg body weight per dose, for example from about 75 milligram per kg body weight per dose to about 100 milligram per kg body weight per dose, such as from about 100 milligram per kg body weight per dose to about 250 milligram per kg body weight per dose, for example from about 250 milligram per kg body weight per dose to about 500 milligram per kg body weight per dose, such as from about 500 milligram per kg body weight per dose to about 750 milligram per kg body weight per dose, for example from about 750 milligram per kg body weight per dose to about 1000 milligram per kg body weight per dose.

The amount of composition according to the present invention in another preferred embodiment is in the range of from about 0.01 milligram per kg body weight per dose to about 20 milligram per kg body weight per dose, such as from about 0.02 milligram per kg body weight per dose to about 18 milligram per kg body weight per dose, for example from about 0.04 milligram per kg body weight per dose to about 16 milligram per kg body weight per dose, such as from about 0.06 milligram per kg body weight per dose to about 14 milligram per kg body weight per dose, for example from about 0.08 milligram per kg body weight per dose to about 12 milligram per kg body weight per dose, such as from about 0.1 milligram per kg body weight per dose to about 10 milligram per kg body weight per dose, such as from about 0.2 milligram per kg body weight per dose to about 10 milligram per kg body weight per dose, for example from about 0.3 milligram per kg body weight per dose to about 10 milligram per kg body weight per dose, such as from about 0.4 milligram per kg body weight per dose to about 10 milligram per kg body weight per dose, for example from about 0.5 milligram per kg body weight per dose to about 10 milligram per kg body weight per dose, such as from about 0.6 milligram per kg body weight per dose to about 10 milligram per kg body weight per dose, for example from about 0.7 milligram per kg body weight per dose to about 10 milligram per kg body weight per dose, such as from about 0.8 milligram per kg body weight per dose to about 10 milligram per kg body weight per dose, for example from about 0.9 milligram per kg body weight per dose to about 10 milligram per kg body weight per dose, such as from about 1.0 milligram per kg body weight per dose to about 10 milligram per kg body weight per dose, for example from about 1.2 milligram per kg body weight per dose to about 10 milligram per kg body weight per dose, such as from about 1.4 milligram per kg body weight per dose to about 10 milligram per kg body weight per dose, for example from about 1.6 milligram per kg body weight per dose to about 10 milligram per kg body weight per dose, such as from about 1.8 milligram per kg body weight per dose to about 10 milligram per kg body weight per dose, for example from about 2.0 milligram per kg body weight per dose to about 10 milligram per kg body weight per dose, such as from about 2.2 milligram per kg body weight per dose to about 10 milligram per kg body weight per dose, for example from about 2.4 milligram per kg body weight per dose to about 10 milligram per kg body weight per dose, such as from about 2.6 milligram per kg body weight per dose to about 10 milligram per kg body weight per dose, for example from about 2.8 milligram per kg body weight per dose to about 10 milligram per kg body weight per dose, such as from about 3.0 milligram per kg body weight per dose to about 10 milligram per kg body weight per dose, for example from about 3.2 milligram per kg body weight per dose to about 10 milligram per kg body weight per dose, such as from about 3.4 milligram per kg body weight per dose to about 10 milligram per kg body weight per dose, for example from about 3.6 milligram per kg body weight per dose to about 10 milligram per kg body weight per dose, such as from about 3.8 milligram per kg body weight per dose to about 10 milligram per kg body weight per dose, for example from about 4.0 milligram per kg body weight per dose to about 10 milligram per kg body weight per dose, such as from about 4.2 milligram per kg body weight per dose to about 10 milligram per kg body weight per dose, for example from about 4.4 milligram per kg body weight per dose to about 10 milligram per kg body weight per dose, such as from about 4.6 milligram per kg body weight per dose to about 10 milligram per kg body weight per dose, for example from about 4.8 milligram per kg body weight per dose to about 10 milligram per kg body weight per dose, such as from about 5.0 milligram per kg body weight per dose to about 10 milligram per kg body weight per dose, for example from about 5.2 milligram per kg body weight per dose to about 10 milligram per kg body weight per dose, such as from about 5.4 milligram per kg body weight per dose to about 10 milligram per kg body weight per dose, for example from about 5.6 milligram per kg body weight per dose to about 10 milligram per kg body weight per dose, such as from about 5.8 milligram per kg body weight per dose to about 10 milligram per kg body weight per dose, for example from about 6.0 milligram per kg body weight per dose to about 10 milligram per kg body weight per dose, such as from about 6.2 milligram per kg body weight per dose to about 10 milligram per kg body weight per dose, for example from about 6.4 milligram per kg body weight per dose to about 10 milligram per kg body weight per dose, such as from about 6.6 milligram per kg body weight per dose to about 10 milligram per kg body weight per dose, for example from about 6.8 milligram per kg body weight per dose to about 10 milligram per kg body weight per dose, such as from about 7.0 milligram per kg body weight per dose to about 10 milligram per kg body weight per dose, for example from about 7.2 milligram per kg body weight per dose to about 10 milligram per kg body weight per dose, such as from about 7.4 milligram per kg body weight per dose to about 10 milligram per kg body weight per dose, for example from about 7.6 milligram per kg body weight per dose to about 10 milligram per kg body weight per dose, such as from about 7.8 milligram per kg body weight per dose to about 10 milligram per kg body weight per dose, for example from about 8.0 milligram per kg body weight per dose to about 10 milligram per kg body weight per dose, such as from about 0.2 milligram per kg body weight per dose to about 8 milligram per kg body weight per dose, for example from about 0.3 milligram per kg body weight per dose to about 8 milligram per kg body weight per dose, such as from about 0.4 milligram per kg body weight per dose to about 8 milligram per kg body weight per dose, for example from about 0.5 milligram per kg body weight per dose to about 8 milligram per kg body weight per dose, such as from about 0.6 milligram per kg body weight per dose to about 8 milligram per kg body weight per dose, for example from about 0.7 milligram per kg body weight per dose to about 8 milligram per kg body weight per dose, such as from about 0.8 milligram per kg body weight per dose to about 8 milligram per kg body weight per dose, for example from about 0.9 milligram per kg body weight per dose to about 8 milligram per kg body weight per dose, such as from about 1.0 milligram per kg body weight per dose to about 8 milligram per kg body weight per dose, for example from about 1.2 milligram per kg body weight per dose to about 8 milligram per kg body weight per dose, such as from about 1.4 milligram per kg body weight per dose to about 8 milligram per kg body weight per dose, for example from about 1.6 milligram per kg body weight per dose to about 8 milligram per kg body weight per dose, such as from about 1.8 milligram per kg body weight per dose to about 8 milligram per kg body weight per dose, for example from about 2.0 milligram per kg body weight per dose to about 8 milligram per kg body weight per dose, such as from about 2.2 milligram per kg body weight per dose to about 8 milligram per kg body weight per dose, for example from about 2.4 milligram per kg body weight per dose to about 8 milligram per kg body weight per dose, such as from about 2.6 milligram per kg body weight per dose to about 8 milligram per kg body weight per dose, for example from about 2.8 milligram per kg body weight per dose to about 8 milligram per kg body weight per dose, such as from about 3.0 milligram per kg body weight per dose to about 8 milligram per kg body weight per dose, for example from about 3.2 milligram per kg body weight per dose to about 8 milligram per kg body weight per dose, such as from about 3.4 milligram per kg body weight per dose to about 8 milligram per kg body weight per dose, for example from about 3.6 milligram per kg body weight per dose to about 8 milligram per kg body weight per dose, such as from about 3.8 milligram per kg body weight per dose to about 8 milligram per kg body weight per dose, for example from about 4.0 milligram per kg body weight per dose to about 8 milligram per kg body weight per dose, such as from about 4.2 milligram per kg body weight per dose to about 8 milligram per kg body weight per dose, for example from about 4.4 milligram per kg body weight per dose to about 8 milligram per kg body weight per dose, such as from about 4.6 milligram per kg body weight per dose to about 8 milligram per kg body weight per dose, for example from about 4.8 milligram per kg body weight per dose to about 8 milligram per kg body weight per dose, such as from about 5.0 milligram per kg body weight per dose to about 8 milligram per kg body weight per dose, for example from about 5.2 milligram per kg body weight per dose to about 8 milligram per kg body weight per dose, such as from about 5.4 milligram per kg body weight per dose to about 8 milligram per kg body weight per dose, for example from about 5.6 milligram per kg body weight per dose to about 8 milligram per kg body weight per dose, such as from about 5.8 milligram per kg body weight per dose to about 8 milligram per kg body weight per dose, for example from about 6.0 milligram per kg body weight per dose to about 8 milligram per kg body weight per dose, such as from about 0.2 milligram per kg body weight per dose to about 6 milligram per kg body weight per dose, for example from about 0.3 milligram per kg body weight per dose to about 6 milligram per kg body weight per dose, such as from about 0.4 milligram per kg body weight per dose to about 6 milligram per kg body weight per dose, for example from about 0.5 milligram per kg body weight per dose to about 6 milligram per kg body weight per dose, such as from about 0.6 milligram per kg body weight per dose to about 6 milligram per kg body weight per dose, for example from about 0.7 milligram per kg body weight per dose to about 6 milligram per kg body weight per dose, such as from about 0.8 milligram per kg body weight per dose to about 6 milligram per kg body weight per dose, for example from about 0.9 milligram per kg body weight per dose to about 6 milligram per kg body weight per dose, such as from about 1.0 milligram per kg body weight per dose to about 6 milligram per kg body weight per dose, for example from about 1.2 milligram per kg body weight per dose to about 6 milligram per kg body weight per dose, such as from about 1.4 milligram per kg body weight per dose to about 6 milligram per kg body weight per dose, for example from about 1.6 milligram per kg body weight per dose to about 6 milligram per kg body weight per dose, such as from about 1.8 milligram per kg body weight per dose to about 6 milligram per kg body weight per dose, for example from about 2.0 milligram per kg body weight per dose to about 6 milligram per kg body weight per dose, such as from about 2.2 milligram per kg body weight per dose to about 6 milligram per kg body weight per dose, for example from about 2.4 milligram per kg body weight per dose to about 6 milligram per kg body weight per dose, such as from about 2.6 milligram per kg body weight per dose to about 6 milligram per kg body weight per dose, for example from about 2.8 milligram per kg body weight per dose to about 6 milligram per kg body weight per dose, such as from about 3.0 milligram per kg body weight per dose to about 6 milligram per kg body weight per dose, for example from about 3.2 milligram per kg body weight per dose to about 6 milligram per kg body weight per dose, such as from about 3.4 milligram per kg body weight per dose to about 6 milligram per kg body weight per dose, for example from about 3.6 milligram per kg body weight per dose to about 6 milligram per kg body weight per dose, such as from about 3.8 milligram per kg body weight per dose to about 6 milligram per kg body weight per dose, for example from about 4.0 milligram per kg body weight per dose to about 6 milligram per kg body weight per dose, such as from about 4.2 milligram per kg body weight per dose to about 6 milligram per kg body weight per dose, for example from about 4.4 milligram per kg body weight per dose to about 6 milligram per kg body weight per dose, such as from about 4.6 milligram per kg body weight per dose to about 6 milligram per kg body weight per dose, for example from about 4.8 milligram per kg body weight per dose to about 6 milligram per kg body weight per dose, such as from about 5.0 milligram per kg body weight per dose to about 6 milligram per kg body weight per dose.

Co-Administration with One or More Drugs

The composition according to the present invention can be co-administered to an individual in need thereof in combination with one or more drugs such as one or more drugs with antimicrobial effect.

The composition according to the present invention can be co-administered to an individual in need thereof in combination with one or more antibiotics. The one or more antibiotics can be selected from the group consisting of Amikacin disulfate salt, Amikacin hydrate, Anisomycin from *Streptomyces*

*griseolus*, Apramycin sulfate salt, Azithromycin, Blasticidine S hydrochloride, Brefeldin A, Brefeldin A from *Penicillium brefeldianum*, Butirosin sulfate salt, Butirosin A from *Bacillus vitellinus*, Chloramphenicol, Chloramphenicol base, Chloramphenicol succinate sodium salt, Chlortetracycline hydrochloride, Chlortetracycline hydrochloride from *Streptomyces aureofaciens*, Clindamycin 2-phosphate, Clindamycin hydrochloride, Clotrimazole, Cycloheximide from microbial, Demeclocycline hydrochloride, Dibekacin sulfate salt, Dihydrostreptomycin sesquisulfate, Dihydrostreptomycin solution, Doxycycline hyclate, Duramycin from *Streptoverticillium cinnamoneus*, Emetine dihydrochloride hydrate), Erythromycin, Erythromycin USP, Erythromycin powder, Erythromycin, Temephos, Erythromycin estolate, Erythromycin ethyl succinate, Erythromycin standard solution, Erythromycin stearate, Fusidic acid sodium salt, G 418 disulfate salt, G 418 disulfate salt powder, G 418 disulfate salt solution liquid, Gentamicin solution liquid, Gentamicin solution, Gentamicin sulfate *Micromonospora purpurea*, Gentamicin sulfate salt, Gentamicin sulfate salt powder USP, Gentamicin-Glutamine solution liquid, Helvolic acid from *Cephalosporium caerulens*, Hygromycin B *Streptomyces hygroscopicus*, Hygromycin B *Streptomyces hygroscopicus* powder, Hygromycin B solution *Streptomyces hygroscopicus*, Josamycin, Josamycin solution, Kanamycin B sulfate salt, Kanamycin disulfate salt from *Streptomyces kanamyceticus*, Kanamycin monosulfate from *Streptomyces kanamyceticus*, Kanamycin monosulfate from *Streptomyces kanamyceticus* powder USP, Kanamycin solution from *Streptomyces kanamyceticus*, Kirromycin from *Streptomyces collinus*, Lincomycin hydrochloride, Lincomycin standard solution, Meclocycline sulfosalicylate salt, Mepartricin, Midecamycin from *Streptomyces mycarofaciens*, Minocycline hydrochloride crystalline, Neomycin solution, Neomycin trisulfate salt hydrate, Neomycin trisulfate salt hydrate powder, Neomycin trisulfate salt hydrate USP powder, Netilmicin sulfate salt, Nitrofurantoin crystalline, Nourseothricin sulfate, Oleandomycin phosphate salt, Oleandomycin triacetate, Oxytetracycline dihydrate, Oxytetracycline hemicalcium salt, Oxytetracycline hydrochloride, Paromomycin sulfate salt, Puromycin dihydrochloride from *Streptomyces alboniger*, Rapamycin from *Streptomyces hygroscopicus*, Ribostamycin sulfate salt, Rifampicin, Rifamycin SV sodium salt, Rosamicin *Micromonospora rosaria*, Sisomicin sulfate salt, Spectinomycin dihydrochloride hydrate, Spectinomycin dihydrochloride hydrate powder, Spectinomycin dihydrochloride pentahydrate, Spiramycin, Spiramycin from *Streptomyces* sp., Spiramycin solution, Streptomycin solution, Streptomycin sulfate salt, Streptomycin sulfate salt powder, Tetracycline, Tetracycline hydrochloride, Tetracycline hydrochloride USP, Tetracycline hydrochloride powder, Thiamphenicol, Thiostrepton from *Streptomyces azureus*, Tobramycin, Tobramycin sulfate salt, Tunicamycin $A_1$ homolog, Tunicamycin $C_2$ homolog, Tunicamycin *Streptomyces* sp., Tylosin solution, Tylosin tartrate, Viomycin sulfate salt, Virginiamycin $M_1$, (S)-(+)-Camptothecin, 10-Deacetylbaccatin III from *Taxus baccata*, 5-Azacytidine, 7-Aminoactinomycin D, 8-Quinolinol crystalline, 8-Quinolinol hemisulfate salt crystalline, 9-Dihydro-13-acetylbaccatin III from *Taxus canadensis*, Aclarubicin, Aclarubicin hydrochloride, Actinomycin D from *Streptomyces* sp., Actinomycin I from *Streptomyces antibioticus*, Actinomycin V from *Streptomyces antibioticus*, Aphidicolin *Nigrospora sphaerica*, Bafilomycin A1 from *Streptomyces griseus*, Bleomycin sulfate from *Streptomyces verticillus*, Capreomycin sulfate from *Streptomyces capreolus*, Chromomycin $A_3$ *Streptomyces griseus*, Cinoxacin, Ciprofloxacin BioChemika, cis-Diammineplatinum(II) dichloride, Coumermycin A1, Cytochalasin B *Helminthosporium dematioideum*, Cytochalasin D *Zygosporium mansonii*, Dacarbazine, Daunorubicin hydrochloride, Daunorubicin hydrochloride USP, Distamycin A hydrochloride from *Streptomyces distallicus*, Doxorubicin hydrochloride, Echinomycin, Echinomycin BioChemika, Enrofloxacin BioChemika, Etoposide, Etoposide solid, Flumequine, Formycin, Fumagillin from *Aspergillus fumigatus*, Ganciclovir, Gliotoxin from *Gliocladium fimbriatum*, Lomefloxacin hydrochloride, Metronidazole purum, Mithramycin A from *Streptomyces plicatus*, Mitomycin C *Streptomyces caespitosus*, Nalidixic acid, Nalidixic acid sodium salt, Nalidixic acid sodium salt powder, Netropsin dihydrochloride hydrate, Nitrofurantoin, Nogalamycin from *Streptomyces nogalater*, Nonactin from *Streptomyces tsusimaensis*, Novobiocin sodium salt, Ofloxacin, Oxolinic acid, Paclitaxel from *Taxus yannanensis*, Paclitaxel from *Taxus brevifolia*, Phenazine methosulfate, Phleomycin *Streptomyces verticillus*, Pipemidic acid, Rebeccamycin from *Saccharothrix aerocolonigenes*, Sinefungin, Streptonigrin from *Streptomyces flocculus*, Streptozocin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Trimethoprim, Trimethoprim lactate salt, Tubercidin from *Streptomyces tubercidicus*, 5-Azacytidine, Cordycepin, Formycin A, (+)-6-Aminopenicillanic acid, 7-Aminodesacetoxycephalosporanic acid, Amoxicillin, Ampicillin, Ampicillin sodium salt, Ampicillin trihydrate, Ampicillin trihydrate USP, Azlocillin sodium salt, Bacitracin *Bacillus licheniformis*, Bacitracin zinc salt Bacillus licheniformis, Carbenicillin disodium salt, Cefaclor, Cefamandole lithium salt, Cefamandole nafate, Cefamandole sodium salt, Cefazolin sodium salt, Cefinetazole sodium salt, Cefoperazone sodium salt, Cefotaxime sodium salt, Cefsulodin sodium salt, Cefsulodin sodium salt hydrate, Ceftriaxone sodium salt, Cephalexin hydrate, Cephalosporin C zinc salt, Cephalothin sodium salt, Cephapirin sodium salt, Cephradine, Cloxacillin sodium salt, Cloxacillin sodium salt monohydrate, D-( )-Penicillamine hydrochloride, D-Cycloserine microbial, D-Cycloserine powder, Dicloxacillin sodium salt monohydrate, D-Penicillamine, Econazole nitrate salt, Ethambutol dihydrochloride, Lysostaphin from Staphylococcus staphylolyticus, Moxalactam sodium salt, Nafcillin sodium salt monohydrate, Nikkomycin, Nikkomycin Z *Streptomyces tendae*, Nitrofurantoin crystalline, Oxacillin sodium salt, Penicillic acid powder, Penicillin G potassium salt, Penicillin G potassium salt powder, Penicillin G potassium salt, Penicillin G sodium salt hydrate powder, Penicillin G sodium salt powder, Penicillin G sodium salt, Phenethicillin potassium salt, Phenoxymethylpenicillinic acid potassium salt, Phosphomycin disodium salt, Pipemidic acid, Piperacillin sodium salt, Ristomycin monosulfate, Vancomycin hydrochloride from *Streptomyces orientalis*, 2-Mercaptopyridine N-oxide sodium salt, 4-Bromocalcimycin A23187 BioChemika, Alamethicin *Trichoderma viride*, Amphotericin B *Streptomyces* sp., Amphotericin B preparation, Calcimycin A23187, Calcimycin A23187 hemi(calcium-magnesium) salt, Calcimycin A23187 hemicalcium salt, Calcimycin A23187 hemimagnesium salt, Chlorhexidine diacetate salt monohydrate, Chlorhexidine diacetate salt hydrate, Chlorhexidine digluconate, Clotrimazole, Colistin sodium methanesulfonate, Colistin sodium methanesulfonate from *Bacillus colistinus*, Colistin sulfate salt, Econazole nitrate salt, Hydrocortisone 21-acetate, Filipin complex *Streptomyces filipinensis*, Gliotoxin from *Gliocladium fimbriatum*, Gramicidin A from *Bacillus brevis*, Gramicidin C from *Bacillus brevis*, Gramicidin from *Bacillus* aneurinolyticus (Bacillus brevis), Ionomycin calcium salt Streptomyces conglobatus, Lasalocid A sodium salt, Lonomycin A sodium salt from Streptomyces ribosidificus, Monensin sodium salt, N-(6-Aminohexyl)-5-chloro-1-naphthalenesulfonamide hydrochloride, Narasin from Streptomyces auriofaciens, Nigericin sodium salt from Streptomyces hygroscopicus, Nisin from Streptococcus lactis, Nonactin from Streptomyces sp., Nystatin, Nystatin powder, Phenazine methosulfate, Pimaricin, Pimaricin from Streptomyces chattanoogensis, Polymyxin B solution, Polymyxin B sulfate salt, DL-Penicillamine acetone adduct hydrochloride monohydrate, Polymyxin B sulfate salt powder USP, Praziquantel, Salinomycin from Streptomyces albus, Salinomycin from Streptomyces albus, Surfactin from Bacillus subtilis, Valinomycin, (+)-Usnic acid from Usnea dasypoga, (±)-Miconazole nitrate salt, (S)-(+)-Camptothecin, 1-Deoxymannojirimycin hydrochloride, 1-Deoxynojirimycin hydrochloride, 2-Heptyl-4-hydroxyquinoline N-oxide, Cordycepin, 1,10-Phenanthroline hydrochloride monohydrate puriss., 6-Diazo-5-oxo-L-norleucine, 8-Quinolinol crystalline, 8-Quinolinol hemisulfate salt, Antimycin A from Streptomyces sp., Antimycin $A_1$, Antimycin $A_2$, Antimycin $A_3$, Antipain, Ascomycin, Azaserine, Bafilomycin A1 from Streptomyces griseus, Bafilomycin B1 from Streptomyces species, Cerulenin BioChemika, Chloroquine diphosphate salt, Cinoxacin, Ciprofloxacin, Mevastatin BioChemika, Concanamycin A, Concanamycin A Streptomyces sp, Concanamycin C from Streptomyces species, Coumermycin A1, Cyclosporin A from Tolypocladium inflatum, Cyclosporin A, Econazole nitrate salt, Enrofloxacin, Etoposide, Flumequine, Formycin A, Furazolidone, Fusaric acid from Gibberella fujikuroi, Geldanamycin from Streptomyces hygroscopicus, Gliotoxin from Gliocladium fimbriatum, Gramicidin A from Bacillus brevis, Gramicidin C from Bacillus brevis, Gramicidin from Bacillus aneurinolyticus (Bacillus brevis), Gramicidin from Bacillus brevis, Herbimycin A from Streptomyces hygroscopicus, Indomethacin, Irgasan, Lomefloxacin hydrochloride, Mycophenolic acid powder, Myxothiazol BioChemika, N-(6-Aminohexyl)-5-chloro-1-naphthalenesulfonamide hydrochloride, Nalidixic acid, Netropsin dihydrochloride hydrate, Niclosamide, Nikkomycin BioChemika, Nikkomycin Z Streptomyces tendae, N-Methyl-1-deoxynojirimycin, Nogalamycin from Streptomyces nogalater, Nonactin ☐80% from Streptomyces tsusimaensis, Nonactin from Streptomyces sp., Novobiocin sodium salt, Ofloxacin, Oleandomycin triacetate, Oligomycin Streptomyces diastatochromogenes, Oligomycin A, Oligomycin B, Oligomycin C, Oligomycin Streptomyces diastatochromogenes, Oxolinic acid, Piericidin A from Streptomyces mobaraensis, Pipemidic acid, Radicicol from Diheterospora chlamydosporia solid, Rapamycin from Streptomyces hygroscopicus, Rebeccamycin from Saccharothrix aerocolonigenes, Sinefungin, Staurosporine Streptomyces sp., Stigmatellin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Triacsin C from Streptomyces sp., Trimethoprim, Trimethoprim lactate salt, Vineomycin $A_1$ from Streptomyces albogriseolus subsp., Tectorigenin, and Paracelsin Trichoderma reesei.

The composition according to the present invention can be co-administered to an individual in need thereof in combination with one or more antiviral drugs. The one or more antiviral drugs can be selected from the group consisting of Abacavir, Aciclovir, Acyclovir, Adefovir, Alferon LDO, Amantadine, Amdoxovir, Ampligen, Amprenavir, Aplaviroc, Apricitabine, Arbidol, Atazanavir, Ateviridine, Atripla, Bevirimat, BILN 2061, Brecanavir, Brivudine, Calanolide A, Capravirine, Cidofovir, Combivir, Condylox, Cyanovirin-N, Darunavir, Delavirdine, Dexelvucitabine, Diarylpyrimidines, Didanosine, Docosanol, Edoxudine, Efavirenz, Elvitegravir, Elvucitabine, Emivirine, Emtricitabine, Enfuvirtide, Entecavir, Epigallocatechin gallate, Etravirine, Famciclovir, Fialuridine, Fomivirsen, Fosamprenavir, Foscarnet, Fosfonet, Fusion inhibitor, Ganciclovir, Gardasil, Globoidnan A, Griffithsin, GS-9137, Ibacitabine, Ibalizumab, Immunovir, Idoxuridine, Imiquimod, Indinavir, Inosine, Interferon-gamma, Interferon type III, Interferon type II, Interferon type I, Interferon, Lamivudine, Lodenosine, Lopinavir, Loviride, MK-0518, Maraviroc, Miltefosine, Moroxydine, Nelfinavir, Nevirapine, Nexavir, Oragen, Oseltamivir, Penciclovir, Peramivir, Pleconaril, Podophyllotoxin, Portmanteau inhibitors, PRO 140, Quinotaline, Racivir, Raltegravir, Ribavirin, Rilpivirine, Rimantadine, Ritonavir, R-roscovitine, Saquinavir, SCH 503034, Stampidine, Stavudine, Taribavirin, Telbivudine, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Vivecon, VX 950/Telaprevir, Zalcitabine, Zanamivir, and Zidovudine (AZT).

The composition according to the present invention can be co-administered to an individual in need thereof in combination with one or more antifungal drugs. The one or more antifungal drugs can be selected from the group consisting of polyene antimycotics such as Natamycin, Rimocidin, Filipin, Nystatin, Amphotericin B, and Candicin, imidazole and triazole antifungal drugs such as Imidazoles like Miconazole (Miconazole nitrate), Ketoconazole, Clotrimazole (marketed as Lotrimin, Canesten in the UK), Econazole, Bifonazole, Butoconazole, Fenticonazole, Isoconazole, Oxiconazole, Sertaconazole (marketed as Ertaczo), Sulconazole, Tioconazole, Fluconazole, Itraconazole, Isavuconazole, Ravuconazole, Posaconazole, Voriconazole, and Terconazole, Allylamines such as Terbinafine (marketed as Lamisil), Amorolfine, Naftifine (marketed as Naftin), and Butenafine (marketed as Lotrimin Ultra), Echinocandins such as Anidulafungin, Caspofungin, and Micafungin, Benzoic acid in combination with a keratolytic agent (such as in Whitfield's Ointment), Ciclopirox olamine, Flucytosine, or 5-fluorocytosine, Griseofulvin, and Gentian Violet Haloprogin Tolnaftate (marketed as Tinactin, Desenex, Aftate).

The composition according to the present invention can be co-administered to an individual in need thereof in combination with one or more antiparasitic drugs. The one or more antiparasitic drugs can be selected from the group consisting of Antinematodes such as Mebendazole (for most nematode infections), Pyrantel pamoate (for most nematode infections), Thiabendazole (for roundworm infections), and Diethycarbazine (for treatment of Lymphatic filariasis), The method according to item 197, wherein the one or more antiparasitic drugs comprises Anticestodes such as Niclosamide (for tapeworm infections), and Praziquantel (for tapeworm infections), Antitrematodes such as Praziquantel, Antiamoebics such as Rifampin, Amphotericin B, Clioquinol, Iodoquinol Metronidazole, Tinidazole, Ornidazole, Secnidazole Atovaquone, Emetine, Fumagillin, and Trimetrexate, Antiprotozoals such as Amphotericin, Antimony, Eflornithine, Furazolidone, Melarsoprol, Metronidazole, Miltefosine (Impavido), Ornidazole, Paromomycin sulfate, Pentamidine, Pyrimethamine, and Tinidazole.

Kit of Parts

In a further embodiment the present invention relates to a kit of parts comprising the antimicrobial composition according to the present invention. The kit of parts comprises at least one additional component, such as instructions for use, and/or one or more drugs for co-administration.

DETAILED DESCRIPTION OF THE DRAWINGS

FIG. 1 shows the phylogeny of the Crustacea. The closest relatives to Copepoda are the Cephalocarida and the Ostracoda. It is clear from the phylogenetic tree of the Crustacea subphylum that copepods and decapods are not closely related. Decapods include many familiar groups, such as crayfish, crabs, lobsters, prawns and shrimp.

Figure 2:
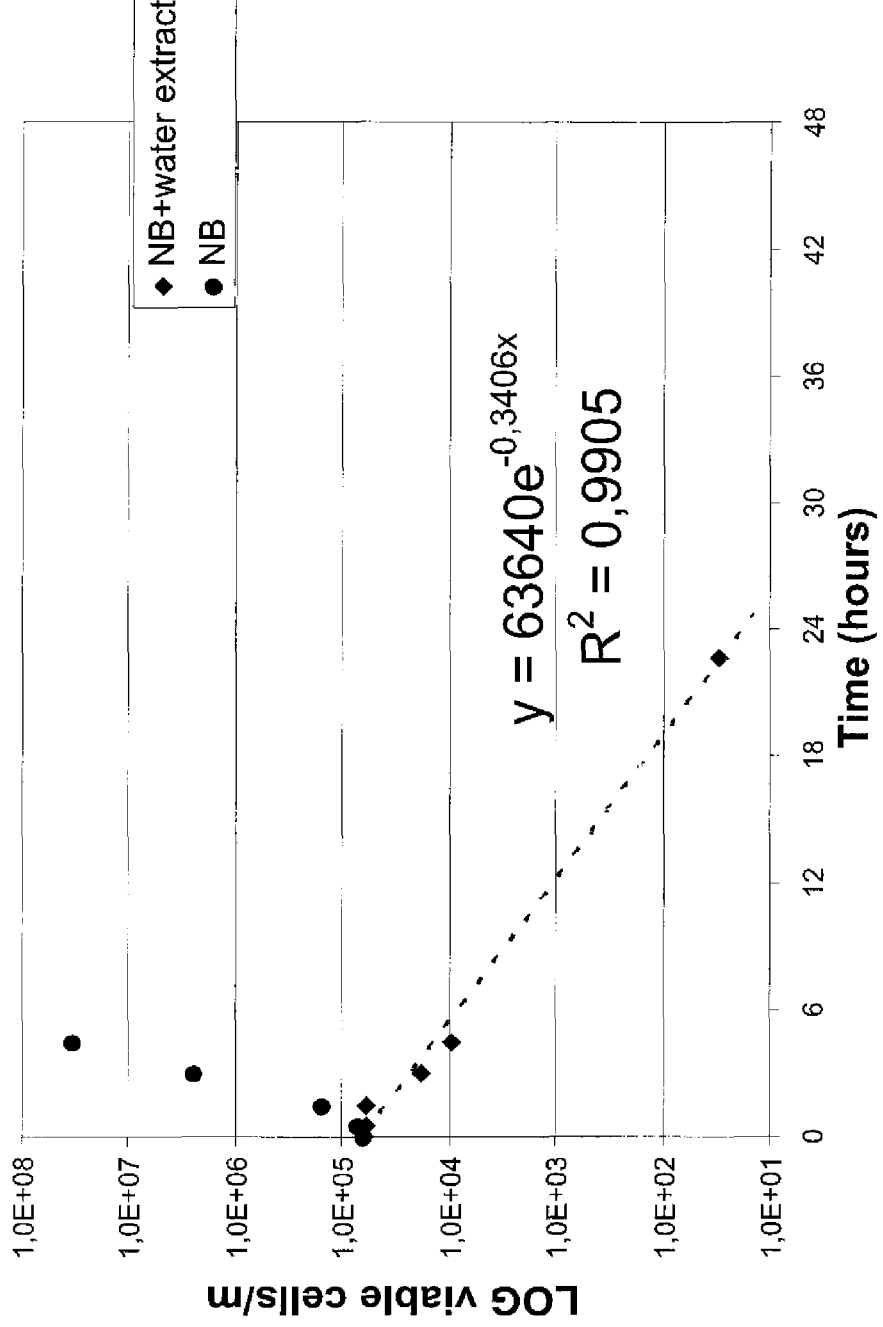
FIG. 2. shows the Development of the number of viable *Salmonella berta* cells.

FIG. 2 shows the Development of the number of viable *Salmonella berta* cells in Nutrient Broth and Nutrient Broth with added 10% aqueous phase from *Calanus finmarchicus* (catch 2) during incubation at 37° C.

Figure 3:
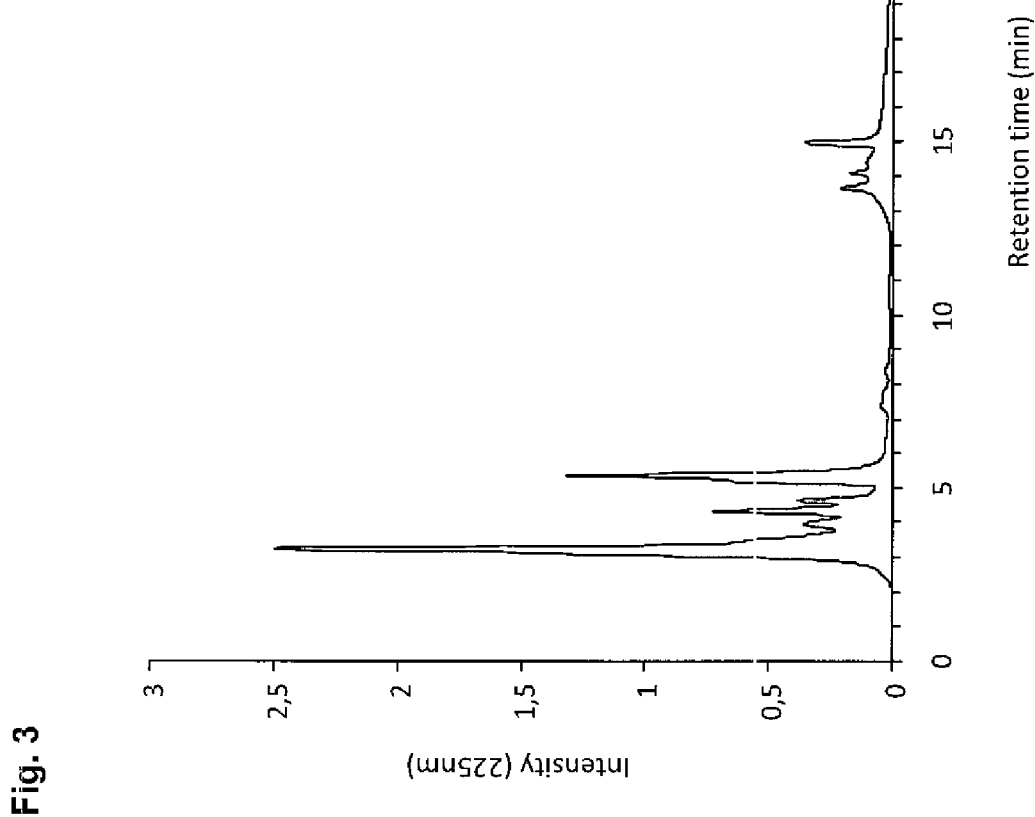
FIG. 3. HPLC-chromatogram of the anion exchange extract.

FIG. 3. HPLC-chromatogram of the anion exchange extract. The majority of the compounds including the active compound(s) elutes early during the run. This suggests that there are mostly polar or charged compounds in the extracts. Furthermore, C18-reversed phase chromatography is not the preferred method for separating the bioactive peak from contaminants.

Figure 4:
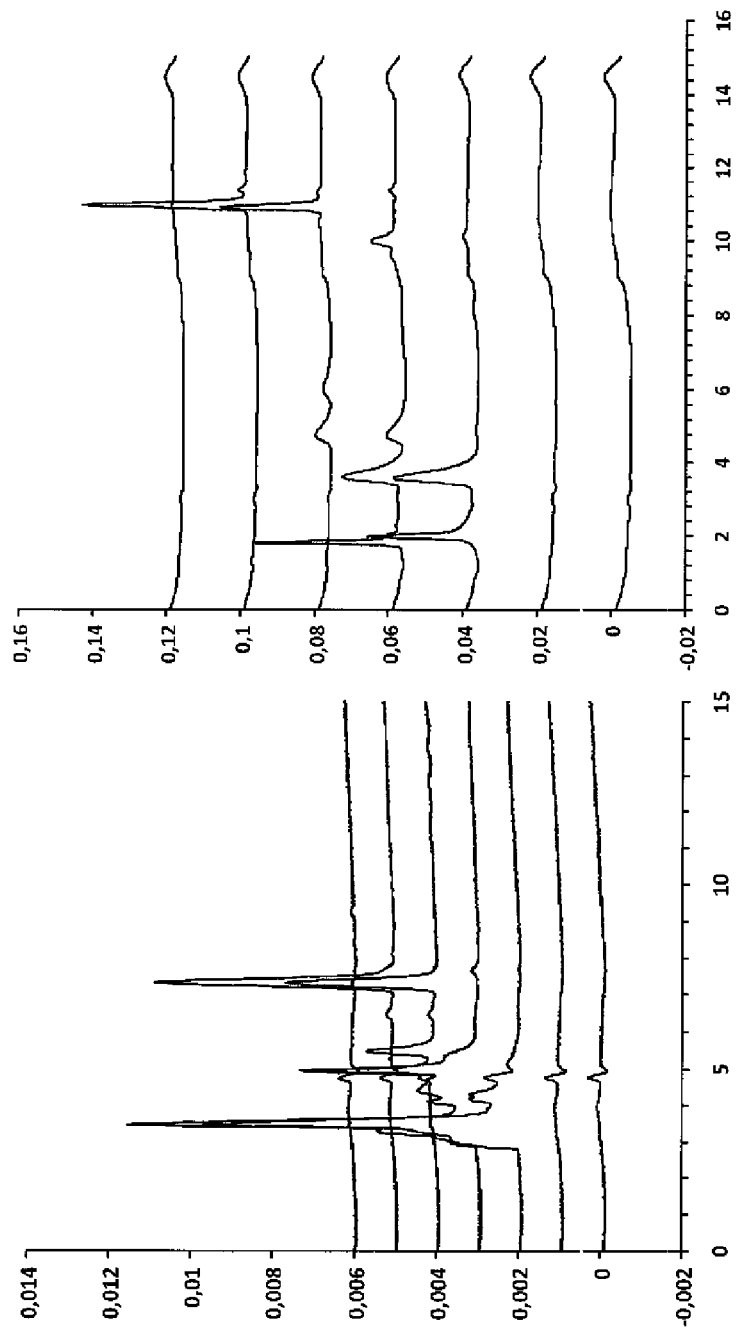
FIG. 4. Comparison of analytic chromatography of early fractions re-chromatographed on a conventional C18 (left), or polar endcapped C18 (right).

FIG. 4. Comparison of analytic chromatography of early fractions re-chromatographed on a conventional C18 (left), or polar endcapped C18 (right). Fraction 2 is the lower, and fraction 7 the upper chromatogram. The right panel show better separation of the peaks making it possible to distinguish the different peaks. The active fraction (fraction 4, the third chromatogram counting from below) is separated into four different peaks with the Aquasil column (right panel), whereas the conventional C18 column gives no base-line separation of the same fraction (left panel).

Figure 5:
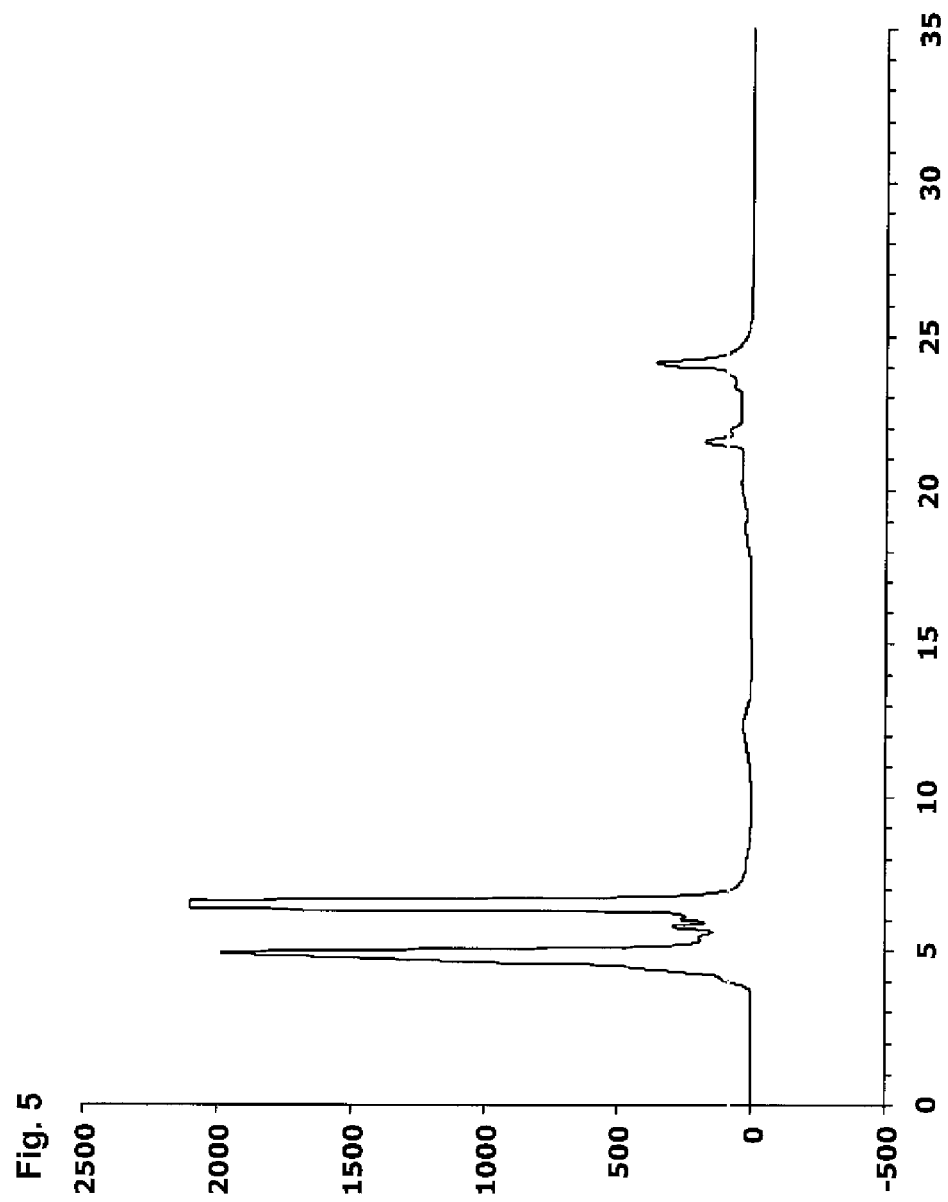
FIG. 5. Chromatogram of the semipreparativ C18-purification.

FIG. 5. Chromatogram of the semipreparativ C18-purification. Similar to the analytical run, the bioactivity eluted early during the run (see also Table 22).

Figure 6:
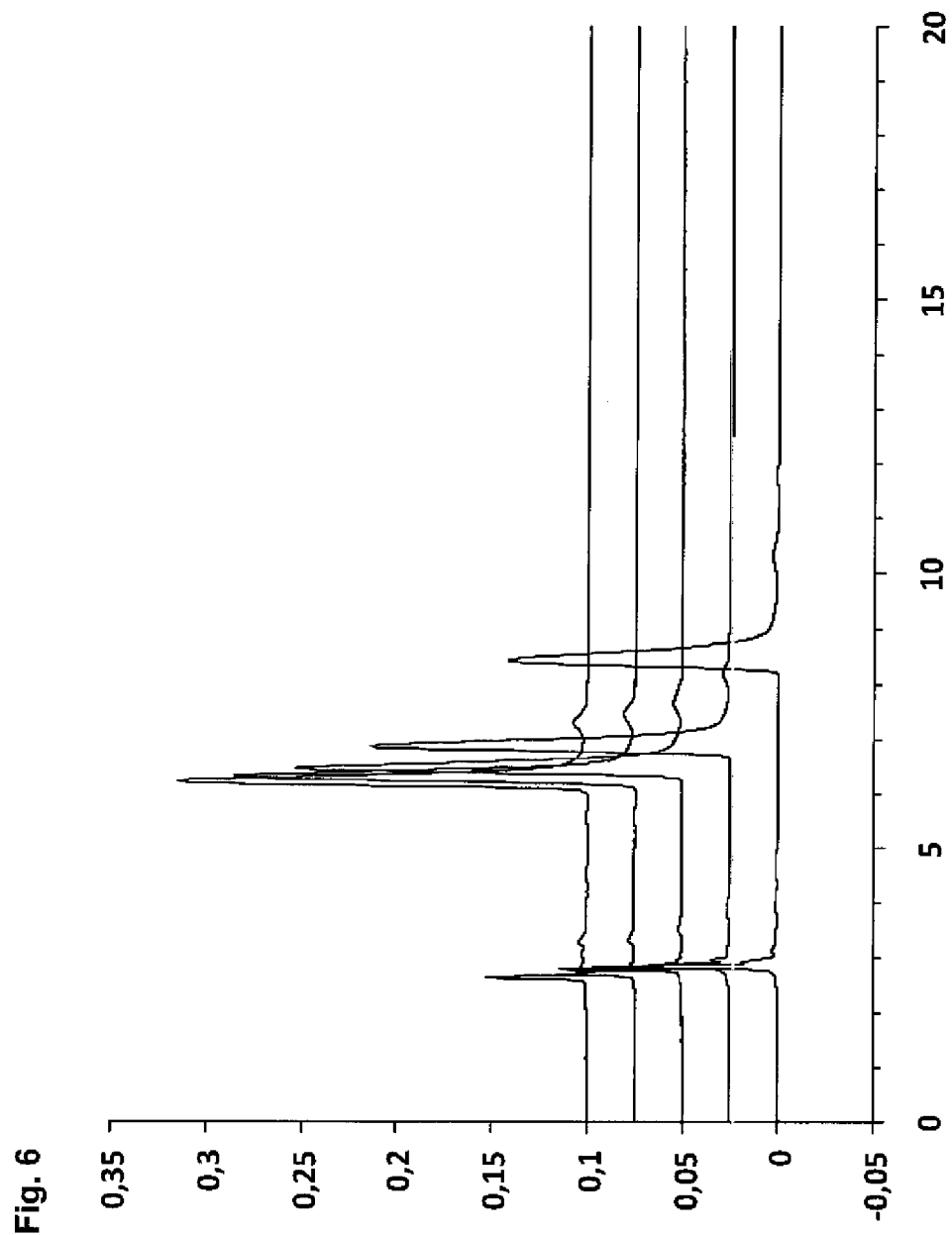
FIG. 6. Isocratic normal phase chromatography of the bioactive fraction from the semi-preparative reversed phase purification (FIG. 5).

FIG. 6. Isocratic normal phase chromatography of the bioactive fraction from the semi-preparative reversed phase purification (FIG. 5). The lower panel is 40/60 and the upper panel is 1/99 EtOAc/MeOH. The chromatogram shows that normal phase gives a good separation of at least 4 different peaks that occur as one peak during the reversed phase chromatography. Normal phase chromatography is probably the best method for separation of the active compound.

Figure 7:
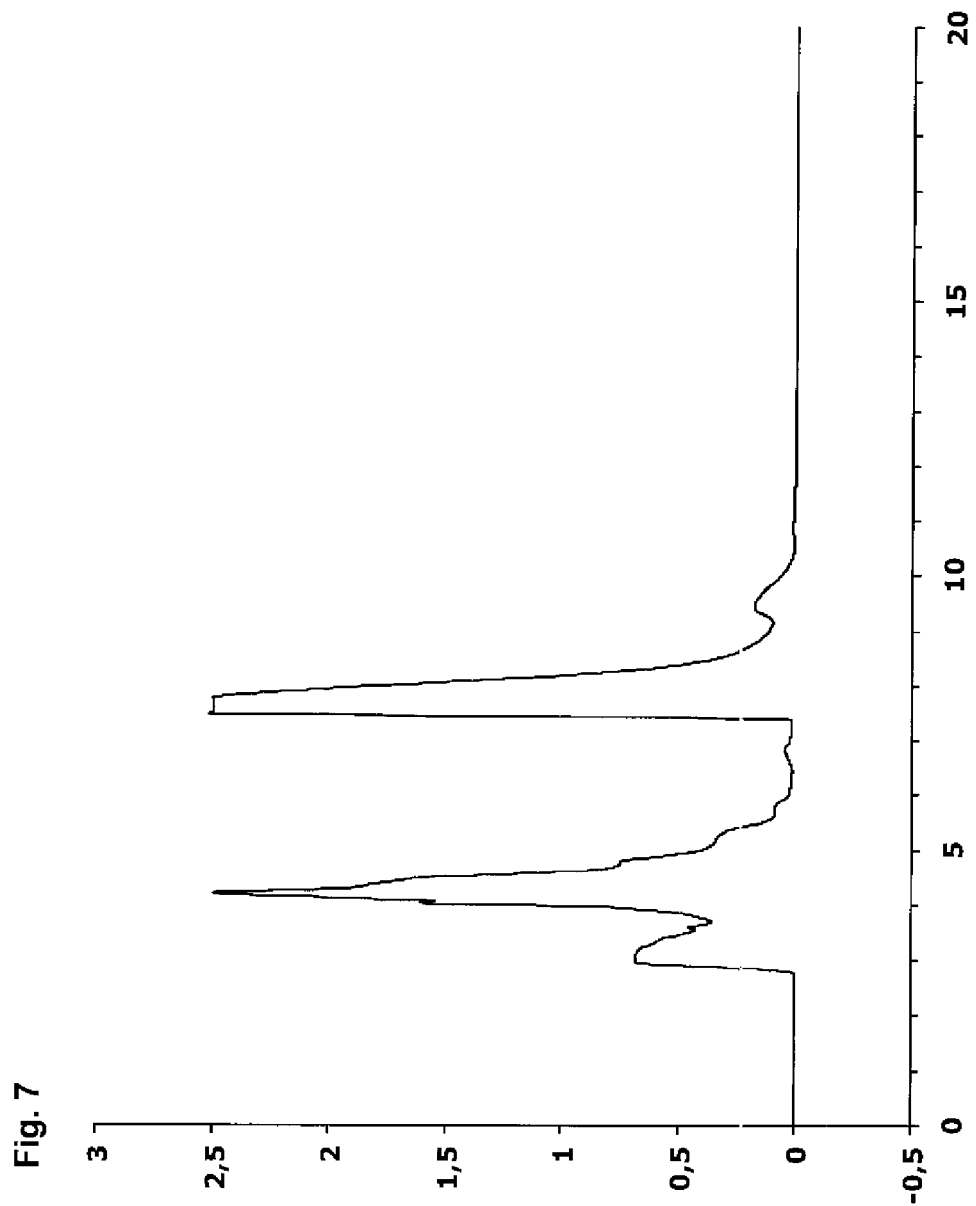
FIG. 7. Isocratic normal phase chromatography of the active peak from the semi-preparative reversed phase fractionation (FIG. 5).

FIG. 7. Isocratic normal phase chromatography of the active peak from the semi-preparative reversed phase fractionation (FIG. 5). See Table 22 for bioactivity of the fractions. The active fraction (4, approximately 3-4 min elution time) consists of several compounds, as seen by the shoulders of the peaks occurring at around 4 minutes. This could be due to the presence of several contaminants, but also several variants of the same compounds.

FIG. 8. UV-spectra of the various peaks from the normal phase chromatography shown in FIG. 7. The UV-spectra collected at different time-points in peak to varied little, suggesting that peak two consists of variants of the same compound.

FIG. 9. MS-analysis of fraction 4 from FIG. 8. When the masses from the background (blank injection) was subtracted, the 245 and 347 peaks stood out as the most interesting.

Figure 10:
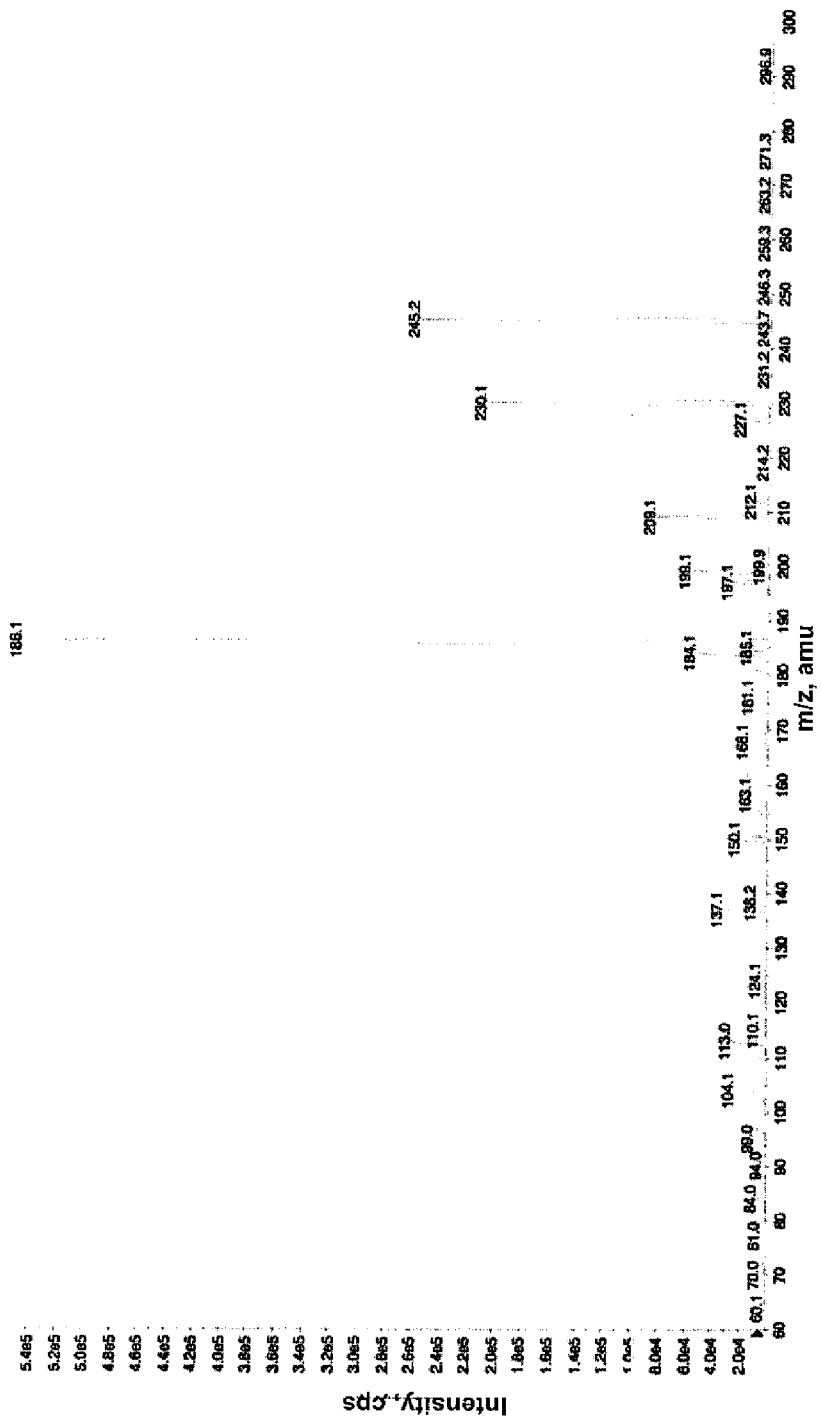
FIG. 10. MSMS-analysis of the 245-ion.

FIG. 10. MSMS-analysis of the 245-ion.

Figure 11:
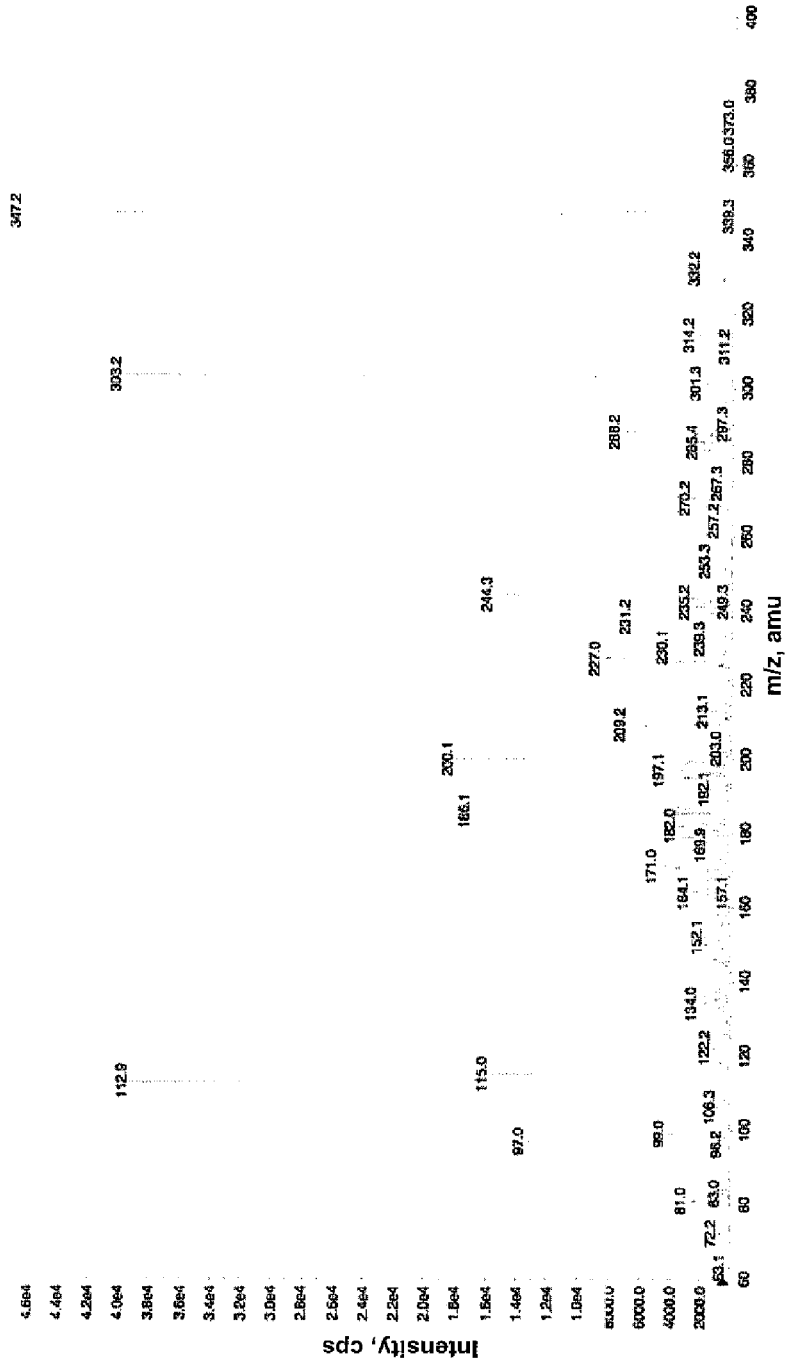
FIG. 11. MSMS-analysis of the 347-ion.

FIG. 11. MSMS-analysis of the 347-ion.

FIG. 12. The structure of penostatin with a mass=346 Da.

EXAMPLES

Example 1

Preparation of Extracts from *C. finmarchicus*

Catch and Storage of *Calanus finmarchicus*

Catch 1 was caught in the fjords of northern Norway. The catch was frozen on board the fishing vessel and stored frozen until examination. Composition (g/100 g): Water: 79.9, protein: 11.1, fat: 6.3, ash: 2.0.

Catch 2 was caught in Andfjord in northern Norway. The catch was frozen on board the fishing vessel within one hour after catch and stored frozen until examination. Composition (g/100 g): Water: 83.0, fat: 5.2.

Preparation of the Aqueous Phase 100 g frozen sample were thawed at ambient temperature and then centrifuged at 5.000×G for 10 minutes. The sample separated into three fractions where the sediment constituted approximately 60 g, the aqueous phase 38 g and the oil 2 g. The aqueous phase was filtered through a glass fiber filter (Schleicher & Schull, ref. no. 370003) and then through a micro porous cellulose acetate filter with pore size 0.2 μm (Whatman, FP 30/02CA-S). The sterile aqueous phase was stored in sterile capped glass tubes at 4-8° C.

The effect of crushing thawed *C. finmarchicus* in a mortar before centrifugation and filtration was examined (data not shown). The crushing did not affect the antimicrobial activity in the aqueous phase, but resulted in difficulties with the filtration and hence to reduced yields (volume) of filtrate. Therefore, thawed *C. finmarchicus* should not be crushed before centrifugation and filtration.

Different filter types were tested, e.g. purified cotton (IVBF Hartmann AG, CH 8212, Neuhausen, Switzerland), glass fiber filters (Schleicher & Schull, ref no. 370003), paper filters (Schleicher & Schull, Black Ribbon, ref no. 589) and microporous cellulose acetate filters with pore size 0.2 μm. The main purpose of filtering the aqueous phase after centrifugation was to remove particles and thus to give a clear liquid suitable for testing by the BTD method. The antimicrobial composition was not retained by any of the filter materials tested. The clearest liquid was obtained by the microporous filters, but the flow rate through this filter was significantly improved by pre-filtering through e.g. glass fiber filters.

Preparation of Methanol Extract

A concentrated composition with increased antimicrobial activity is prepared by methanol extraction.

Frozen *C. finmarchicus* were freeze dried before methanol-extraction and vacuum evaporation to remove the solvent. The concentrated extract was finally dissolved in deionised water and filtered through a micro-porous cellulose acetate filter with pore size 0.2 μm.

A comparison of the chemical composition and the antimicrobial activity of aqueous phase (catch 2) and methanol extract (catch 2) from *C. finmarchicus* is provided in table 5. The antimicrobial activity is much higher in the methanol extract compared to the aqueous phase.

TABLE 5

Comparison of the chemical composition and the antimicrobial activity of aqueous phase (catch 2) and methanol extract (catch 2) from *C. finmarchicus*

|  | Aqueous phase | Methanol extract |
|---|---|---|
| Protein (Raw protein Kjeldahl N*6.25) | 6.7% | 68.0% |
| Ash | 2.4% | 10.9% |
| Total fat Folch | 0.5% | 1.6% |
| Antimicrobial activity (MIC) | 16-32 | 128 |

Example 2

Determination of MIC (Minimal Inhibitory Concentration)

The activity and presence of antimicrobial substances in samples of aqueous phases or methanol extracts were tested by the BTD (Broth Tube Dilution) method, where 2-fold serial dilutions of sample in sterile water were added the same volume of double strength basis medium inoculated with the individual test organisms. After incubation as specified below, the test results were read. The lowest concentration (or highest dilution) preventing appearance of turbidity was considered to be the MIC (Minimal Inhibitory Concentration).

Preparation of Inoculated Double Strength Basis Media: Clostridia were Pre-Cultivated overnight in LTM (Liquid Thioglycollate Medium, Oxoid CM173) at 37° C. under anaerobic conditions. All other bacteria were pre-cultivated overnight in NB (Nutrient Broth, Oxoid CM0067) at 37° C. under aerobic conditions. All fungal species were pre-cultivated aerobically at 37° C. in NB supplemented with 1% glucose, until visible turbidity. Double strength basis media were finally inoculated with an amount of pre-culture sufficient to obtain an initial cell density of approximately 10E5/ml to 10E6/ml.

Test organisms: *Pseudomonas aeruginosa* (ATCC 27853), *Enterococcus faecalis* (ATCC 29212), *Listeria monocytogenes* (ATCC 7644), *Bacillus cereus* (CCUG 7414), *Staphylococcus aureus* (ATCC 25923), *Escherichia coli* (ATCC 25922), *Salmonella berta* (CCUG 27106), *Clostridium perfringens* (CCUG 1795), *Clostridium bifermentans* (CCUG T36626), MRSA (ATCC 43300), *Pseudomonas aeruginosa* (multiresistant clinical isolate), *Klebsiella pneumoniae* (multiresistant clinical isolate), *Acinetobacter* (multiresistant clinical isolate), *Candida albicans* (ATCC 10231), *Saccharomyces cerevisiae* (bakers yeast), *Aspergillus niger* (ATCC 16404).

Example 3

Detection of Antimicrobial Activity in Aqueous Phase

Antimicrobial activity has been detected in the aqueous phase from two different catches of *C. finmarchicus* (June/July 2003 and June 2006).

The activity and presence of antimicrobial compounds or substances in the aqueous phase extracted from catch 1 was tested by the BTD method using three different test bacteria. Growth of all the test bacteria was inhibited. The MIC values obtained from the results (table 6) for *E. coli, S. aureus* and *P. aeruginosa* were 8, 16 and 4, respectively.

TABLE 6

Development of turbidity in serial dilutions of aqueous phase from *C. finmarchicus* (catch 1) after inoculation with three different test organisms

| | Dilution | | | | | | |
|---|---|---|---|---|---|---|---|
| Test organism | × 2 | × 4 | × 8 | × 16 | × 32 | × 64 | Water |
| *E. coli* | − | − | − | + | + | + | + |
| *S. aureus* | − | − | − | − | + | + | + |
| *P. aeruginosa* | − | − | + | + | + | + | + |
| No inoculum | − | − | − | − | − | − | − |

+: turbidity,
−: no turbidity

Range of Action

The range of action of the antimicrobial substance in the aqueous phase extracted from catch 2 was tested by the BTD method using nine different test bacteria (*P. aeruginosa, E. faecalis, L. monocytogenes, B. cereus, S. aureus, E. coli, S. berta, C. perfringens, C. bifermentans* and one fungal species (*C. albicans*). All of the test bacteria, which represent Gram +, Gram −, aerobic and strict anaerobic types, were inhibited (table 7). The tested fungal species was not inhibited.

TABLE 7

Development of turbidity in serial dilutions of aqueous phase obtained from *C. finmarchicus* (catch 2) after inoculation with ten different test organisms

| | Dilution | | | | | | |
|---|---|---|---|---|---|---|---|
| Test organism | × 2 | × 4 | × 8 | × 16 | × 32 | × 64 | Water |
| *P. aeruginosa* | − | − | + | + | + | + | + |
| *E. faecalis* | − | − | − | + | + | + | + |
| *L. monocytog.* | − | − | − | − | + | + | + |
| *B. cereus* | − | − | − | − | − | + | + |
| *S. aureus* | − | − | − | − | − | + | + |
| *E. coli* | − | − | − | + | + | + | + |
| *S. berta* | − | − | − | − | − | + | + |
| *C. perfringens* | − | − | − | − | + | + | + |
| *C. bifermentans* | − | − | − | − | + | + | + |
| *C. albicans* (yeast) | + | + | + | + | + | + | + |
| No inoculum | − | − | − | − | − | − | − |

+: turbidity,
−: no turbidity

Example 4

Inactivation Kinetics

The course of killing was examined by inoculating *S. berta* in 100 ml NB and in 90 ml NB with added 10 ml of aqueous phase extracted from catch 2. The initial cells concentration was approximately 10 E5 per ml. The bottles were incubated at 37° C., and aliquots withdrawn during incubation for determination of viable aerobic microorganisms (Nordic Committee on Food Analysis no. 86). The bacteria grew well in pure NB while in the presence of ×10 diluted aqueous phase, the number of viable cells underwent reduction. From the formula of the exponential trend line (FIG. 2), decimal reduction time could be estimated to 6.8 hours. FIG. 2 shows the Development of the number of viable *Salmonella berta* cells in Nutrient Broth and Nutrient Broth with added 10% aqueous phase from *Calanus finmarchicus* (catch 2) during incubation at 37° C.

Example 5

Heat Stability

The heat stability of the antimicrobial substance in aqueous phase from catch 2 was tested by the BTD method using *S. aureus* as a test organism. Heat treatment at 70° C. for 10 minutes had no effect on the activity of the antimicrobial substance. Heat treatment at 100° C. for 10 minutes caused a slight reduction of activity and 121° C. for 15 minutes caused a substantial reduction (table 8).

TABLE 8

Development of turbidity in serial dilutions of heat treated aqueous phase from *C. finmarchicus* (catch 2), after inoculation with the test organisms *Staphylococcus aureus*.

| Heat treatment | Dilution | | | | | | |
|---|---|---|---|---|---|---|---|
| | × 2 | × 4 | × 8 | × 16 | × 32 | × 64 | Water |
| No heating | − | − | − | − | − | + | + |
| 10 minutes/70° C. | − | − | − | − | − | + | + |
| 10 minutes/100° C. | − | − | − | − | + | + | + |
| 15 minutes/121° C. | − | − | + | + | + | + | + |
| No inoculum | − | − | − | − | − | − | − |

Example 6

Resistance to Proteolytic Enzymes

The resistance of the antimicrobial composition to digestion by three proteolytic enzymes, pepsin, alcalase and proteinase K was tested by the BTD method using *S. aureus* as a test organism.

1 ml of the aqueous phase from catch 2 was added to 0.2 ml 1.0 N HCl and 0.1 ml 0.1 N HCl with 1% (w/v) pepsin (article no. 1.07190.0100, Merck). The reaction mixture (pH 2.36) was incubated at 37° C. for 18 hours with occasional stirring. As a control, 1 ml of the aqueous phase was incubated similarly after addition of the same amount of acid without pepsin. The results of the BTD test (table 9) show that the antimicrobial substance was not inactivated by pepsin treatment. Therefore, the active one or more antimicrobial compounds in the *C. finmarchicus* composition is probably not a protein.

TABLE 9

Development of turbidity in serial dilutions of pepsin treated aqueous phase from *C. finmarchicus* (catch 2), after inoculation with the test organisms *Staphylococcus aureus*

| Enzyme treatment | Dilution | | | | | | |
|---|---|---|---|---|---|---|---|
| | × 2 | × 4 | × 8 | × 16 | × 32 | × 64 | Water |
| Acid and pepsin | − | − | − | − | + | + | + |
| Acid | − | − | − | − | + | + | + |
| No inoculum | − | − | − | − | − | − | − |

1 ml of the aqueous phase from catch 2 was added 0.3 ml 0.1 N NaOH to obtain pH 8.0 and then added 0.2 ml 1% (w/v) alcalase 2.4 (Novozymes) adjusted to pH 8.0. The reaction mixture (pH 8.0) was incubated at 54° C. for 4 hours with occasional stirring. As a control, 1 ml of the aqueous phase was incubated similarly after addition of the same amount of alcali without alcalase. The results of the BTD test (table 10) show that the antimicrobial substance was not inactivated by alcalase treatment. Therefore, the active one or more antimicrobial compounds in the *C. finmarchicus* composition is probably not a protein.

TABLE 10

Development of turbidity in serial dilutions of alcalase treated aqueous phase from *C. finmarchicus* (catch 2), after inoculation with the test organisms *Staphylococcus aureus*

| Enzyme treatment | Dilution | | | | | | |
|---|---|---|---|---|---|---|---|
| | × 2 | × 4 | × 8 | × 16 | × 32 | × 64 | Water |
| Alcali and alcalase | − | − | − | − | + | + | + |
| Alcali | − | − | − | − | + | + | + |
| No inoculum | − | − | − | − | − | − | − |

1 ml of the aqueous phase from catch 2 was added 0.1 ml 0.5% (w/v) Proteinase K (Merck 1.24568.0100) in water. The reaction mixture (pH 6.5) was incubated at 37° C. for 4 hours with occasional stirring. As a control, 1 ml of the aqueous phase (pH 6.5) was incubated similarly after addition of 0.1 ml water without Proteinase K. The results of the BTD test (table 11) show that the antimicrobial substance was not inactivated by Proteinase K treatment. Therefore, the active one or more antimicrobial compounds in the *C. finmarchicus* composition is probably not a protein.

TABLE 11

Development of turbidity in serial dilutions of Proteinase K treated aqueous phase from *C. finmarchicus* (catch 2), after inoculation with the test organisms *Staphylococcus aureus*

| Enzyme treatment | Dilution | | | | | | |
|---|---|---|---|---|---|---|---|
| | × 2 | × 4 | × 8 | × 16 | × 32 | × 64 | Water |
| Proteinase K in water | − | − | − | − | − | + | + |
| Water | − | − | − | − | − | + | + |
| No inoculum | − | − | − | − | − | − | − |

Example 7

Estimation of Molecular Size of the Antimicrobial Substance

Molecular size of the antimicrobial substance, i.e. the size of the one or more antimicrobial compounds comprised within the antimicrobial composition of the present invention, was estimated by processing the aqueous phase through centrifugal filter devices (Pall Corporation) with MWCO (molecular weight cut off) of 30, 3 and 1 kDa. The results of the BTD test (table 12) indicate that the molecular weight of the antimicrobial substance is equal to, or less than 1 kDa.

TABLE 12

Development of turbidity in serial dilutions of aqueous phase from *C. finmarchicus* (catch 2), before and after processing through centrifugal filter devices with different molecular weight cut off limits. Test organism was *Staphylococcus aureus*

| Fraction tested | Dilution | | | | | | |
|---|---|---|---|---|---|---|---|
| | × 2 | × 4 | × 8 | × 16 | × 32 | × 64 | Water |
| Aqueous phase | − | − | − | − | + | + | + |
| Filtrate, 30 kDa | − | − | − | − | + | + | + |

TABLE 12-continued

Development of turbidity in serial dilutions of aqueous phase from
C. finmarchicus (catch 2), before and after processing through
centrifugal filter devices with different molecular weight cut off limits.
Test organism was Staphylococcus aureus

| Fraction tested | Dilution | | | | | | |
|---|---|---|---|---|---|---|---|
| | ×2 | ×4 | ×8 | ×16 | ×32 | ×64 | Water |
| Filtrate, 3 kDa | − | − | − | − | + | + | + |
| Filtrate, 1 kDa | − | − | − | − | + | + | + |
| No inoculum | − | − | − | − | − | − | − |

Example 8

Type of Action

There are three types of action of antimicrobial agents; i) static action where growth is inhibited, ii) cidal action where organisms are killed and iii) lytic action where organisms are killed and lysed.

After 24 hours incubation of the test tubes in table 7 (aqueous phase), 10 μl from each ×2 dilution was transferred to selected agar media. No colonies could be observed after 72 hours incubation of the agar media. Consequently, an initial cell concentration of approximately 10 E7 per ml was reduced to less than 10 E2 per ml, corresponding to 5 $LOG_{10}$ cycles reduction. The type of action is therefore cidic or lytic.

To determine whether the type of action is cidic or lytic, exponential phase cultures of *Escherichia coli, Salmonella berta*, and *Staphylococcus aureus* in Nutrient Broth were diluted to 1.0 E7-1.0 E8 in the same medium. 1 ml methanol extract were added to 9 ml of each culture, immediately after quantification at 0 hours. Cultures were then incubated at 37° C. for 96 hours. Viable cell counts were determined using 3M Petrifilm Aerobic Count Plates while total cell counts were determined using a microscope and Helber counting chamber. The results depicted in table 13 show that the action is bacteriocidic, not bacteriolytic.

TABLE 13

Development of viable cell counts and total cell counts in Nutrient
Broth with added methanol extract (10 %) from C. finmarchicus.

| Test organism | Quantification method | Incubation time (hours) | | | |
|---|---|---|---|---|---|
| | | 0 h | 3 h | 24 h | 96 h |
| E.coli | Viable cell counts | 3.2 E7 | 7.0 E6 | <1.0 E1 | <1.0 E1 |
| | Total cell counts | 6.0 E7 | 6.0 E7 | 2.0 E7 | 1.0 E7 |
| S.berta | Viable cell counts | 3.9 E7 | 7.0 E6 | 2.9 E2 | <1.0 E1 |
| | Total cell counts | 6.0 E7 | 6.0 E7 | 6.0 E7 | 1.0 E7 |
| S.aureus | Viable cell counts | 1.5 E7 | 7.4 E6 | 2.0 E5 | <1.0 E1 |
| | Total cell counts | 6.0 E7 | 4.0 E7 | 4.0 E7 | 4.0 E7 |

Example 9

Investigation of Antimicrobial Activity in *C. hyperboreus*

Antimicrobial activity was not detected in the aqueous phase from another copepod species, *C. hyperboreus*.

Aqueous phase prepared from a frozen sample of *C. hyperboreus* was tested against *S. aureus* (ATCC 25923). A methanol extract of *C. finmarchicus* with known activity was tested simultaneously against the same test organism as a control on the test system. *C. hyperboreus* was caught in the Norwegian Sea on May 15, 2006. Antimicrobial activity was not detected in the aqueous phase from *C. hyperboreus*.

TABLE 14

Comparison of antimicrobial activity in *C. hyperboreus* and *C. finmarchicus*

| Sample | Dilution | | | | | | | | |
|---|---|---|---|---|---|---|---|---|---|
| | ×2 | ×4 | ×8 | ×16 | ×32 | ×64 | ×128 | ×256 | Water |
| C. hyperboreus Aqueous phase | + | + | + | + | + | + | + | + | + |
| C. finmarchicus Methanol extract | − | − | − | − | − | − | − | + | + |

+: turbidity,
−: no turbidity

Example 10

Comparison of BTD and Agar Diffusion Assay

Antimicrobial activity in the aqueous or water phase from *C. finmarchicus*, was easily detected using the BTD (Broth Tube Dilution) method. Surprisingly, the agar diffusion assay, which is frequently used for the initial screening of antimicrobial activity, did not detect this activity. This may explain why the antimicrobial activity in water phase from this organism has not been discovered earlier.

When the BTD method was compared to the agar diffusion assay for detection of activity in the methanol extract from *C. finmarchicus*, it appeared that the BTD method was 32-64 times more sensitive than the agar diffusion assay. *Staphylococcus aureus* (ATCC 25923) was used as test strain in both the Broth Tube Dilution Method and the Agar Diffusion Assay. With the Agar Diffusion Well method, well diameter was 9 mm and each well was filled with 200 μl of the extract or its dilution. In the Agar Diffusion Filter disc method, 13 mm diameter discs (Whatman Cat. No. 2017-013) was used. Results are shown in table 15.

TABLE 15

Comparison of BTD and Agar Diffusion Assay for detection of
antimicrobial activity in methanol extract from C. finmarchicus.

| Test organism | Dilution | | | | | | | | | |
|---|---|---|---|---|---|---|---|---|---|---|
| | 0 | ×2 | ×4 | ×8 | ×16 | ×32 | ×64 | ×128 | ×256 | Water |
| Broth Tube Dilution | | − | − | − | − | − | − | − | + | + |
| Agar Diffusion Assay, Well method | 13 | 10 | 5 | 0 | 0 | 0 | 0 | 0 | 0 | 0 |
| Agar Diffusion | 4 | 1 | 0 | 0 | 0 | 0 | 0 | 0 | 0 | 0 |

TABLE 15-continued

Comparison of BTD and Agar Diffusion Assay for detection of antimicrobial activity in methanol extract from C. finmarchicus.

| Test organism | Dilution | | | | | | | | | |
|---|---|---|---|---|---|---|---|---|---|---|
| | 0 | ×2 | ×4 | ×8 | ×16 | ×32 | ×64 | ×128 | ×256 | Water |
| Assay, Filter disc method | | | | | | | | | | |

+: turbidity,
−: no turbidity.

For the Agar Diffusion Assay, activity is expressed by inhibition zone width (mm).

The agar diffusion assay is a technique for quantifying the ability of antimicrobial agents to inhibit bacterial growth. It has a number of variations, including the well method and the filter disc method. Interpretation of the results from this assay relies on mathematical models, based on the assumption that the agents diffuse freely in the solid nutrient medium. The technique is commonly used for determination of MIC values (Minimal Inhibitory Concentration) in solid media, such as Nutrient Agar. Solutions of antimicrobial agents at different concentrations are applied to wells punched into agar or to paper discs placed on the surface of or plates seeded with the test microbial strains. Diffusion from the sources into the agar leads to growth inhibition in the vicinity of the source and to the formation of clear zones without bacterial growth. The zone diameter corresponds to the concentration of the antimicrobial agent.

Example 11

Antifungal Activity of Methanol Extract

A mould species, *Aspergillus niger* (ATCC 16404), was inhibited by the aqueous phase from *C. finmarchicus* (data not shown).

The methanol extract was tested against two yeast species; *Saccharomyces cerevisiae* and *Candida albicans* and one mould species; *Aspergillus niger*. *C. albicans* is the least susceptible of the organisms tested. *S. aureus* was included as a control. Results are shown in table 16.

TABLE 16

Antifungal activity of methanol extract

| Test organism | Dilution | | | | | | | | |
|---|---|---|---|---|---|---|---|---|---|
| | ×2 | ×4 | ×8 | ×16 | ×32 | ×64 | ×128 | ×256 | Water |
| C. albicans (ATCC 10231) | − | + | + | + | + | + | + | + | + |
| S. cerevisiae | − | − | − | − | + | + | + | + | + |
| A. niger (ATCC 16404) | − | − | − | − | − | − | + | + | + |
| S. aureus (ATCC 25923) | − | − | − | − | − | − | − | + | + |
| No inoculum | − | − | − | − | − | − | − | − | − |

+: turbidity,
−: no turbidity

Example 12

Effect on Resistant Bacterial Strains

The methanol extract was tested against meticillin-resistant *S. aureus* (ATCC 43300) and multiresistant clinical isolates of *P. aeruginosa*, *Klebsiella pneumoniae* and *Acinetobacter*. All the isolates were strongly inhibited. *S. aureus* (ATCC 25923) was included in the study as a positive control. Results are shown in table 17.

TABLE 17

Antibiotic effect against resistant bacteria

| Test organism | Dilution | | | | | | | | |
|---|---|---|---|---|---|---|---|---|---|
| | ×2 | ×4 | ×8 | ×16 | ×32 | ×64 | ×128 | ×256 | Water |
| MRSA (ATCC 43300) | − | − | − | − | − | − | + | + | + |
| P. aeruginosa | − | − | − | − | − | − | + | + | + |
| K. pneumoniae | − | − | − | − | − | − | − | + | + |
| Acinetobacter | − | − | − | − | − | − | − | + | + |
| S. aureus (ATCC 25923) | − | − | − | − | − | − | − | + | + |
| No inoculum | − | − | − | − | − | − | − | − | − |

+: turbidity,
−: no turbidity

Methicillin Resistant *Staphylococcus aureus* (MRSA) (ATCC 43300)

The strain is resistant to all β-lactam antibiotics. The treatment of MRSA is therefore difficult. The strain can cause both local and systemic infections.

*Klebsiella pneumoniae*, Multiresistant Clinical Isolate (Ref. No.: HUS11090921/08)

The strain has a plasmid-mediated, broad spectrum β-lactamase (*Klebsiella Pneumoniae* Carbapenemase (KPC) and is resistant to all clinical relevant β-lactam antibiotics. Furthermore, it is in vitro resistant to many other non β-lactam antibiotics. Infections with such microbes are difficult to treat with available antibiotics. *K. pneumoniae* is a common cause of urinary tract infections, but can also cause systemic infections.

*Pseudomonas aeruginosa*, Multiresistant Clinical Isolate (Ref. No.: HUS10210891/07)

*P. aeruginosa* is naturally resistant to a range of different antibiotics, and the spectre of efficient agents is narrow. Additionally, it has a high ability to develop resistance to new antibiotics. The actual strain is in vitro resistant to, or has reduced susceptibility to antimicrobial agents commonly used in the treatment of *P. aeruginosa* infections. Severe infections with *P. aeruginosa* occur with immune deficient patients and with weak, hospitalized patients.

*Acinetobacter*, Multiresistant Clinical Isolate (Ref. No.: HUS11232851/08)

*Acinetobacter* is naturally resistant to a range of different antibiotics, and the spectre of efficient agents is narrow. With one exception, the actual isolate in vitro resistant to, or have reduced susceptibility to all antimicrobial agents used for treatment of Acinetobacter infections. Severe infections with *Acinetobacter* occur with immune deficient patients and with weak, hospitalized patients.

Example 13

Further Extraction and Analysis of the Methanol Extract

Sample Preparations

Three different sample preparations were tested. This was done to find the best preparation prior to HPLC, i.e. the method that had best recovery, and at the same time rendered a fraction that was pure enough to be loaded onto an HPLC-column.

1: Wessel-Flügge Extraction.

The extract was dissolved in water and methanol, added chloroform and vortexed. The result is three fractions; water-methanol, methanol-chloroform and the precipitate. All fractions were evaporated and tested for activity. The activity is measured as the MIC as described in example 2.

TABLE 18

Bioactivity in the Wessel-Flügge fractions.

| Fraction | MIC |
| --- | --- |
| Water-methanol | 32 |
| Methanol-chloroform | 2 |
| Precipitate | 0 |

2: Solid Phase Extraction (SPE), Anion Exchange.

The cartridge (Sep-Pak plus QMA, Waters corp.) was first wetted with methanol, and then equilibrated with water. The extract was loaded and the cartridge was washed with water, and finally with methanol to elute polar and weak anionic compounds. Two fractions: Water wash and methanol elute. The fractions were evaporated, dissolved in a volume of water corresponding to the sample load volume, and tested for bioactivity.

TABLE 19

Bioactivity in the anion exchange SPE fractions.

| Fraction | MIC |
| --- | --- |
| Wash | 64 |
| Methanol elute | 0 |

3: Solid Phase Extraction, Reversed Phase.

The cartridge (Sep-Pak plus C18, Waters corp.) was first wetted with acetonitrile, and then equilibrated with water. The extract was loaded onto the cartridge, and the cartridge was washed with water, then with 40% acetonitrile and 100% acetonitrile to elute non-polar compounds. Three fractions: Wash, elute 1 (intermediate polarity) and elute 2 (low polarity). The fractions were evaporated and tested for bioactivity

TABLE 20

Bioactivity in the reversed phase SPE fractions.

| Fraction | MIC |
| --- | --- |
| Wash | 32 |
| Elute 1 | 16 |
| Elute 2 | 2 |

The bioactive compound(s) is probably polar or charged since it was found in the aqueous fraction from the Wessel-Flügge extraction as well as the wash fraction in the reversed phase extraction. It is not likely to be a strong anionic compound since it failed to bind to the anionic solid phase cartridge. Anion exchange solid phase extraction was used as sample preparation prior to HPLC since all the activity eluted in one fraction.

HPLC

Our first attempt was conventional reversed phase chromatography. The active fraction (wash) from the anion exchange extraction was dried and dissolved in water and injected onto a C18 column (250×4.6 mm). The gradient was from 96% water to 100% acetonitrile as shown in FIG. 3 (green line). One-minute fractions were collected, evaporated and dissolved to the sample volume, and tested for bioactivity.

TABLE 21

Bioactivity of the analytical reversed phase HPLC fractions.

| Fraction | MIC |
| --- | --- |
| 2 | 0 |
| 3 | 0 |
| 4 | 16 |
| 5 | 8 |
| 6 | 4 |
| 7 | 0 |
| 8 | 0 |

Later fractions had no bioactivity

Comparison of Chromatography with or without Polar End-capping

The bioactivity data in Table 21 and the corresponding chromatogram (FIG. 3) suggest that the bioactivity is too polar to be separated by conventional reversed phase chromatography. The active fractions were re-chromatographed under identical conditions, or with a column with polar end-capping (Aquasil, Hypersil). The latter column is suitable for isolation of polar or charged compounds. This column gave better separation of the active fraction (Fraction 4, FIG. 4). However, the Aquasil-column was too small to make fractions for bioactivity testing. Up-scaling to a semi-preparative Aquasil column failed.

Semi-Preparative Reversed-Phase HPLC:

The extract from the anion exchange SPE was loaded onto a semi-preparative C18 column and eluted with a gradient with increasing acetonitrile. Fractions were collected and tested for bioactivity. As shown in Table 22, the bioactivity eluted early. The active fraction was used for further experiments in purification.

TABLE 22

Bioactivity of the semi-preparative fractions.

| Fraction | Retention time | MIC |
|---|---|---|
| 2 | 0-5.3 | 16 |
| 3 | 5.3-7.2 | 4 |
| 4 | 10.8-13.4 | 0 |
| 5 | 18.1-19.3 | 0 |
| 6 | 19.4-21.6 | 0 |
| 7 | 21.6-23.3 | 0 |
| 8 | 23.3-25.1 | 0 |

Normal-Phase HPLC.

The active fraction from the semi-preparative reversed phase chromatography (FIG. 5 and table 22) was loaded onto an analytical normal phase column under isocratic mode. As mobile phase, six different ratios of ethyl acetate (EtOAc) and methanol (MeOH) was tried: 1/99; 5/95; 10/90; 20/80; 40/60 (EtOAc/MeOH, v/v %).

This turned out to be a promising method, and another run with more material was performed. One-minute fractions were collected and tested for bioactivity.

TABLE 23

Bioactivity of the normal phase fractions.

| Fraction | MIC |
|---|---|
| 3 | 0 |
| 4 | 4 |
| 5 | <2 |
| 6 | 0 |
| 7 | 0 |
| 8 | 0 |

Mass Spectrometric Analyses of the Active Peak.

The experiment described in the previous paragraph was repeated and fraction 4 was analysed by a Q-trap mass spectrometer (direct infusion). Two peaks stood out from the background (m/z=347 and 245). These were further fragmented, but no certain conclusions can be drawn based on these data.

A search on various databases on natural compounds with mass=346 Da (corresponding to m/z=347), returned a hit on penostatin depicted in FIG. 12 (Iwamoto et al. Tetrahedron, 1999 vol. 55 p. 14353). This is a mild cytotoxic compound that was isolated from a fungus that grows on the green algae *Enteromorpha intestinalis*. The UV-spectra of this and related compounds are similar to that of the active fraction from the normal phase purification (FIG. 8).

The invention claimed is:

1. A method for the inhibition of bacterial growth and/or for the killing of bacteria in a product, comprising the step of adding to the product a composition comprising an effective amount of an extract obtained from the copepod *Calanus finmarchicus*, thereby inhibiting bacterial growth and/or killing said bacteria.

2. The method according to claim 1, wherein said antibacterial composition is selected from the group consisting of a preservative, an antiseptic, a disinfectant, an anti-fouling agent and a medicament.

3. The method according to claim 2, wherein said antibacterial composition is a preservative in a food product, feed composition, beverage, cosmetics or pharmaceuticals.

4. The method according to claim 1, wherein the bacteria are selected from the genera of the group consisting of *Pseudomonas, Enterococcus, Listeria, Bacillus, Staphylococcus, Escherichia, Salmonella*, and *Clostridium*.

5. The method according to claim 1, wherein the bacteria are selected from the group consisting of *Pseudomonas aeruginosa, Enterococcus faecalis, Listeria monocytogenes, Bacillus cereus, Staphylococcus aureus, Escherichia coli, Salmonella berta, Clostridium perfringens* and *Clostridium bifermentans*.

6. A method for treatment of a bacterial infection in an individual in need thereof comprising the step of administering to the individual a composition comprising a therapeutically effective amount of an extract obtained from the copepod *Calanus finmarchicus*.

7. The method according to claim 6, wherein said treatment is ameliorating or prophylactic.

8. The method according to claim 6, wherein said composition is an antibiotic.

9. The method according to claim 6, wherein said microbial infection is caused by one or more resistant bacteria with resistance to one or more antibiotics.

10. The method according to claim 6, wherein said bacterium is selected from the group consisting of a methicillin-resistant *Staphylococcus aureus*, a multiresistant *Pseudomonas aeruginosa*, a multiresistant *Klebsiella pneumoniae*, and a multiresistant *Acinetobacter*.

11. The method according to claim 6, wherein said individual is a human being.

12. The method according to claim 6, wherein said individual is infected with one or more pathogenic bacteria.

13. The method according to claim 6, wherein said individual is infected with one or more pathogenic bacteria resistant to one or more antibiotics.

14. The method according to claim 6, wherein said composition is administered to an individual in need thereof by topical, enteral or parenteral administration.

15. The method according to claim 6, wherein said composition is co-administered with one or more additional drugs.

16. The method according to claim 15, wherein said one or more additional drugs comprise one or more antibiotics.

* * * * *